(12) United States Patent
Zhang et al.

(10) Patent No.: US 12,331,059 B2
(45) Date of Patent: Jun. 17, 2025

(54) CLASS OF FUNCTIONAL MOLECULES TARGETING PROTEOLYSIS PATHWAYS, PREPARATION AND APPLICATION THEREOF

(71) Applicant: Institute of Materia Medica, Chinese Academy of Medical Sciences, Beijing (CN)

(72) Inventors: Chongjing Zhang, Beijing (CN); Fujia Wang, Beijing (CN); Zi Ye, Beijing (CN); Wanqi Yang, Beijing (CN); Ke Li, Beijing (CN)

(73) Assignee: Institute of Materia Medica, Chinese Academy of Medical Sciences, Beijing (CN)

( * ) Notice: Subject to any disclaimer, the term of this patent is extended or adjusted under 35 U.S.C. 154(b) by 771 days.

(21) Appl. No.: 17/641,485

(22) PCT Filed: Sep. 9, 2020

(86) PCT No.: PCT/CN2020/114125
§ 371 (c)(1),
(2) Date: Mar. 9, 2022

(87) PCT Pub. No.: WO2021/047524
PCT Pub. Date: Mar. 18, 2021

(65) Prior Publication Data
US 2022/0380381 A1    Dec. 1, 2022

(30) Foreign Application Priority Data
Sep. 9, 2019 (CN) .......................... 201910848612.9

(51) Int. Cl.
C07D 493/18 (2006.01)
A61P 35/02 (2006.01)
C07D 417/14 (2006.01)

(52) U.S. Cl.
CPC ............ *C07D 493/18* (2013.01); *A61P 35/02* (2018.01); *C07D 417/14* (2013.01)

(58) Field of Classification Search
None
See application file for complete search history.

(56) References Cited

FOREIGN PATENT DOCUMENTS

| WO | 2016146985 A1 | 9/2016 |
| WO | 2018081530 A1 | 5/2018 |
| WO | 2018106870 A1 | 6/2018 |

OTHER PUBLICATIONS

Crew et al., Journal of Medicinal Chemistry 2018 61 (2), 583-598 (Year: 2018).*

(Continued)

*Primary Examiner* — Jeffrey S Lundgren
*Assistant Examiner* — Anthony Joseph Seitz
(74) *Attorney, Agent, or Firm* — Duane Morris LLP

(57) ABSTRACT

The present invention belongs to the field of medical technology and relates to a class of functional small molecules targeting proteolysis pathways, a preparation and an application thereof. Specifically, the present invention relates to functional small molecules represented by formula (M) and pharmaceutically acceptable salts thereof, as well as the application of said compounds and pharmaceutical compositions thereof in the preparation of tumor-treating drugs. The functional small molecules are obtained by means of linking a compound containing a peroxide bridge linkage and a substrate of an E3 ubiquitin ligase complex. The related functional molecules can promiscuously target and bind to multiple proteins comprising functional proteins in the proteolysis pathway and have anti-tumor biological activity.

(Continued)

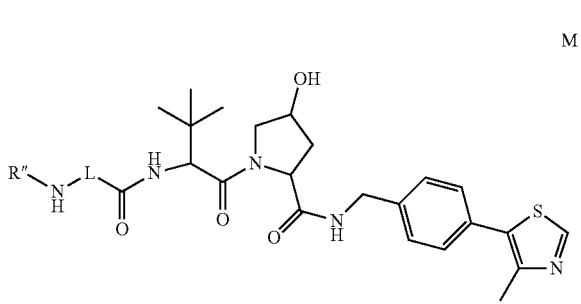

11 Claims, 7 Drawing Sheets

(56) References Cited

OTHER PUBLICATIONS

Figure 1:
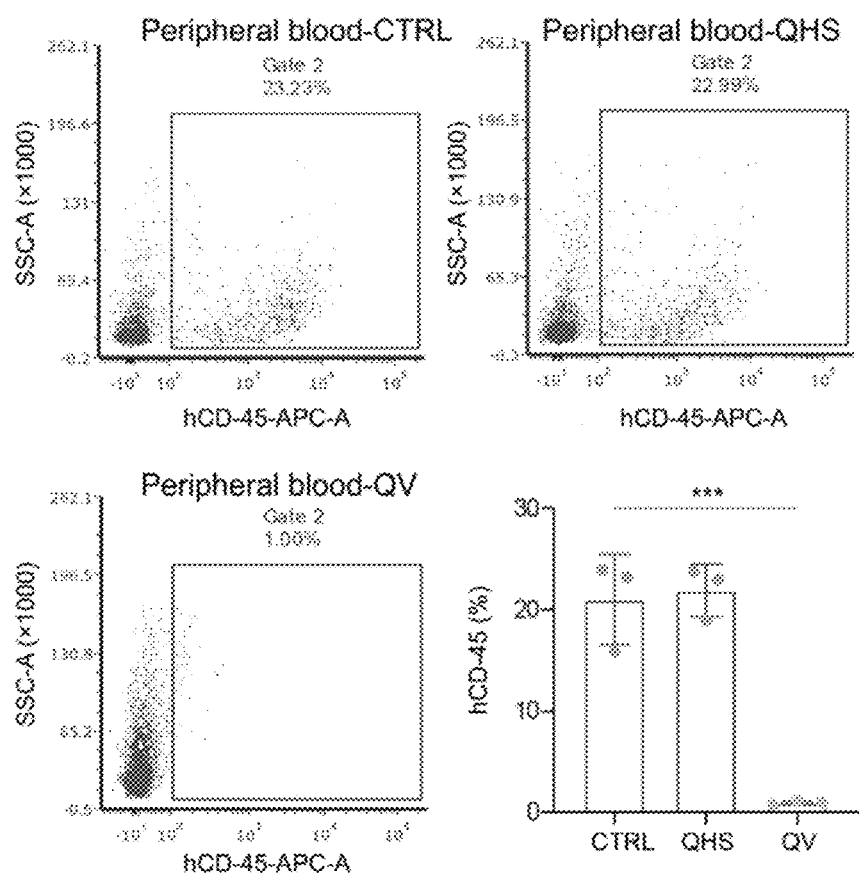

Magoulas et al., Bioorg Med Chem. Jul. 15, 2017;25(14):3756-3767. Epub May 10, 2017 (Year: 2017).*

Barton et al., Rationale Design of Biotinylated Antimalarial Endoperoxide Carbon Centered Radical Prodrugs for Applications in Proteomics, Journal of Medicinal Chemistry, 2010, vol. 53, No. 11, pp. 4555-4559, XP055054615, ISSN: 0022-2623, DOI: 10.1021/jml0020lj.

Magoulas et al., Synthesis of novel artemisinin dimers with polyamine linkers and evaluation of their potential as anticancer agents, Bioorganic & Medicinal Chemistry, Elsevier Ltd., May 10, 2017, vol. 25, pp. 3756-3767, XP085062436, ISSN: 0968-0896, DOI: 10.1016/J.BMC.2017.05.018.

Pensée et al., Artemisinin-Polypyrrole Conjugates: Synthesis, DNA Binding Studies and Preliminary Antiproliferative Evaluation, ChemMedChem Communications, Mar. 11, 2013, vol. 8, No. 5, pp. 709-718, XP072418675, ISSN: 1860-7179, DOI: 10.1002/CMDC.201200536.

Steinebach et al., PROTAC-mediated crosstalk between E3 ligases, Chemial Communications, vol. 55, No. 12, Jan. 1, 2019, pp. 1821-1824, XP055588704, ISSN: 1359-7345, DOI: 10.1039/C8CC09541H.

European Patent Office, Extended European Search Report issued Oct. 9, 2023, for corresponding European Patent Application No. 20862461.9.

Maniaci et al., Homo-PROTACs: bivalent small-molecule dimerizers of the VHL E3 ubiquitin ligase to induce self-degradation; Nature Communications., vol. 8, No. 830, Oct. 10, 2017; DOI: 10.1038/s41467-017-00954-1.

Sun et al., Targeting autophagy enhances the anticancer effect of artemisinin and its derivatives. Med Res Rev., vol. 39, No. 6, Apr. 11, 2019; Med Res Rev. 2019;39:2172-2193; https://doi.org/10.1002/med.21580.

Oh et al., Synthesis and anti-cancer activity of covalent conjugates of artemisinin and a transferrin-receptor targeting peptide. Cancer Letters., vol. 274 (2009); pp. 33-39.

China National Intellectual Property Administration (ISA/CN), International Search Report (English translation issued Dec. 9, 2020, for International Patent Application No. PCT/CN2020/114125.

* cited by examiner

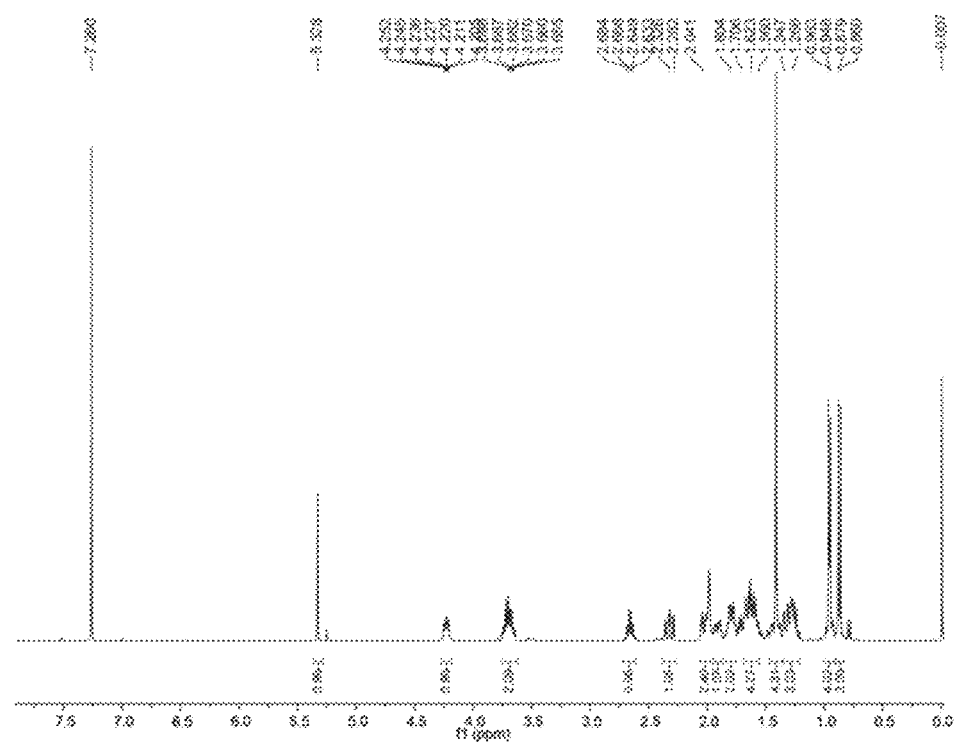
Figure 5
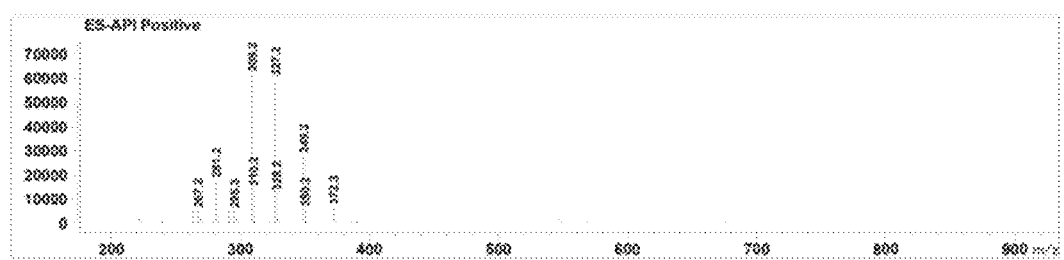
Figurer 6

CLASS OF FUNCTIONAL MOLECULES TARGETING PROTEOLYSIS PATHWAYS, PREPARATION AND APPLICATION THEREOF

PRIORITY CLAIM AND CROSS-REFERENCE

The present application is a National Stage Application, filed under 35 U.S.C. 371, of International Patent Application No. PCT/CN2020/114125, filed on Sep. 9, 2020 and published as WO 2021/047524 A1, which claims for the priority of Chinese Application No. 201910848612.9, filed on Sep. 9, 2019, each of which is incorporated herein by reference in its entirety.

FIELD OF THE INVENTION

The invention belongs to the technical field of medicine, which involved a kind of functional compounds targeting protein degradation pathway and their preparations and applications, and their pharmaceutically acceptable salts and pharmaceutical compositions in the treatment of tumor. In the present invention, the endoperoxide-containing ligands and E3 ligase-targeting ligands were connected via a linker to generate the functional compounds.

BACKGROUND OF THE INVENTION

Ubiquitin proteasome pathway (UPP) is the main approach to degrading cellular proteins. The UPP consists of ubiquitin, ubiquitin activation enzyme E1, ubiquitin binding enzyme E2, ubiquitin ligation enzyme E3, proteasome and its substrate protein. When the targeted proteins am degraded by UPP, these targeted proteins will be firstly ubiquitinated, followed by recognition by the proteasome complex. Finally, the targeted proteins am degraded into small peptides. The UPP system could eliminate the aged or damaged proteins, which plays a critical role in maintaining the normal cellular balance and biological functions.

Content of the Invention

This invention provides a series of novel compounds to target multiple proteins including those in the system of protein degradation. Specially, this invention contains a series of novel compounds and their preparations and applications in the treatment of tumor.

To fulfill the abovementioned scientific advances, this invention provides the following scientific methods.

In a first aspect of the present invention, there provides a compound of formula (M)

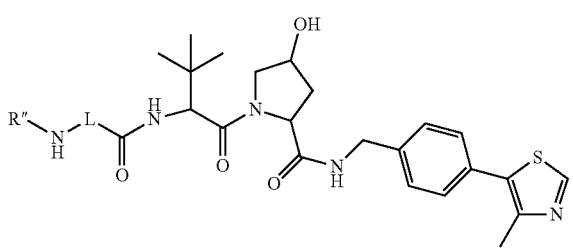

Wherein:
R" is

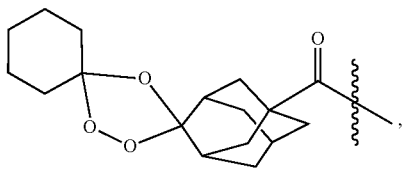
(R1)

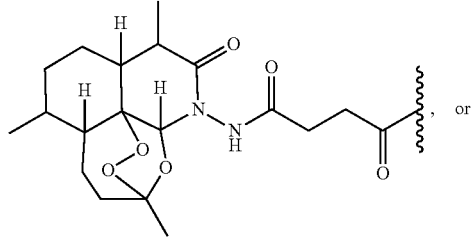
(R2)

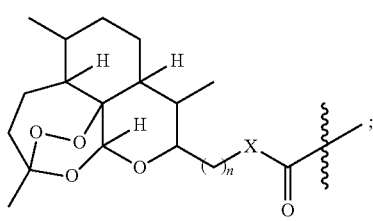
(R3)

L is selected from —$C_1$-$C_8$ alkylene, oxygen-containing alkylene,

The number of oxygen atoms in said oxygen-containing alkylene is 1, 2, 3, 4 or 5, said oxygen is connected with $C_2$ alkylene;

When R" is R3, n is independently selected from 0, 1, 2, 3, 4, 5; X is oxygen or —$CH_2$—, or a pharmaceutical acceptable salt thereof.

Preferably, the compound of resent invention has formula (I) and formula (II):

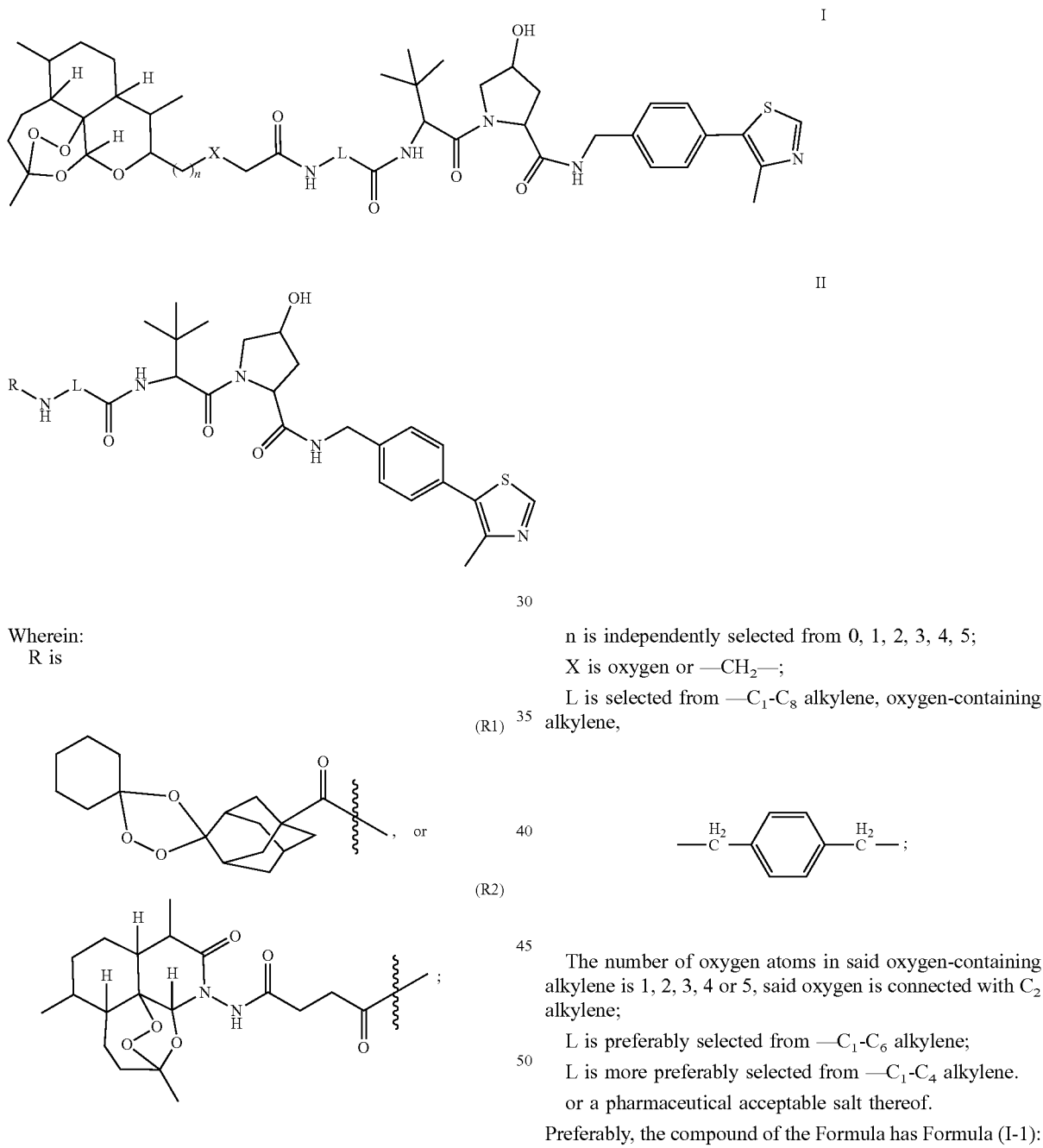

Wherein:
R is (R1)

, or (R2)

;

n is independently selected from 0, 1, 2, 3, 4, 5;
X is oxygen or —CH$_2$—;
L is selected from —C$_1$-C$_8$ alkylene, oxygen-containing alkylene,

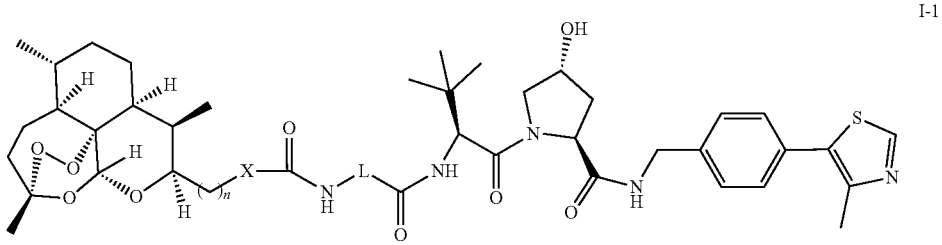

The number of oxygen atoms in said oxygen-containing alkylene is 1, 2, 3, 4 or 5, said oxygen is connected with C$_2$ alkylene;
L is preferably selected from —C$_1$-C$_6$ alkylene;
L is more preferably selected from —C$_1$-C$_4$ alkylene.
or a pharmaceutical acceptable salt thereof.
Preferably, the compound of the Formula has Formula (I-1):

I-1 wherein:
n is independently selected from 0, 1, 2, 3, 4, 5;
X is selected from oxygen or —CH$_2$—;
L is selected from —C$_1$-C$_8$ alkylene, oxygen-containing alkylene,

The number of oxygen atoms in said oxygen-containing alkylene is 1, 2, 3, 4 or 5, said oxygen is connected with C2 alkylene;

L is most preferably selected from the following structures:

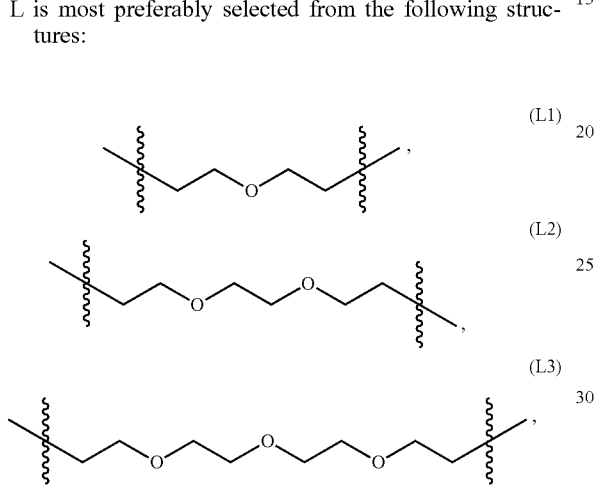

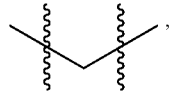 (L4)

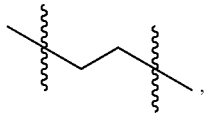 (L5)

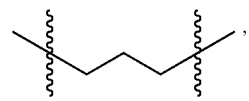 (L6)

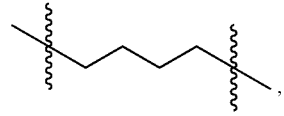 (L7)

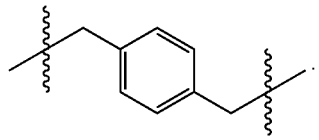 (L8)

The compounds of this invention are more preferably selected from:

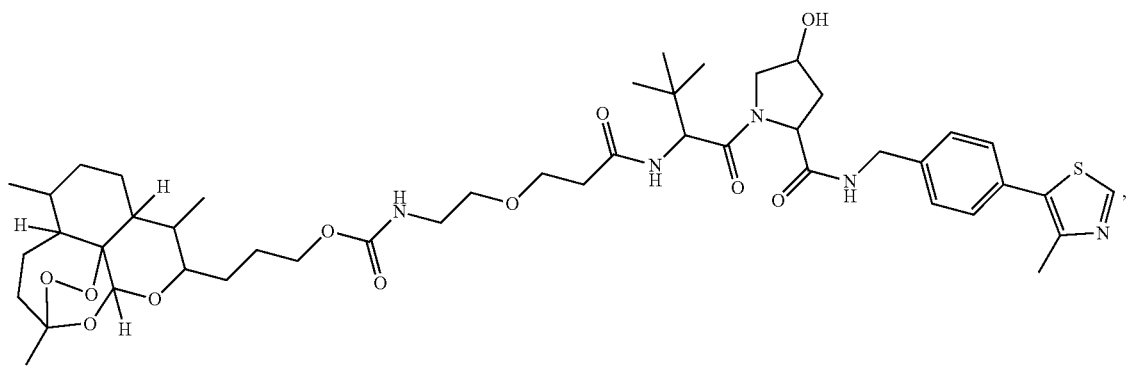

CL-1

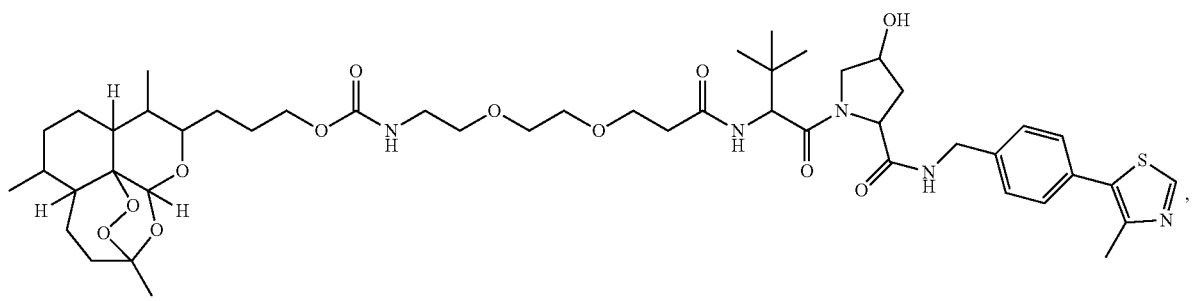

CL-2

-continued
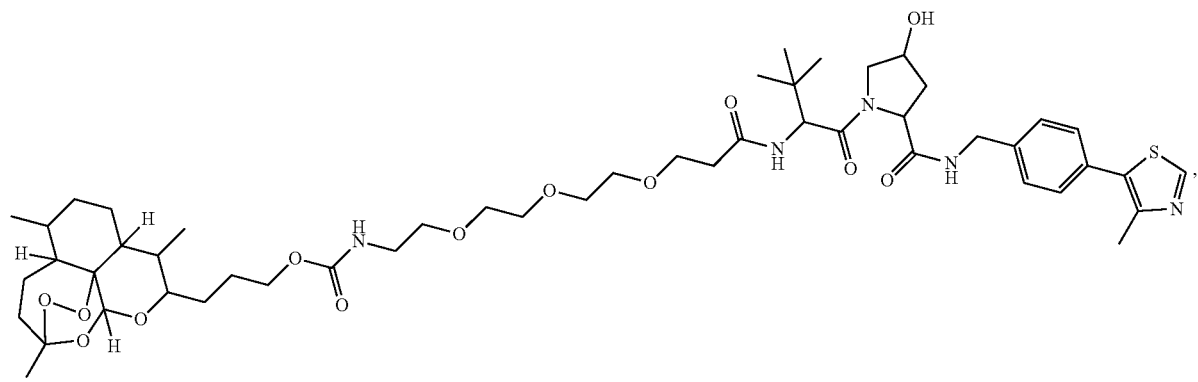
CL-3
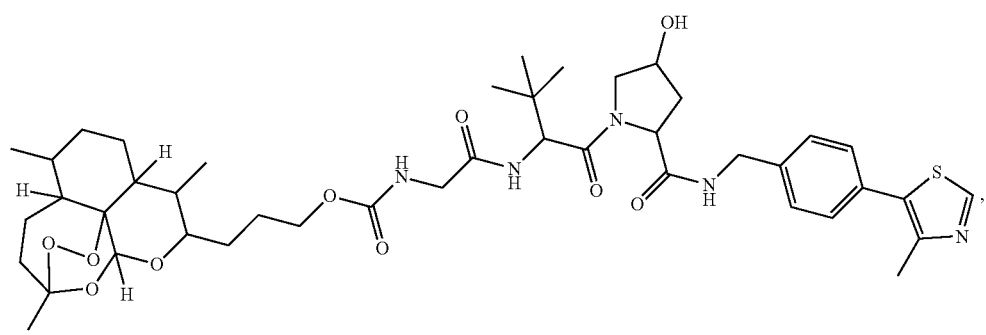
CL-4
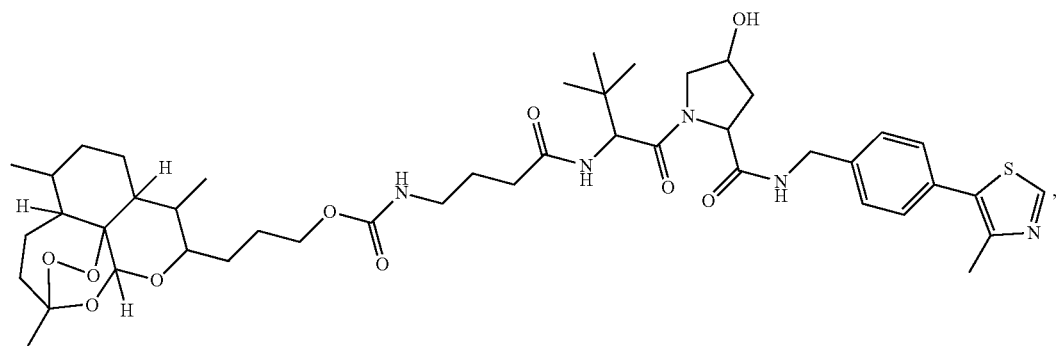
CL-5
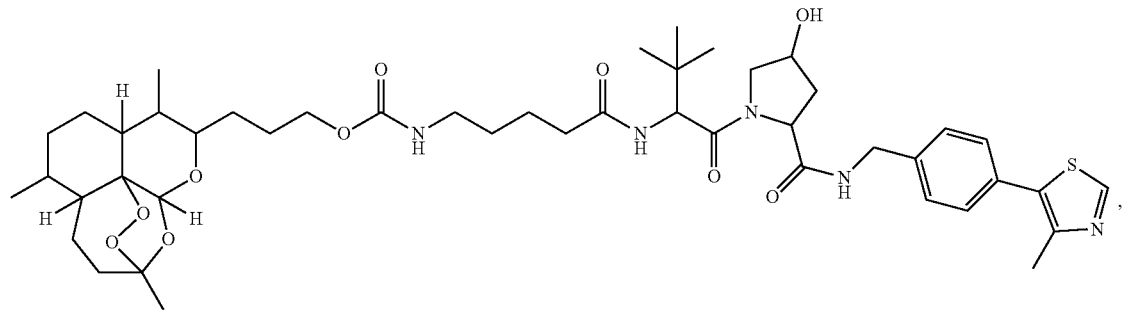
CL-6

-continued
CL-7
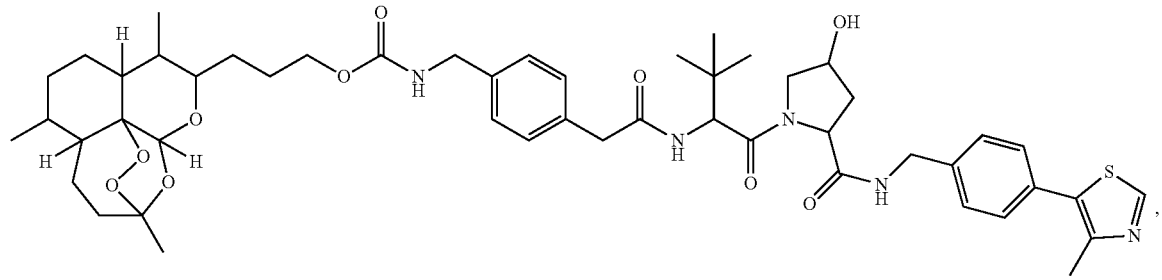
CL-8
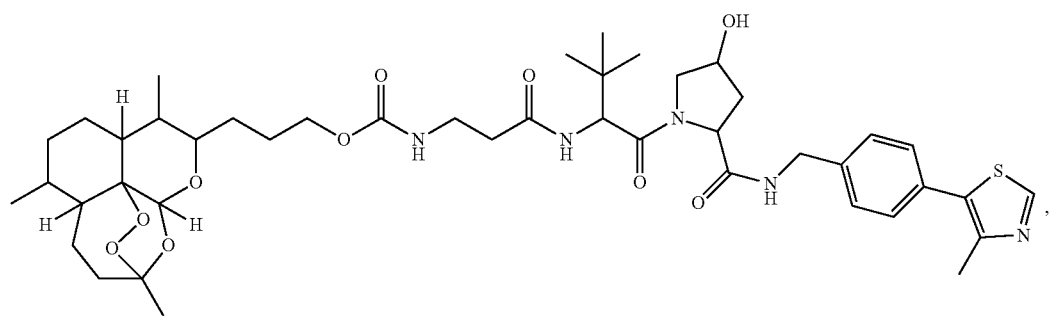
CL-9
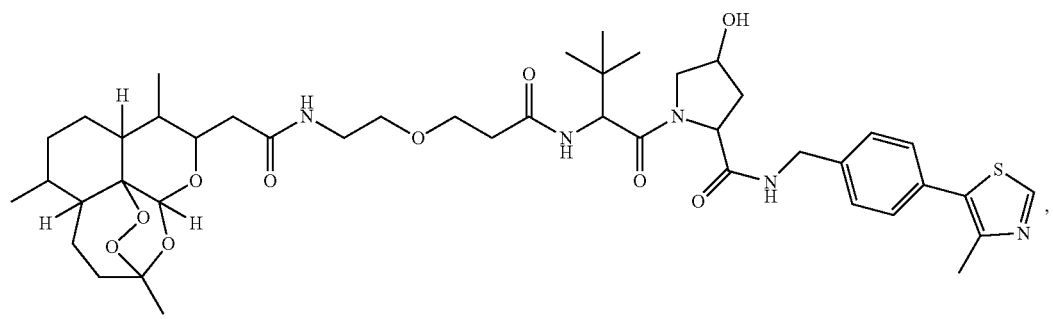
CL-10
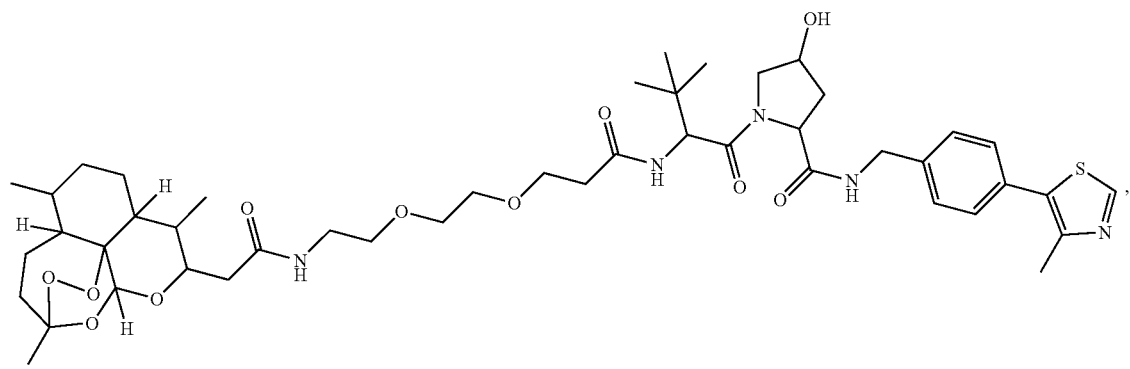
C-11
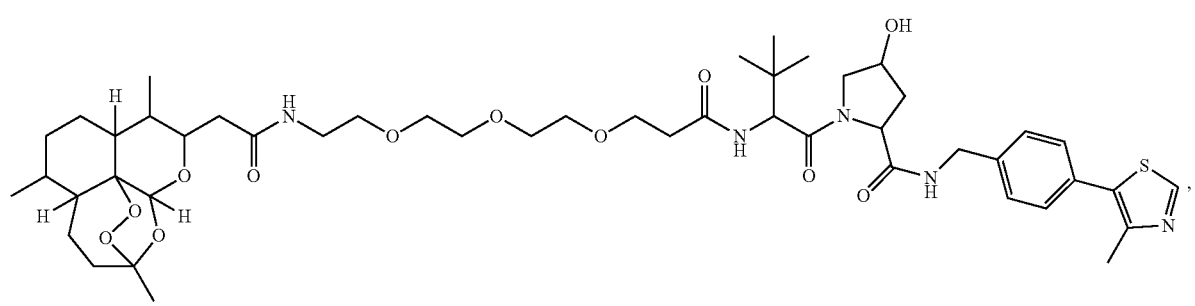

-continued
CL-12
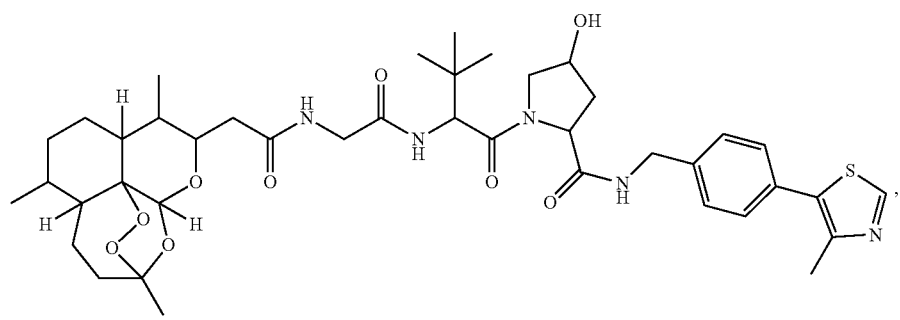
CL-13
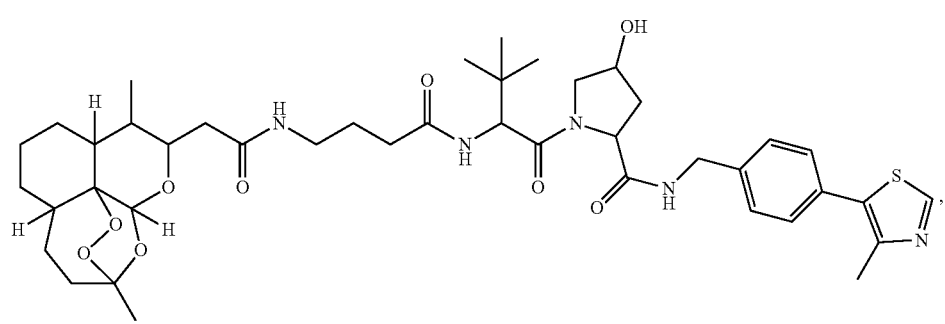
CL-14
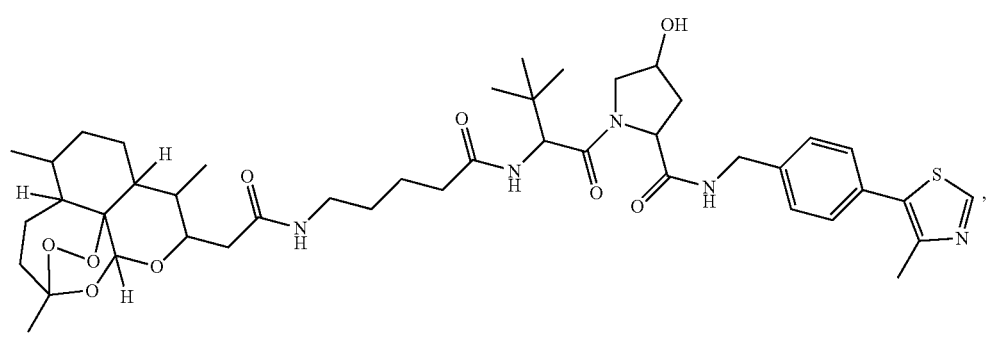
CL-15
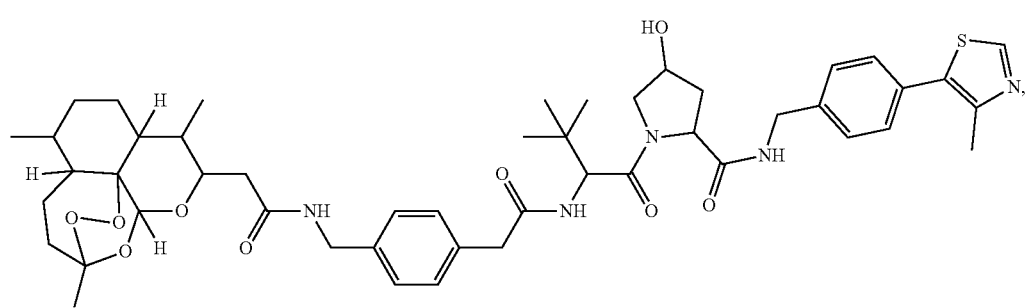

-continued
CL-16
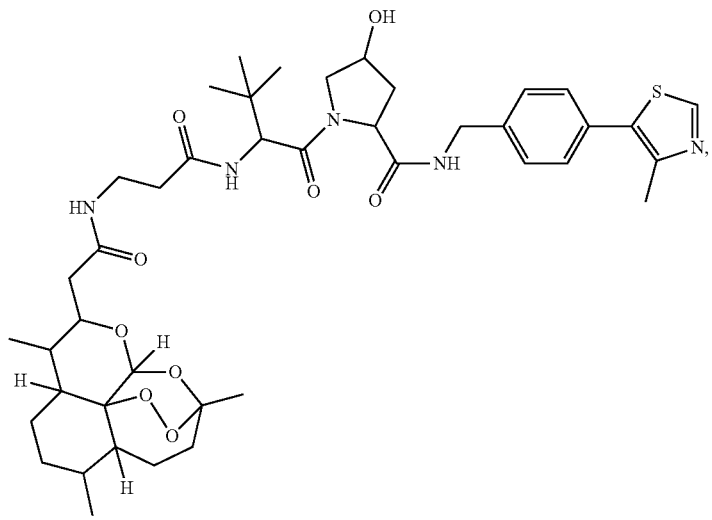
CL-17
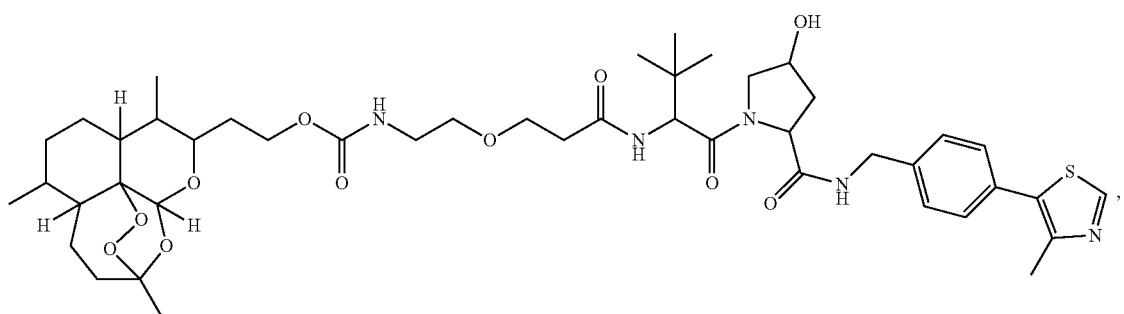
CL-18
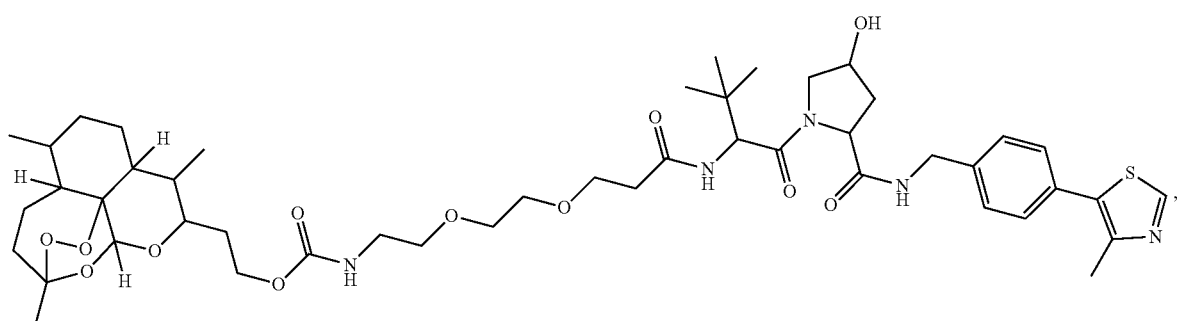
CL-19
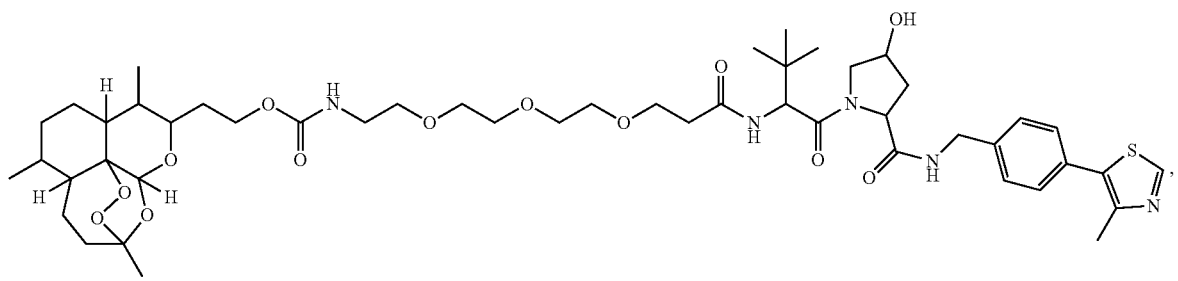

-continued
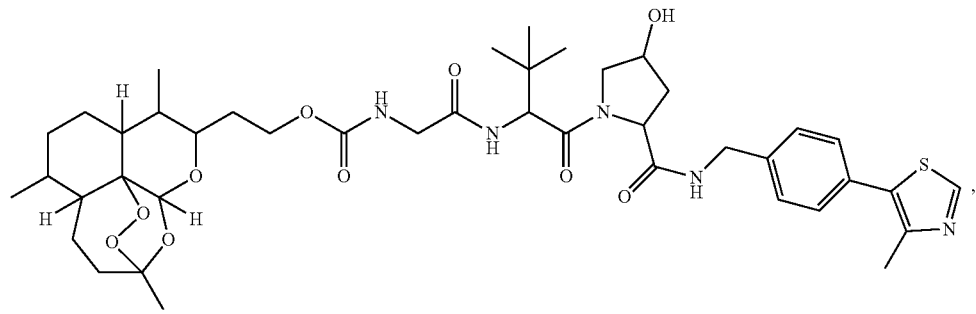
CL-20
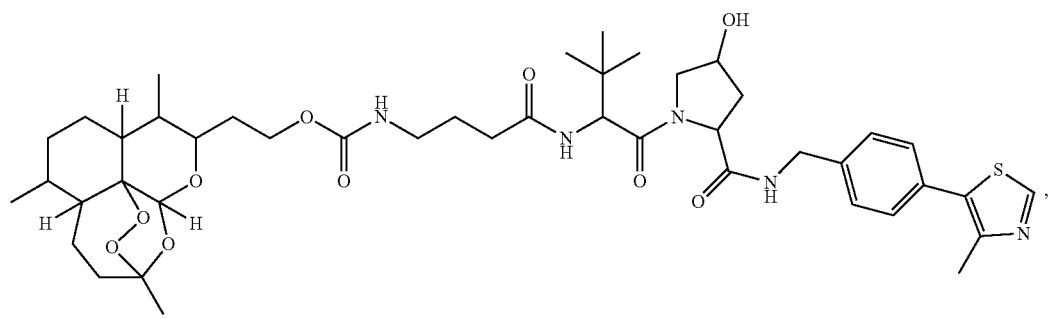
CL-21
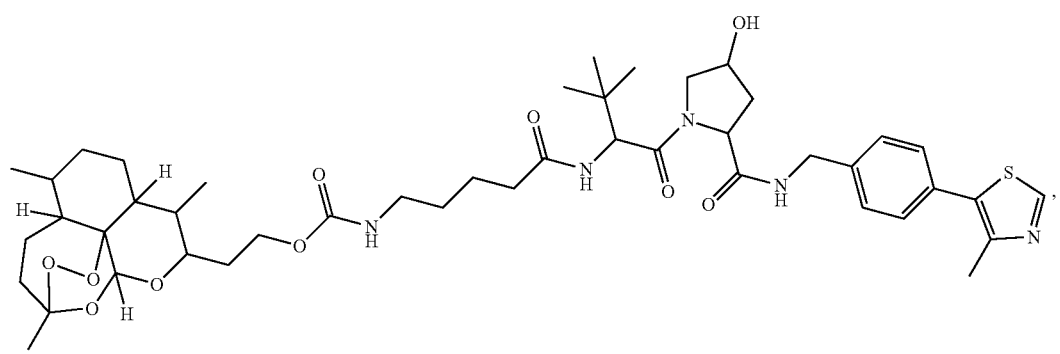
CL-22
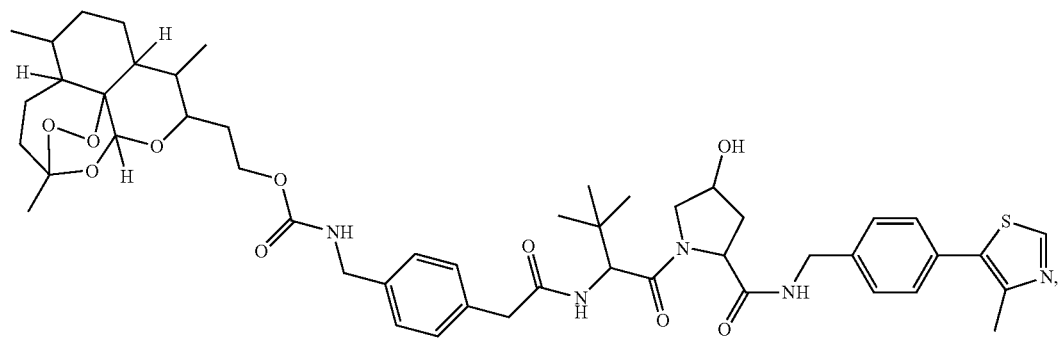
CL-23

-continued
CL-24
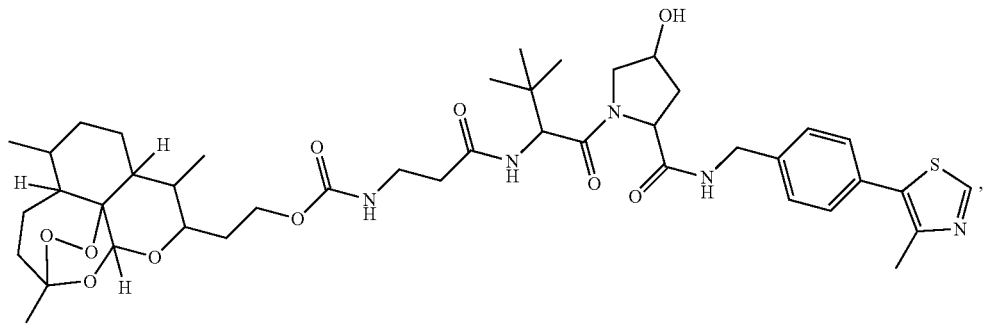
CL-25
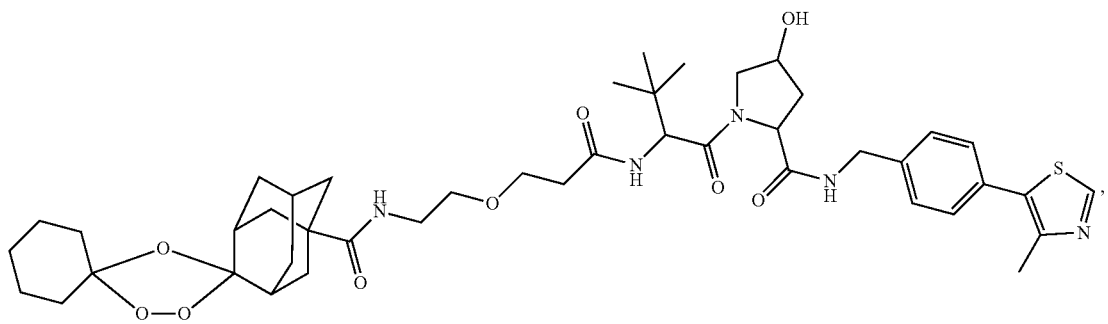
CL-26
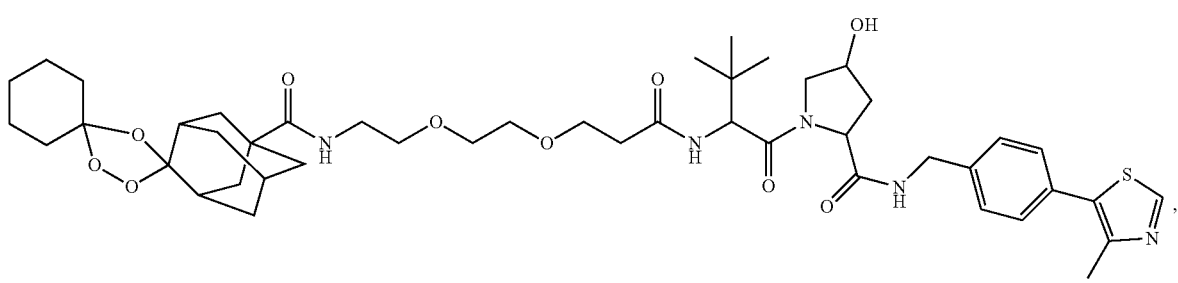
CL-27
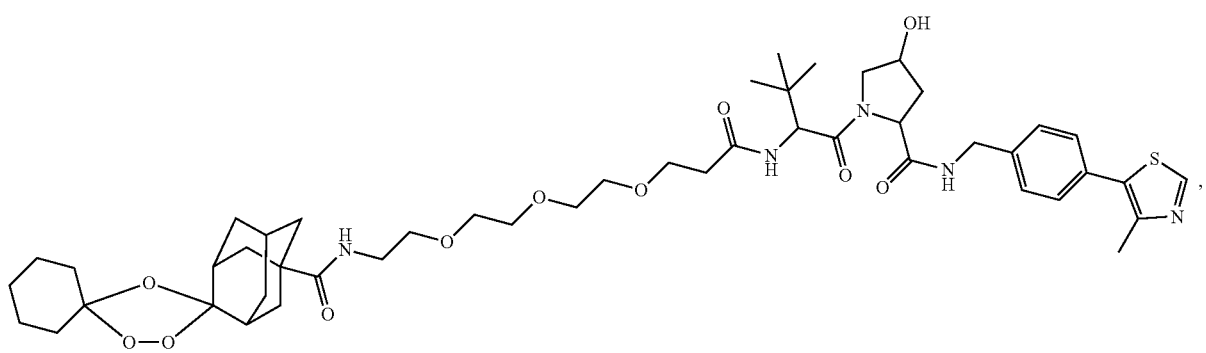
CL-28
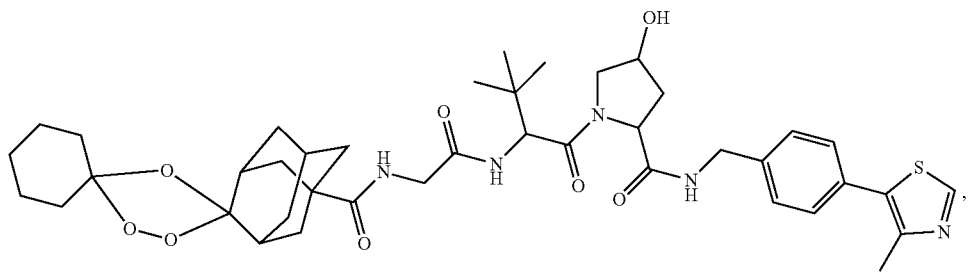

-continued
CL-29
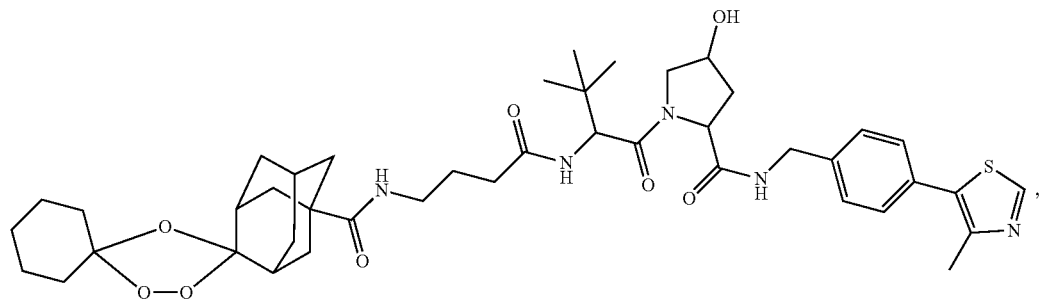
CL-30
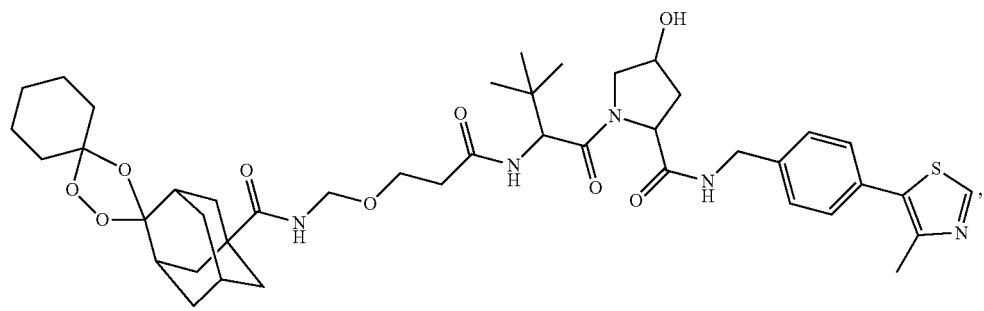
CL-31
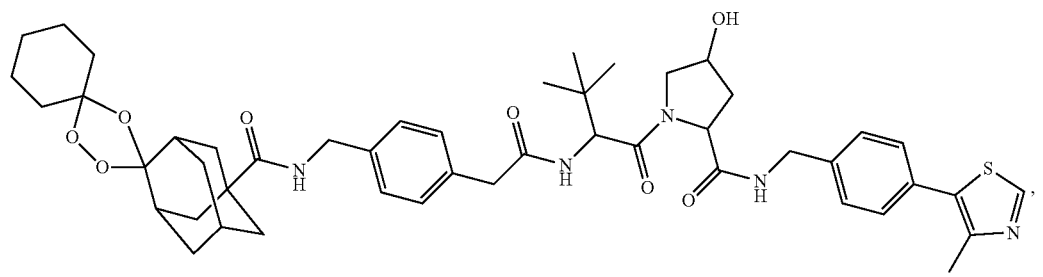
CL-32
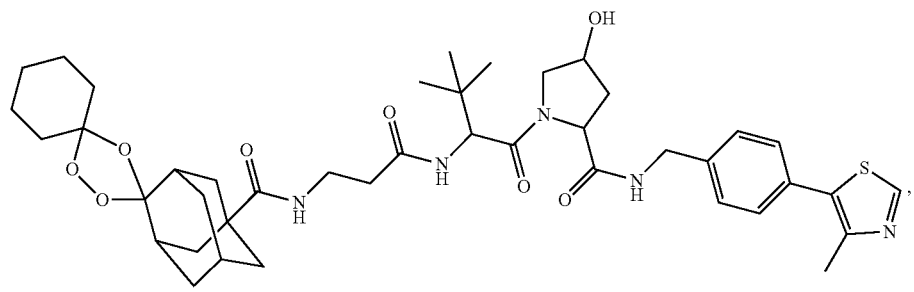
CL-33
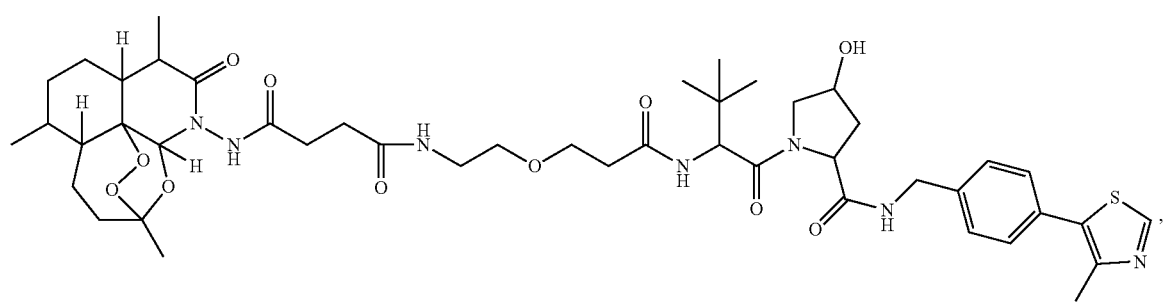

CL-34
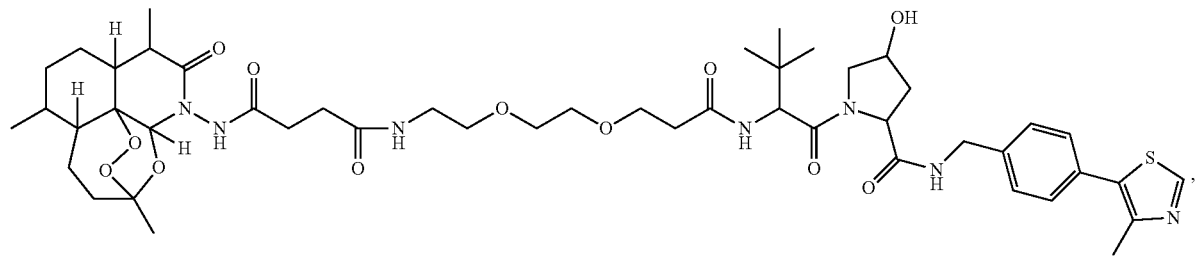
CL-35
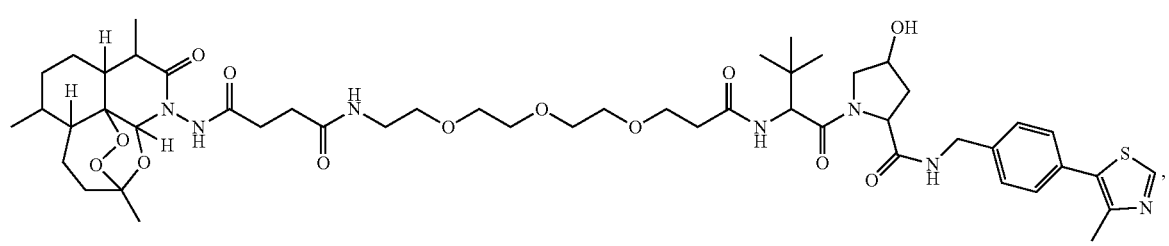
CL-36
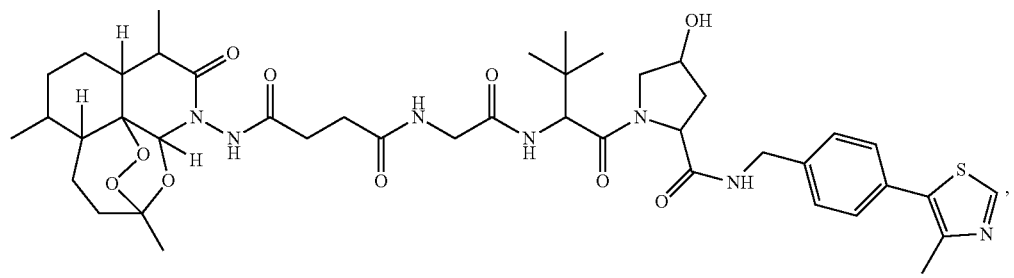
CL-37
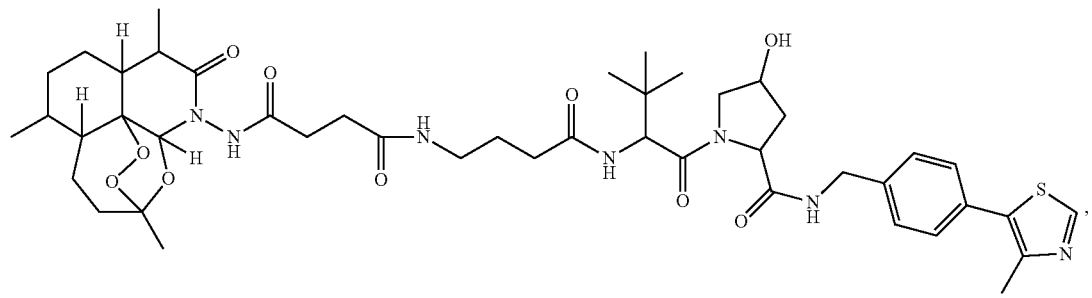
CL-38
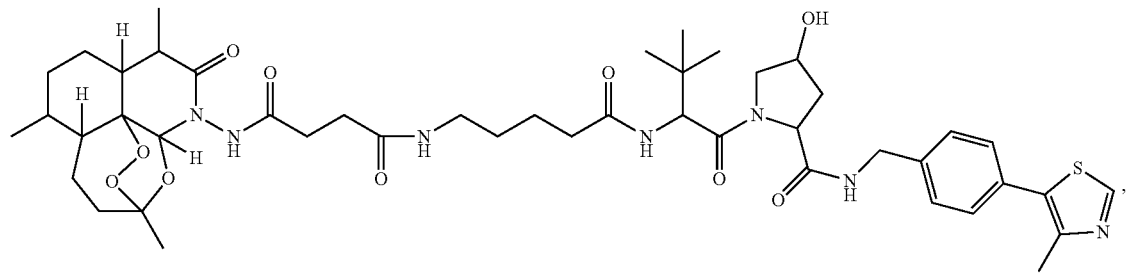

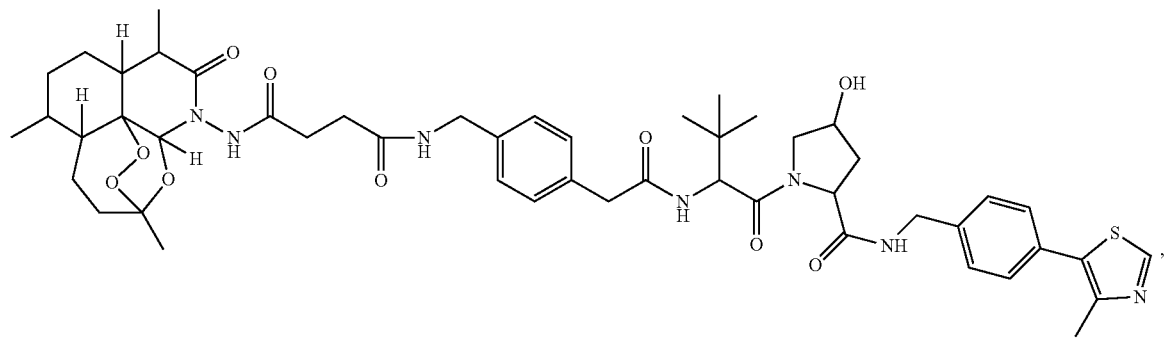
CL-39
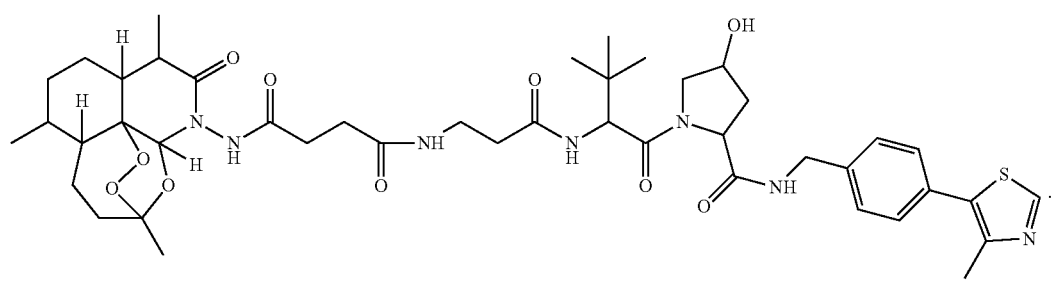
CL-40
The compounds of this invention are most preferably selected from:
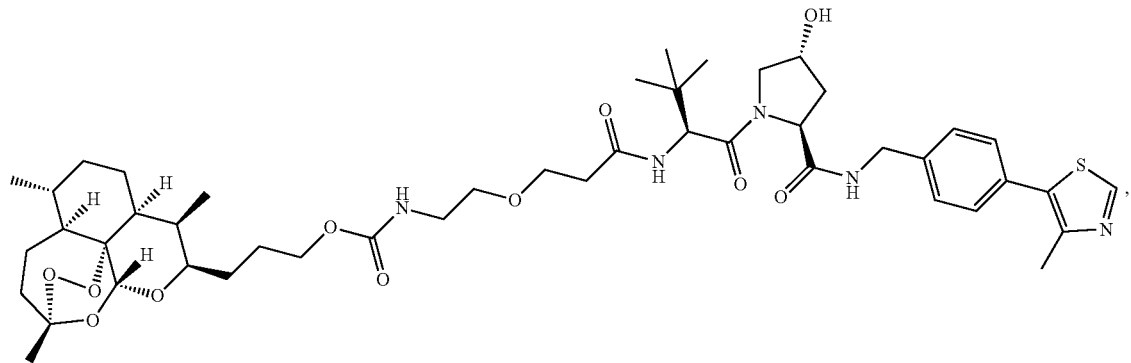
CL-1-T
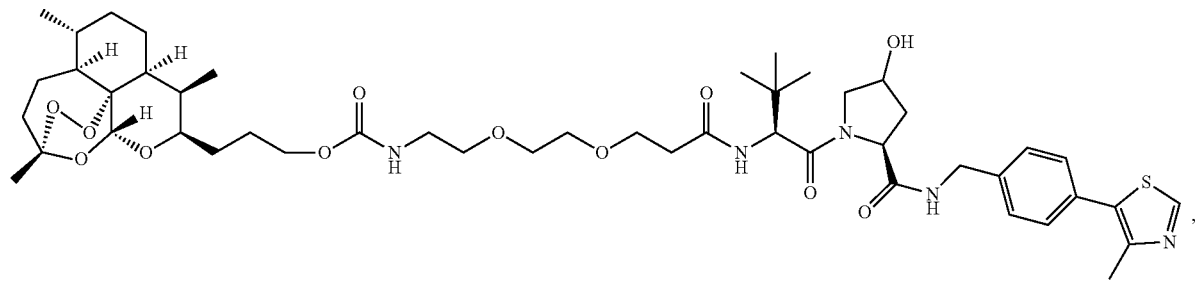
CL-2-T -continued
CL-3-T
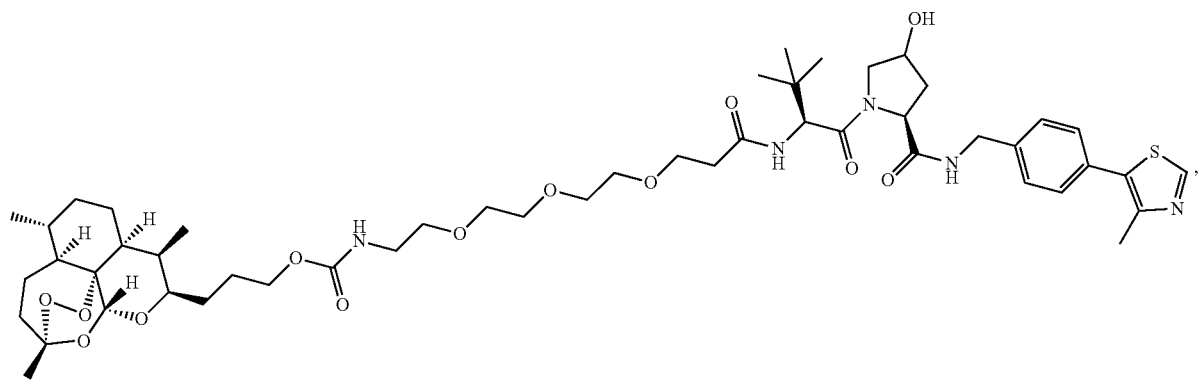
CL-4-T
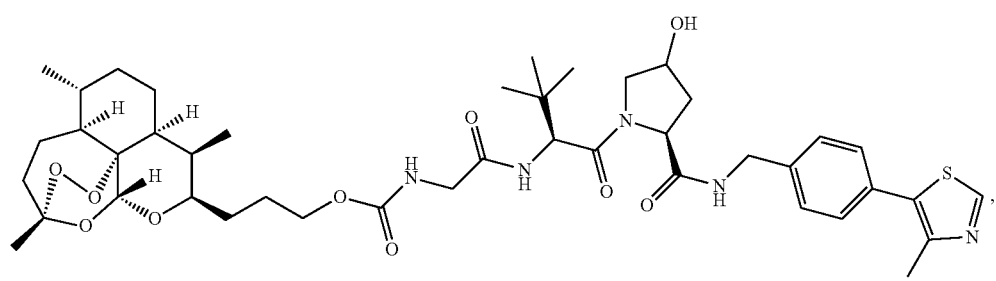
CL-5-T
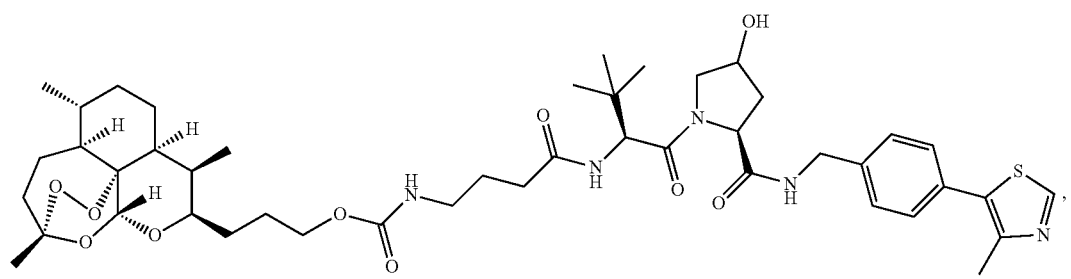
CL-6-T
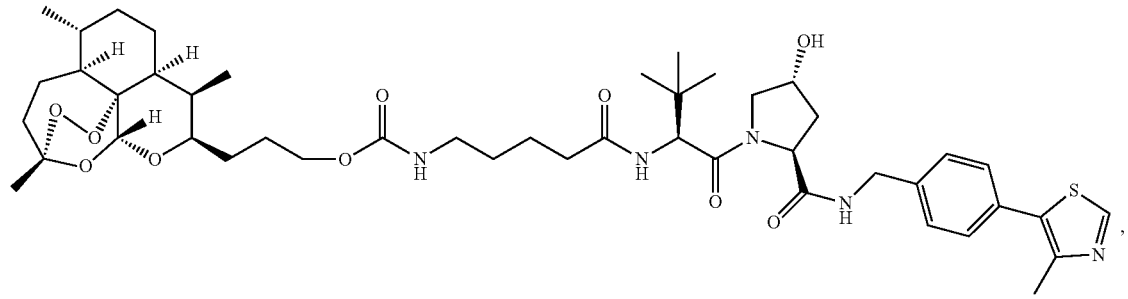
CL-7-T
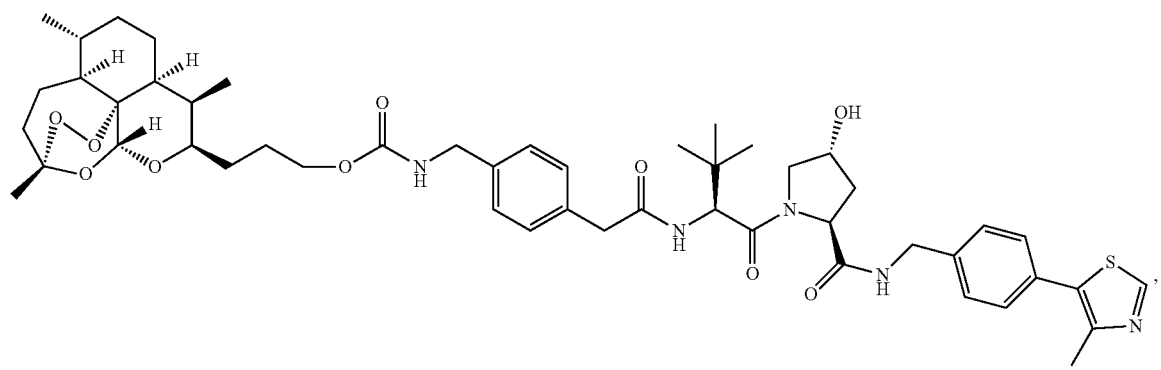

-continued
CL-8-T
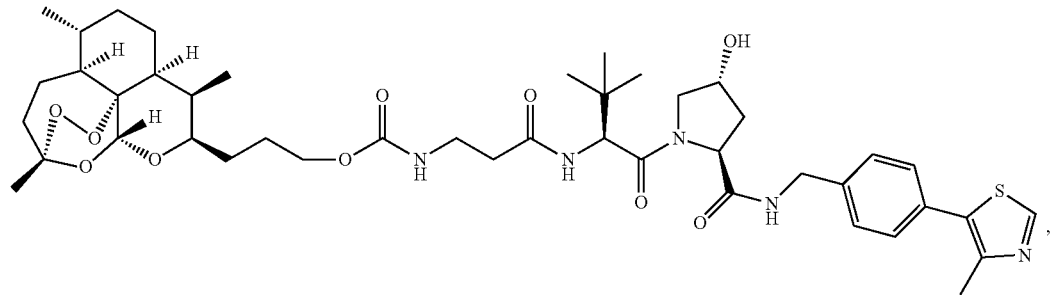
CL-9-T
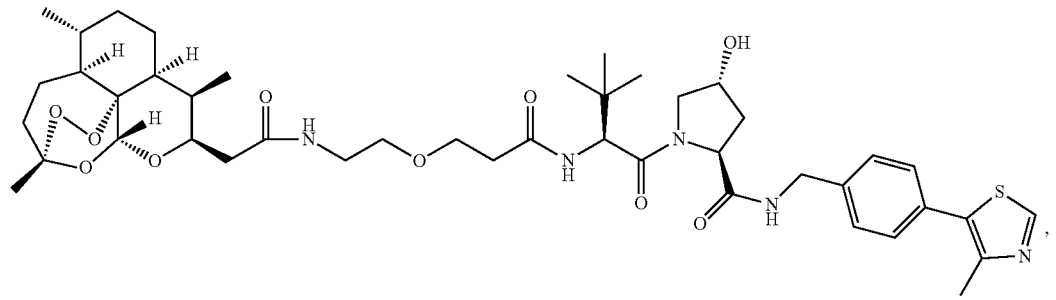
CL-10-T
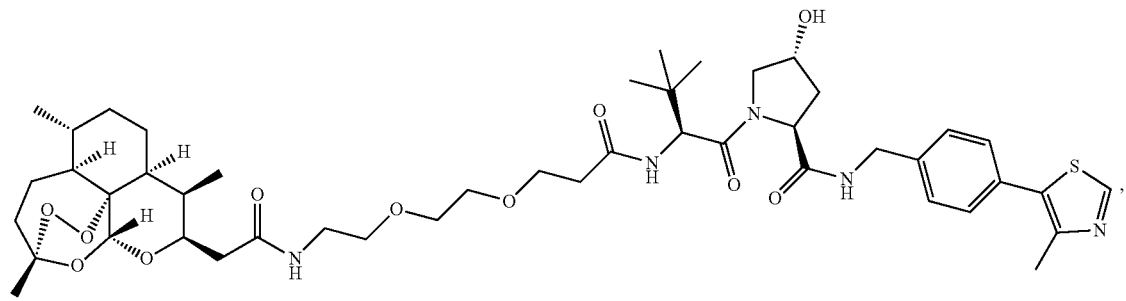
C-11-T
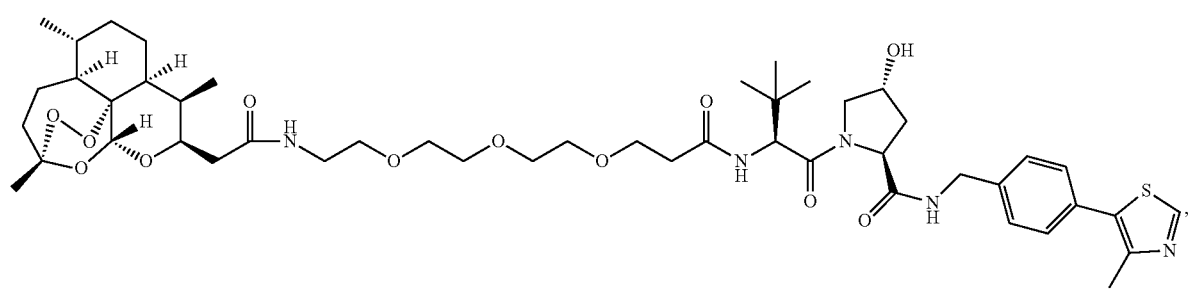
CL-12-T
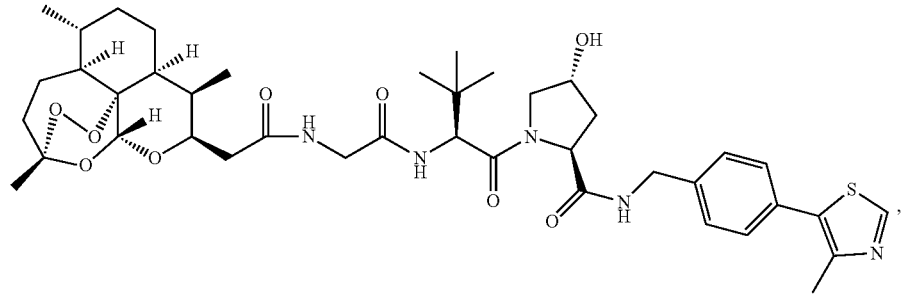

CL-13-T
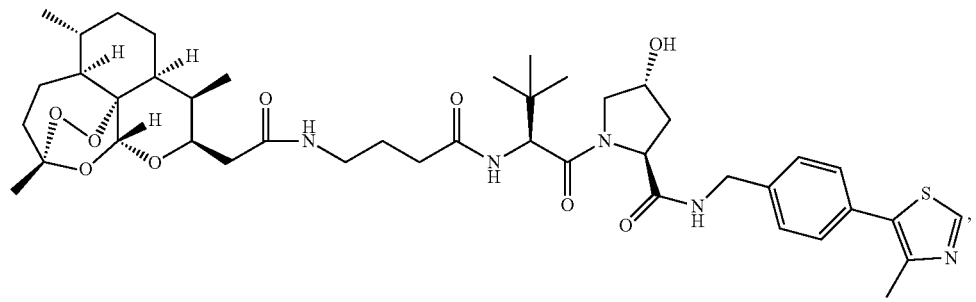
CL-14-T
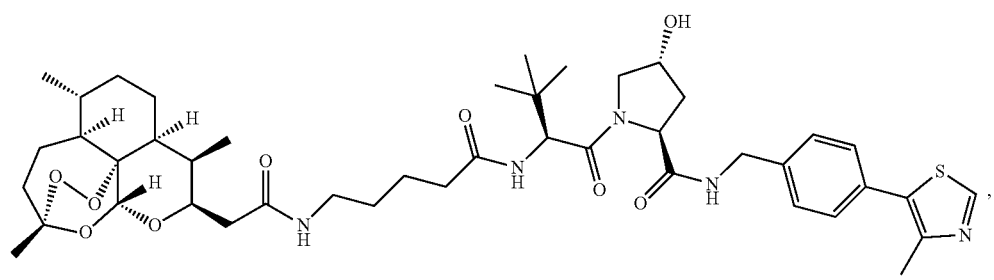
CL-15-T
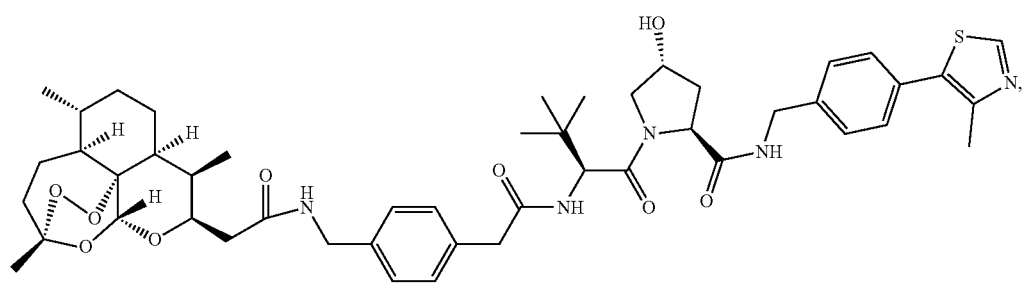
CL-16-T
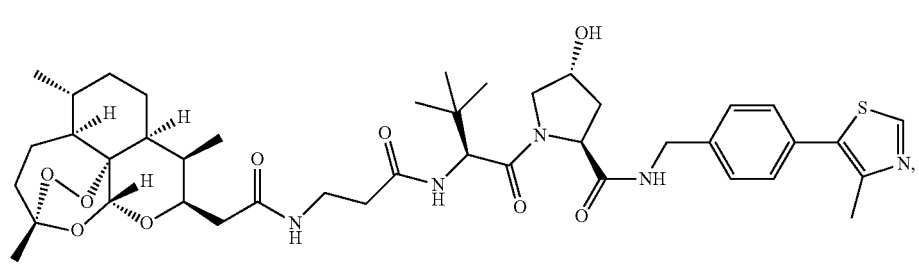
CL-17-T
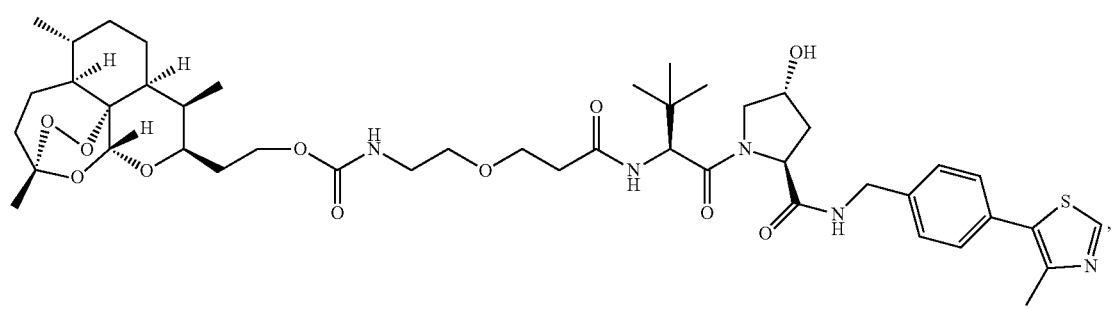

CL-18-T
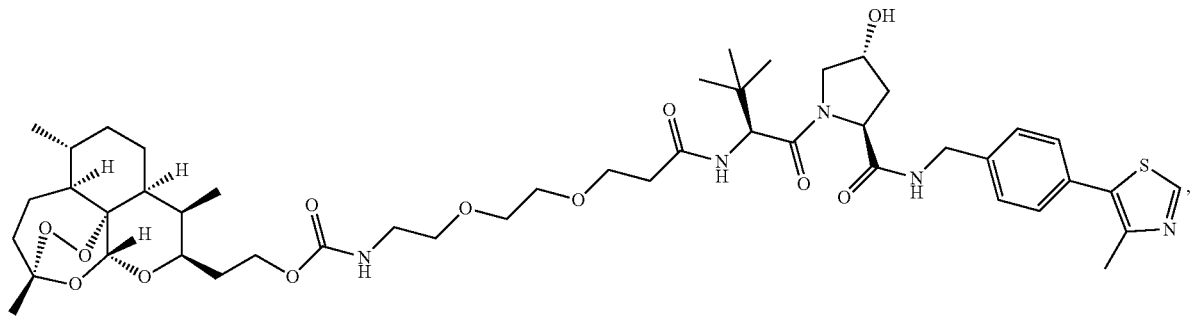
CL-19-T
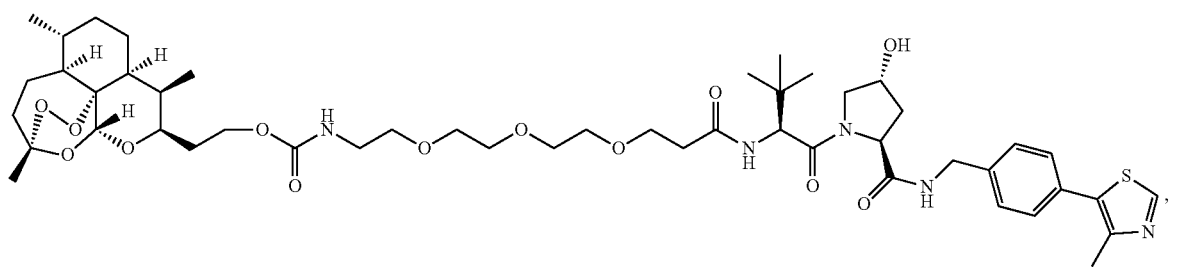
CL-20-T
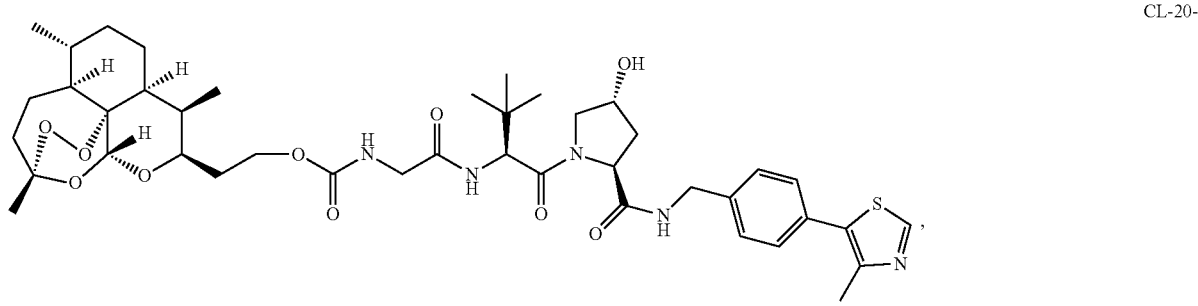
CL-21-T
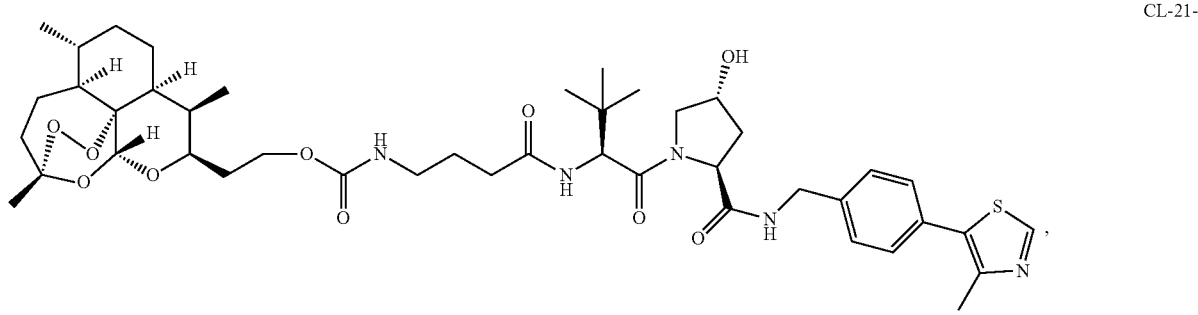
CL-22-T
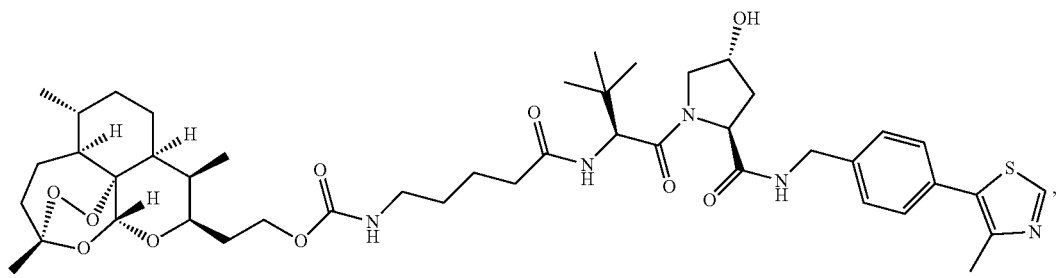

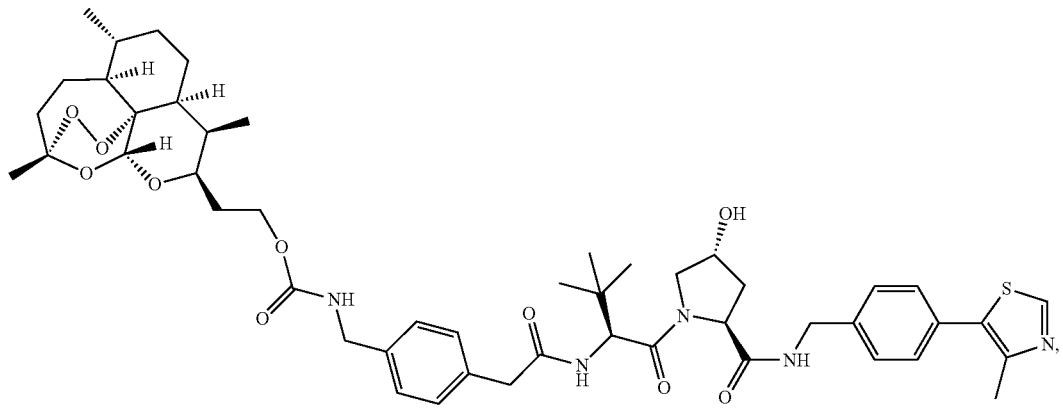

CL-23-T

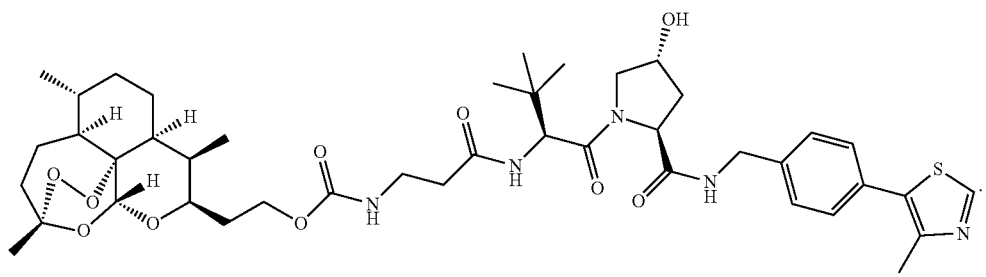

CL-24-T

The second aspect of the technical scheme of the invention provides a group of pharmaceutical compositions, including the compound described in the first aspect of the invention or its pharmaceutically acceptable salt or pharmaceutically acceptable carrier, excipient, diluent, adjuvant, vehicle or their combination; and application of the above compound or pharmaceutically acceptable salt thereof or the composition in the preparation of drugs for the prevention and/or treatment of cancer diseases. According to the invention, pharmaceutically acceptable salts include addition salts formed with the following acids: hydrochloric acid, hydrobromic acid, sulfuric acid, phosphoric acid, methanesulfonic acid, ethanesulfonic acid, p-toluenesulfonic acid, benzene sulfonic acid, benzene disulfonic acid, acetic acid, propionic acid, lactic acid, trifluoroacetic acid, maleic acid, citric acid, fumaric acid, oxalic acid, tartaric acid, benzoic acid, etc., and similar known acceptable acid salts.

The invention can contain the compositions consisted of functional small molecule described in the first aspect and its pharmaceutically acceptable salt as the active ingredient and a pharmaceutically acceptable excipient to prepare, and a clinically acceptable dosage form thereof. The excipient refers to a diluent, adjuvant or carrier that can be used in the pharmaceutical field. The above dosage forms refer to injections, tablets and capsules which am commonly used in clinic.

The third aspect of this invention is that it provides the anti-tumor application of functional small molecule described in the first aspect and its pharmaceutically acceptable salt, which could be used alone or be in combination with other marketed anti-tumor drugs to prevent or treat cancers. Preferably, said cancers include leukemia and lymphoma.

The fourth aspect of this invention is that it provides synthesis methods to prepare the functional small molecule described in the first aspect and its pharmaceutically acceptable salt.

The synthesis method to prepare the compound of formula (I):

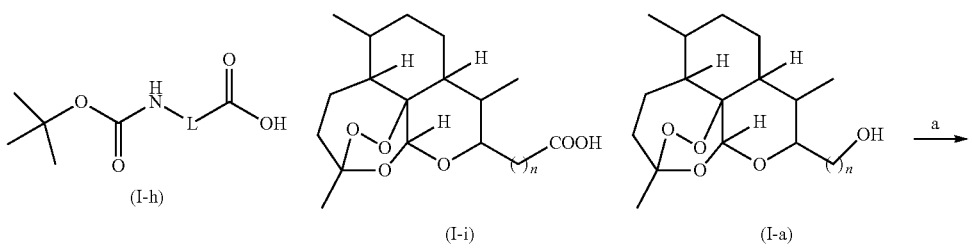

-continued
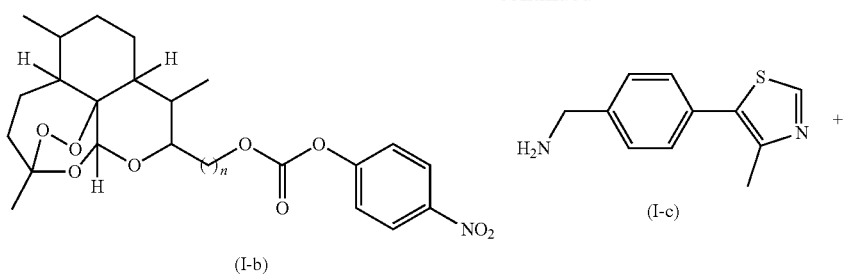
(I-b)    (I-c)
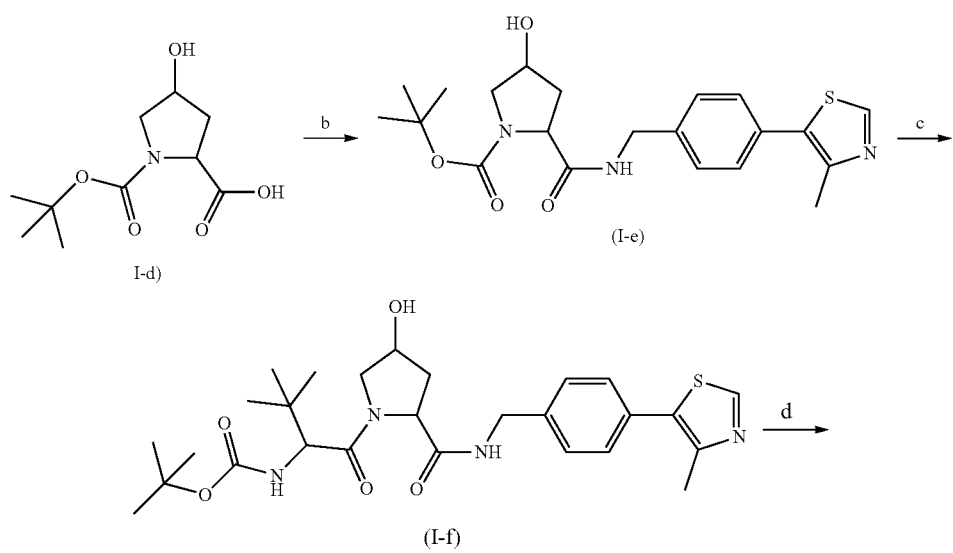
I-d)    (I-e)    (I-f)
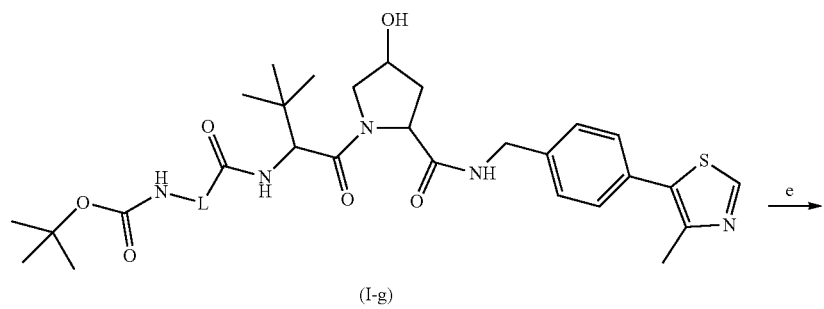
(I-g)
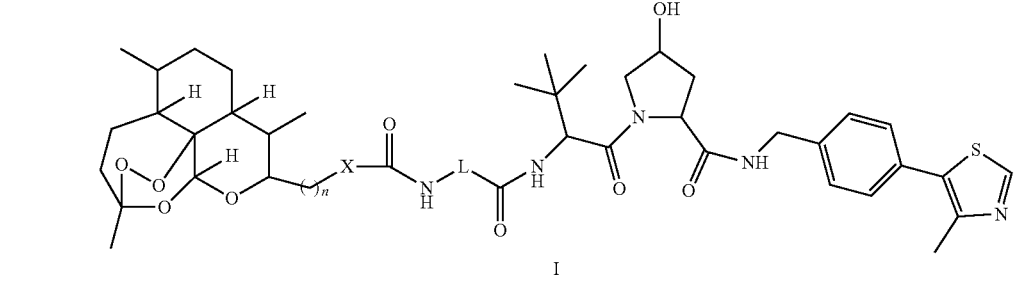
I Step a: the compound I-a reacted with p-nitrobenzoyl chloride to generate compound I-b;
Step b: the compound I-c reacted with compound I-d to generate compound I-e;
Step c: the compound I-e was treated with trifluoroacetic acid to remove the Boc group, followed by the reaction with N-Boc-L-t-Leucine to give compound I-f;
Step d: the compound I-f was treated with trifluoroacetic acid to remove the Boc group, followed by the reaction with L-containing acid to give compound I-g;
Step e: the compound I-g was treated with trifluoroacetic acid to remove the Boc group, followed by the reaction with I-b or I-i to give the compound of formula (I).

The synthesis method to prepare the compound of formula (II):

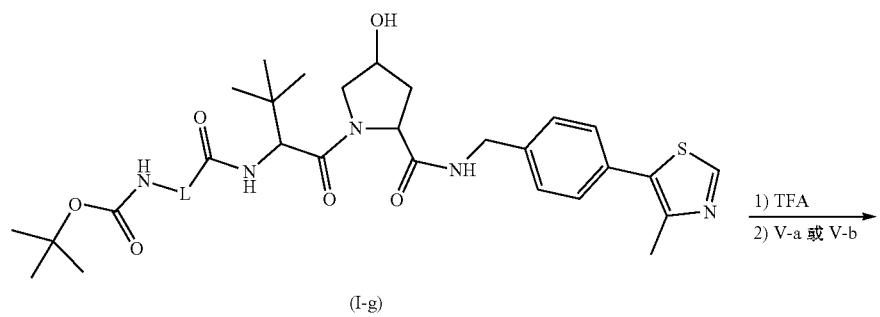

(I-g)

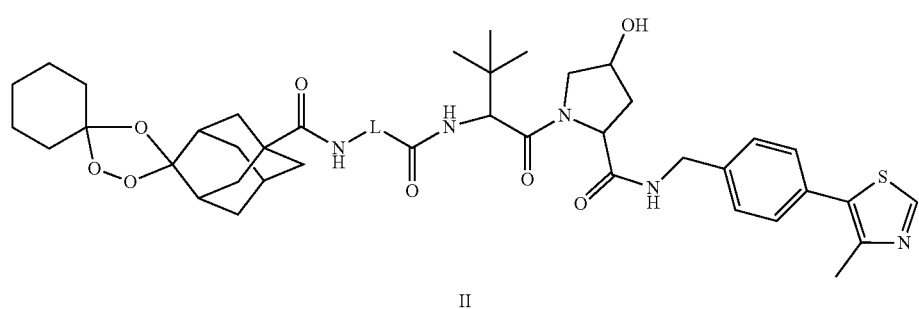

II

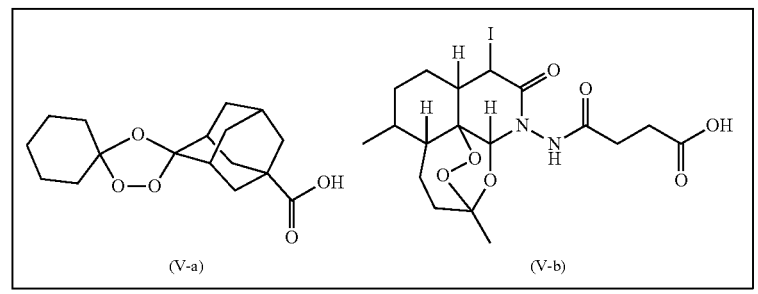

(V-a)  (V-b)

Step: the compound I-g was treated with trifluoroacetic acid to remove the Boc group, followed by the reaction with V-a or V-b to give the compound of formula (II).

Utility

The compounds of this invention could target protein targets including the key proteins in the UPP system, and provide unique method to prevent and treat cancer.

ATTACHED FIGURES

FIG. 1 The proportion of human leukemia cells in peripheral blood of mice. QHS: artesunate; QV: example CL-8.

Figure 2:
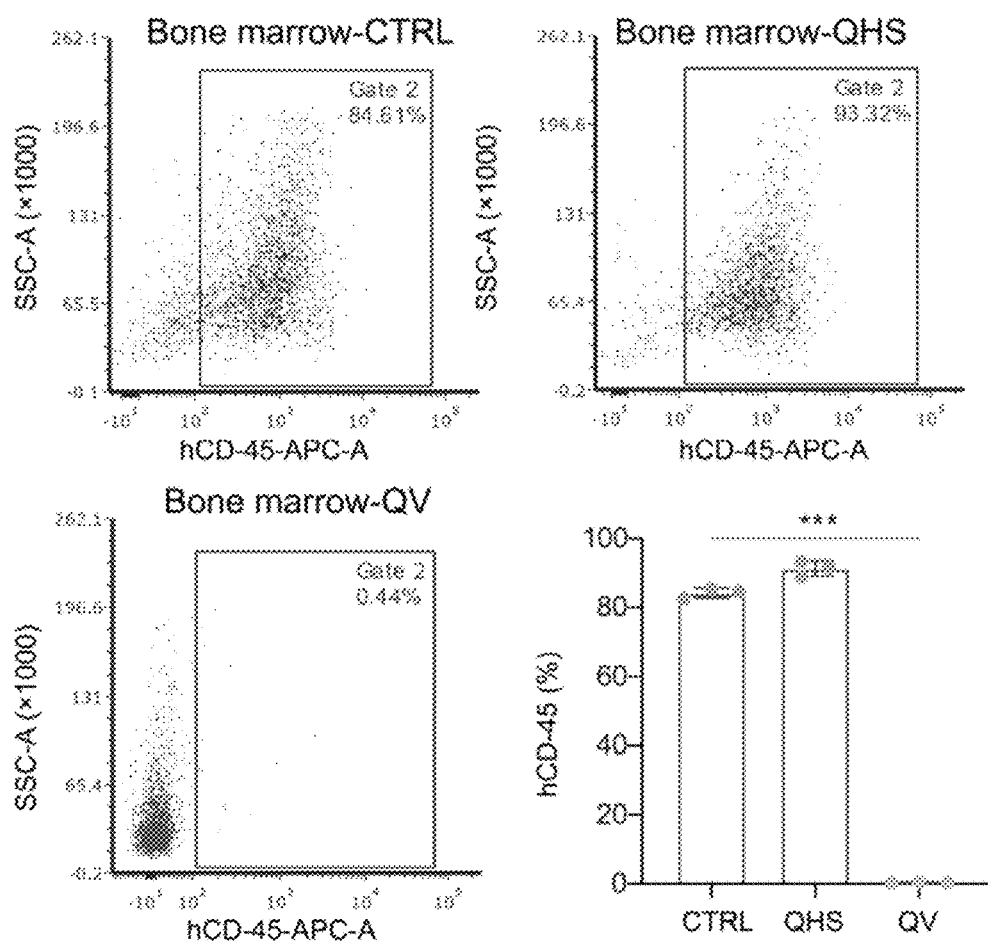

FIG. 2 The proportion of human leukemia cells in bone marrow of mice. QHS: artesunate; QV: example CL-8.

Figure 3:
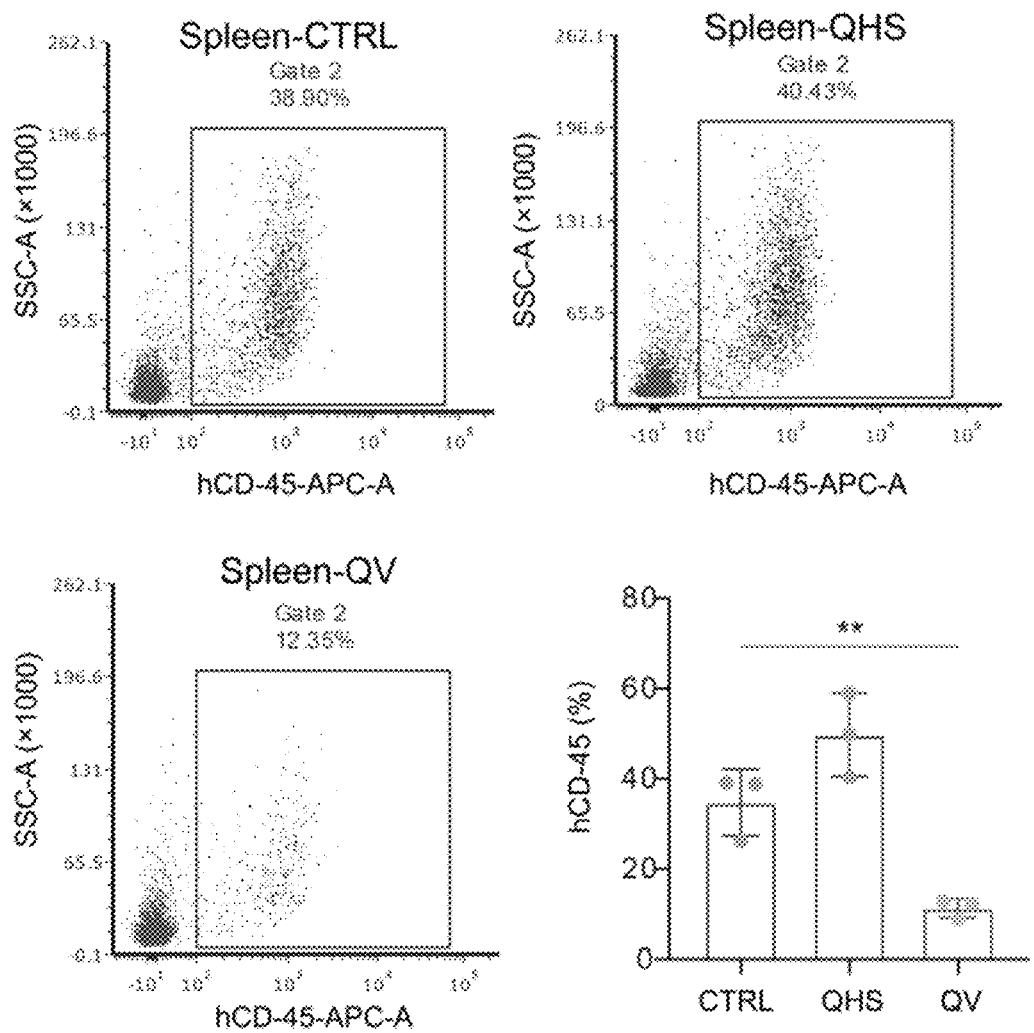

FIG. 3 The proportion of human leukemia cells in spleen of mice. QHS: artesunate; QV: example CL-8.

Figure 4:
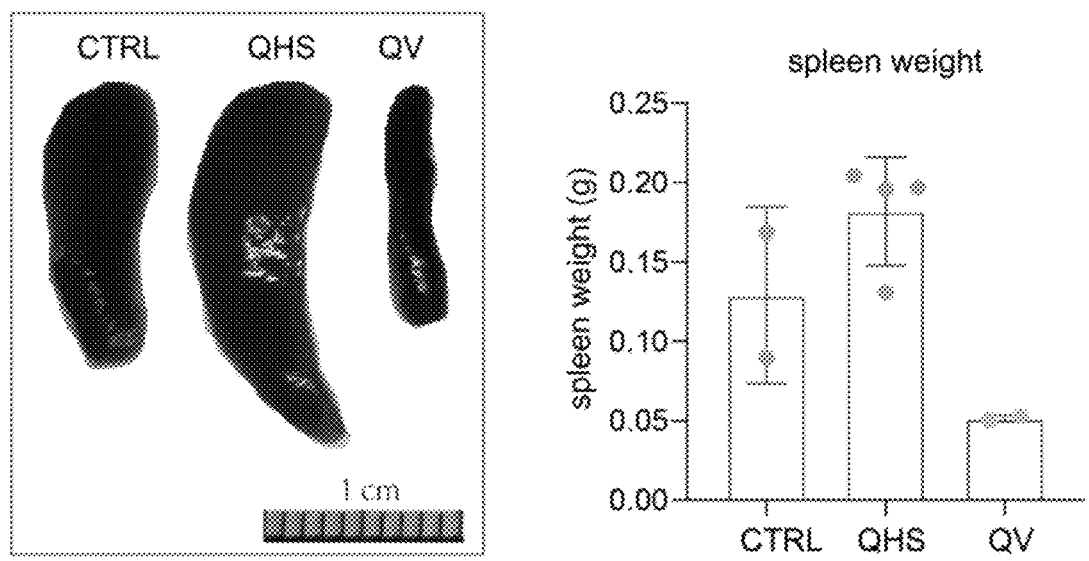

FIG. 4 The weight of spleen of mice. QHS: artesunate; QV: example CL-8; cm: centimeter.

FIG. 5 The $^1$H-NMR spectrum of key intermediate 1.

FIG. 6 The mass spectrum of key intermediate 1. ES-API Positive: ES-API signal of positive ion.

Figure 7:
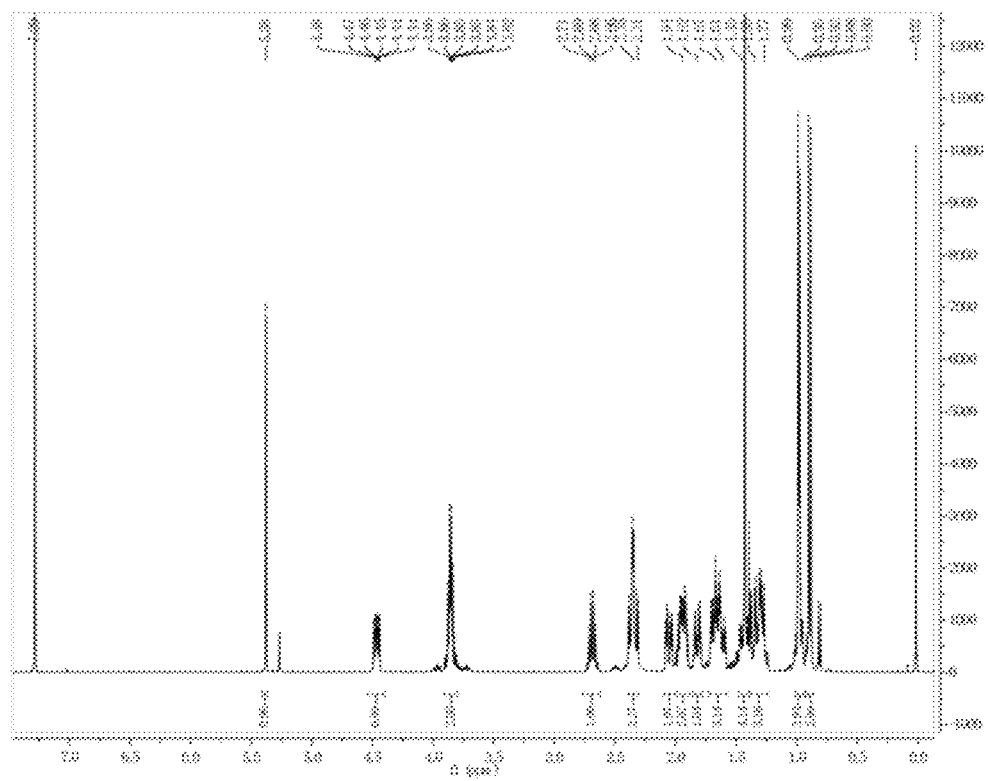

FIG. 7 The $^1$H-NMR spectrum of key intermediate 2.

Figure 8:
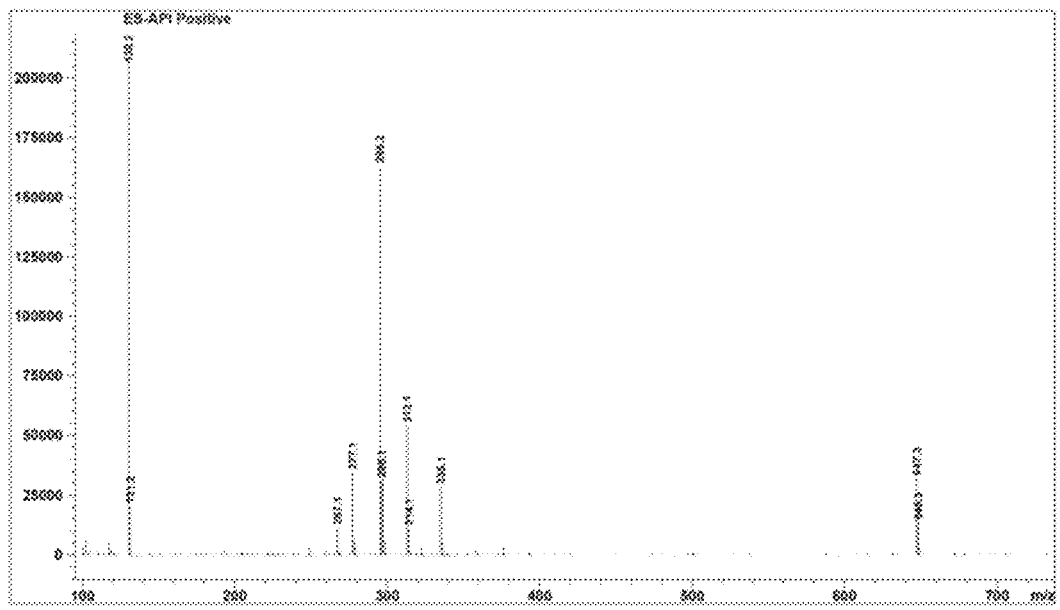

FIG. 8 The mass spectrum of key intermediate 2. ES-API Positive: ES-API signal of positive ion.

Figure 9:
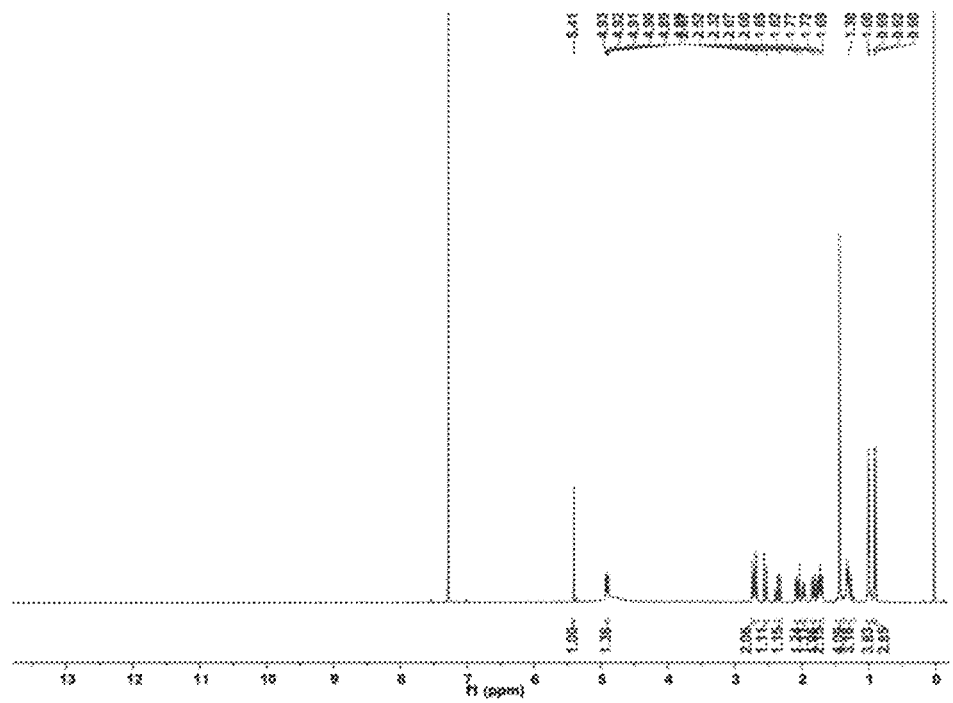

FIG. 9 The $^1$H-NMR spectrum of key intermediate 3.

Figure 10:
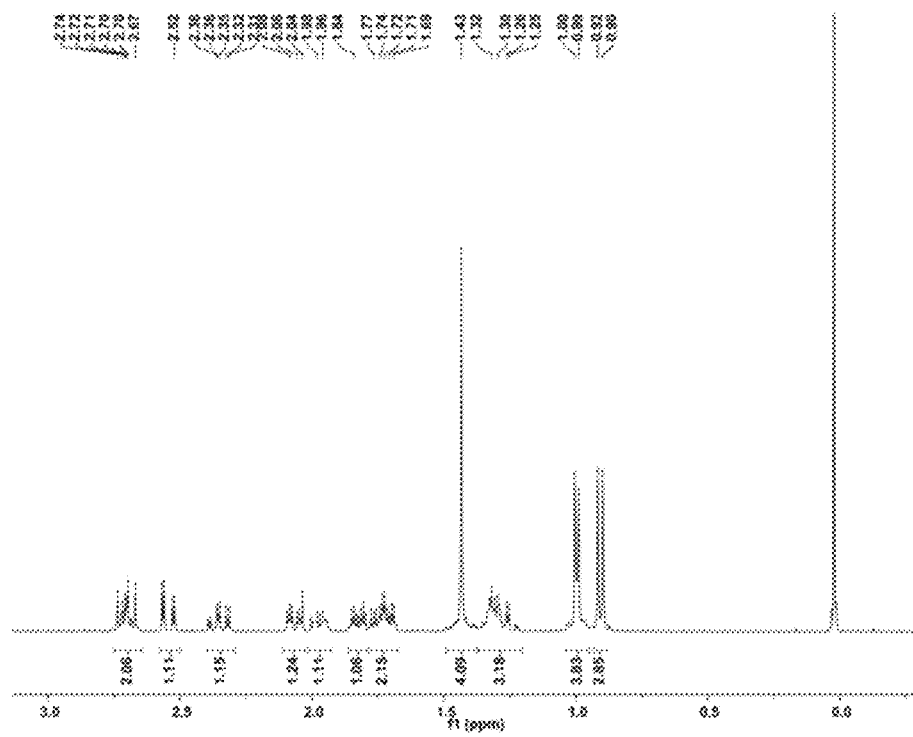

FIG. 10 The partial enlarged view of $^1$H-NMR spectrum of key intermediate 3.

Figure 11:
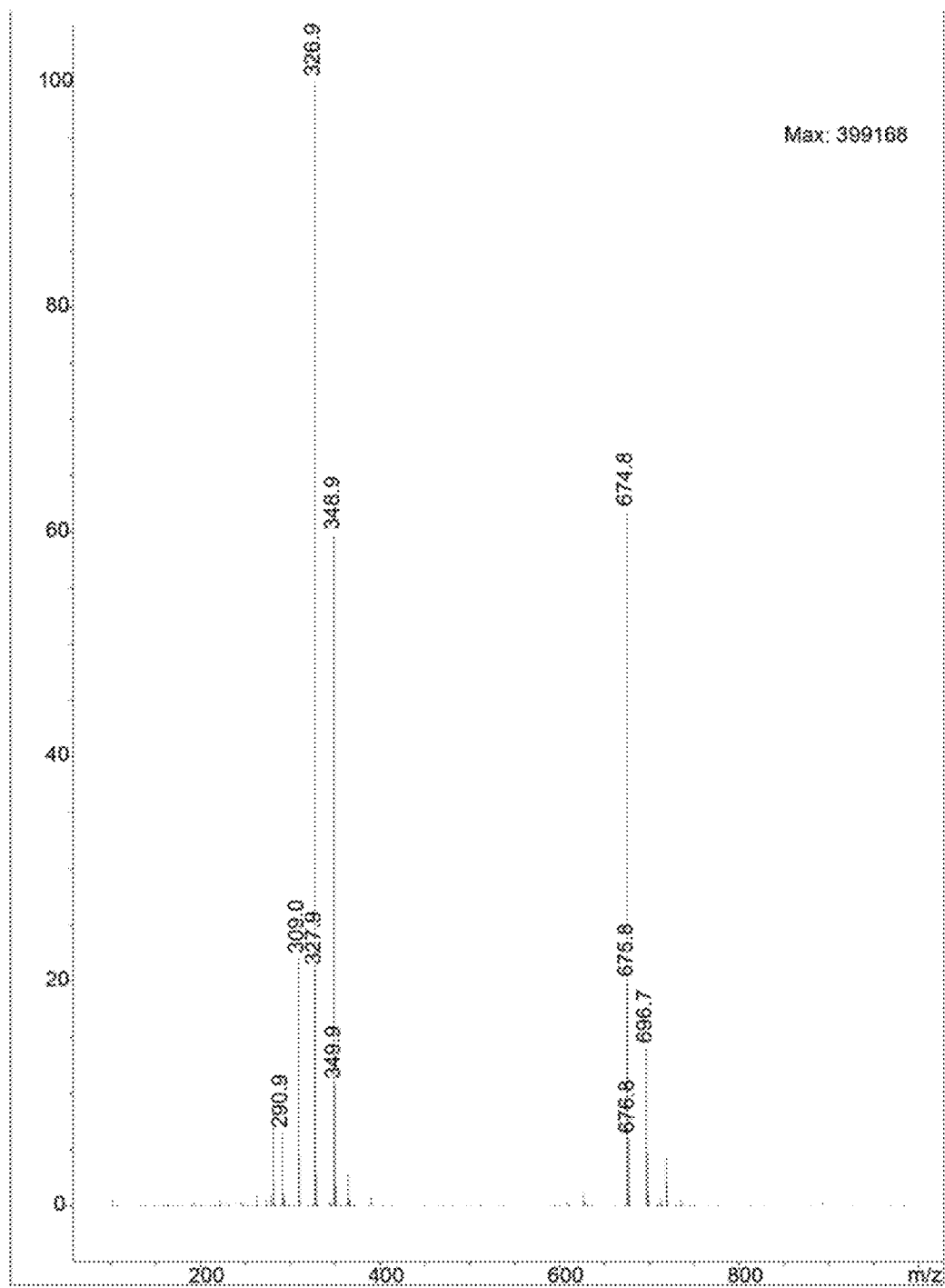

FIG. 11 The mass spectrum of key intermediate 3.

SPECIFIC EMBODIMENT

Without further detailed description, it is considered that those skilled in the field of the invention can make maximum use of the invention with the help of the above description. Therefore, the examples below am intended to be purely exemplary and should not be considered to be limiting in any way.

Reagents were purchased from commercial suppliers, or prepared according to the known method in the field of this invention, or prepared according to the methods in this invention.

The structures of compounds were verified through high-resolution mass spectra (HRMS). HRMS analysis was performed on a Thermo FisherExactive Plus (ThermoFisher Scientific). Silica gel (200-300 mesh, Yantai Yinlong Chemical Factory, China) were used for column chromatography.

The intermediate 1, intermediate 2 and intermediate 3 were obtained through the entrusted commercial supply, which were synthesized by Bioduro (Beijing) according to the classical derivation method to modify artemisinin (*Org. Lett.* 2005, 7, 1561-1564; *Org. Lett.* 2010, 12, 1420-1423; *Boorg. Med. Chem.* 2009, 17, 1325-1338; *J. Med. Chem.* 2002, 45, 1052-1063). All the intermediates were verified through ¹HNMR and mass spectra (attached FIGS. 5-10).

intermediate 1

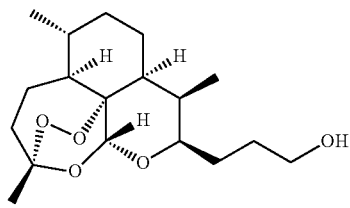

intermediate 2

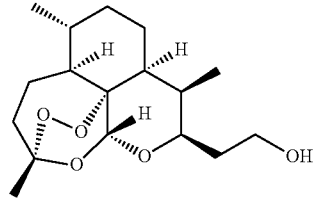

intermediate 3

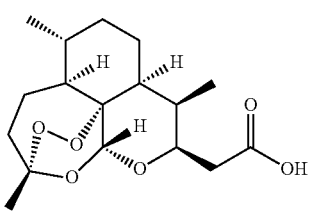

The below two unnatural amino acids were obtained through commercial suppliers.

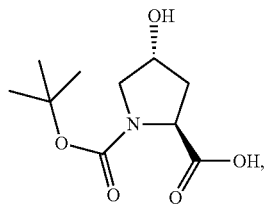

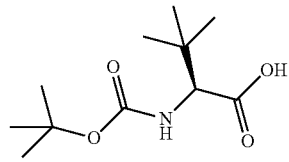

Example 1: The preparation of compound CL-1. The chemical structure of CL-1 is shown as follows.

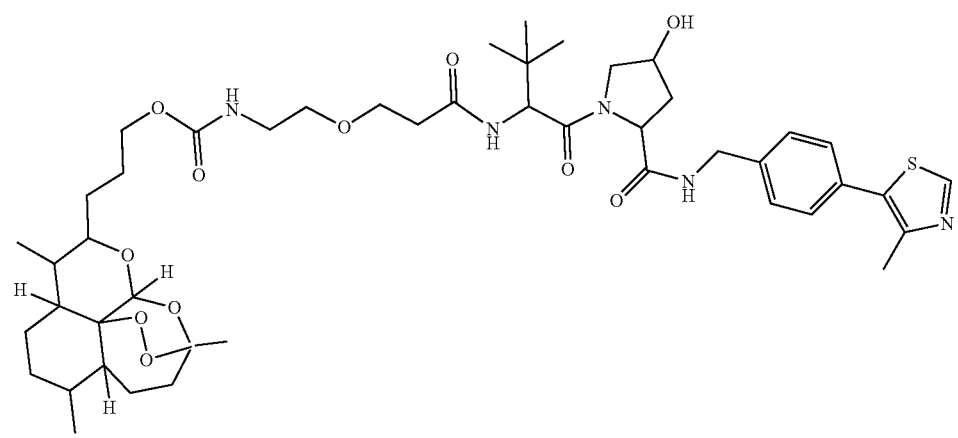

Step 1) the Preparation of Compound I-b-3.

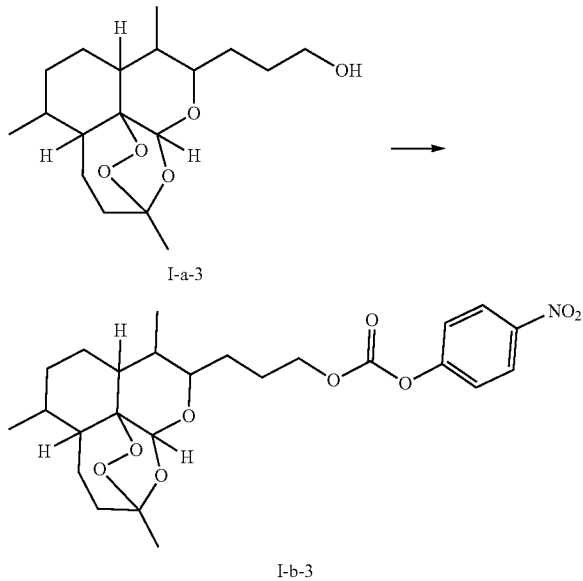

The compound I-a-3 (intermediate 1, 240 mg, 0.74 mmol, 1 eq) was dissolved in dichloromethane (10 mL). The solution was placed under ice-water bath, followed by addition of p-nitrophenyl chloroformate (180 mg, 0.90 mmol, 1.2 eq.) and pyridine (183 lL, 2.28 mmol, 3 eq.). The ice-water bath was removed and the mixture was stirred at room temperature. Nine hours later, the reaction was quenched by addition of water (10 mL). The organic phase was taken, washed by saturated ammonium chloride aqueous solution (50 mL×2) and brine, dried over sodium sulphate, and filtered. The filtrate was concentrated and purified with silica gel chromatography (elution condition: petroleum ether/ethyl acetate=30/1-5/1) to obtain I-b-3 as colorless oil (300 mg, 82.5%).

Step 2) the Preparation of Compound I-e.

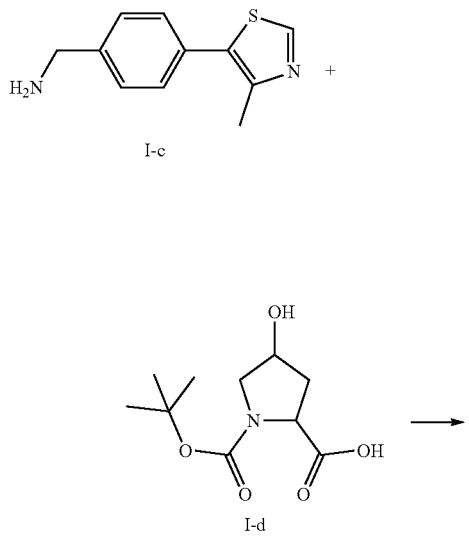

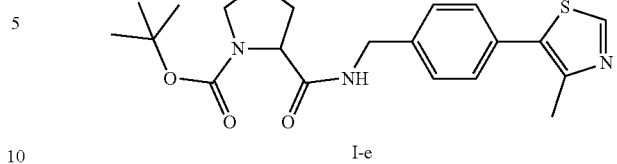

(4-(4-methylthiazol-5-yl)phenyl)methanamine (I-c, 3 g, 14.58 mmol, 1 eq.) was dissolved in dichloromethane, followed by addition of 1-(tert-butoxycarbonyl)-4-hydroxy-pyrrolidine-2-carboxylic acid (3.39 g, 14.58 mmol, 1 eq.) and HATU (4.96 g, 16.08 mmol, 1.1 eq.). Finally, N,N-diisopropylethylamine (DIPEA, 1.70 ml, 9.72 mmol, 4 eq.) was added to the above mixture. The mixture was stirred at room temperature for 4 hours. Then the reaction solution was washed with saturated ammonium chloride aqueous solution and brine. The combined organic phase was dried over sodium sulphate, condensed under vacuum. The desired residue was purified with silica gel chromatography (elution condition: dichloromethane-dichloromethane/methanol=1/20) to give the product I-e as yellow solid (3.97 g, 65.24%).

Step 3) the Preparation of Compound I-f.

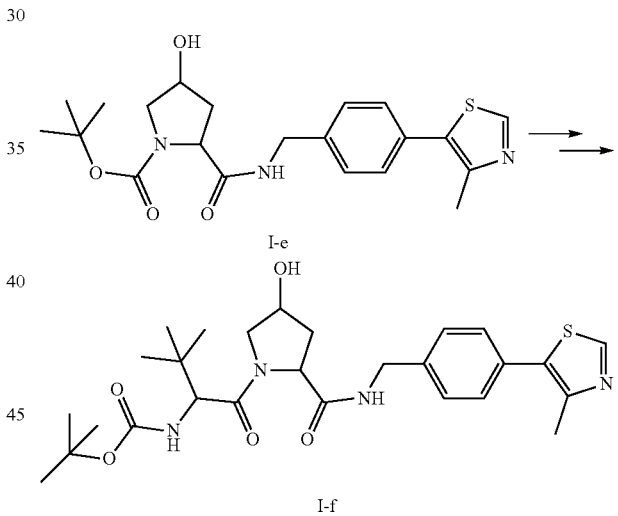

The compound I-e (3.97 g, 9.51 mmol, 1 eq.) was dissolved in the mixed solvent of dichloromethane and trifluoroacetic acid (the proportion of trifluoroacetic acid was 20%). The mixture was stirred for 2 hour to remove the Boc group of I-e. The solvents were then removed under vacuum. The desired residue was dissolved in dichloromethane (200 mL), followed by addition of 2-((tert-butoxycarbonyl)amino)-3,3-dimethylbutanoic acid (2.64 g, 11.41 mmol, 1.2 eq.) and HATU (5.43 g, 14.27 mmol, 1.5 eq.). Finally, N,N-diisopropylethylamine (DIPEA, 6.29 ml, 38.04 mmol, 4 eq.) was added to the above mixture to make the pH>9. The mixture was stirred at room temperature for 2 hours. After the reaction completed, the reaction mixture was washed with saturated ammonium chloride aqueous solution (200 mL×2) and brine (200 mL). The combined organic phase was dried over sodium sulphate and filtered. The filtrate was concentrated under vacuum. The desired residue was purified with silica gel chromatography ((elution condition: dichloromethane-dichloromethane/methanol=97.5/2.5) to give the product I-f as yellow solid (3.45 g, 68.32%).

Step 4) the Preparation of Compound I-g-L1.

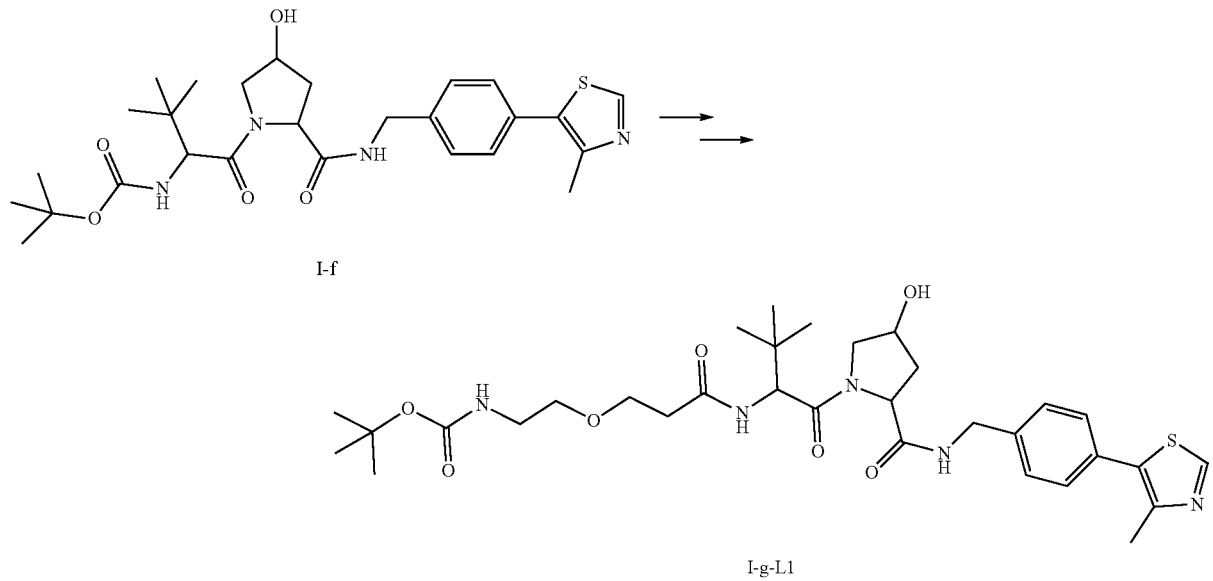

I-f

I-g-L1

The compound I-f (190 mg, 0.36 mmol, 1 eq.) was dissolved in the mixed solvent of dichloromethane and trifluoroacetic acid (the proportion of trifluoroacetic acid was 20%). The mixture was stirred for 2 hour to remove the Boc group of I-e. The solvents were then removed under vacuum. The desired residue was dissolved in dichloromethane (5 mL), followed by addition of 3-(2-((tert-butoxycarbonyl)amino)ethoxy)propanoic acid (83.5 mg, 0.38 mmol, 1.2 eq.) and HATU (163.3 mg, 0.43 mmol, 1.2 eq.). Finally, N,N-diisopropylethylamine was added to the above mixture to make the pH>9. The mixture was stirred at room temperature for 2 hours. After the reaction completed, the reaction mixture was washed with saturated ammonium chloride aqueous solution (20 mL×2) and brine (20 mL). The combined organic phase was dried over sodium sulphate and filtered. The filtrate was concentrated under vacuum. The desired residue was purified with silica gel chromatography ((elution condition: dichloromethane-dichloromethane/methanol=95/5) to give the product I-g-L1 as yellow solid (166 mg, 71.9%).

Step 5) the Preparation of CL-1

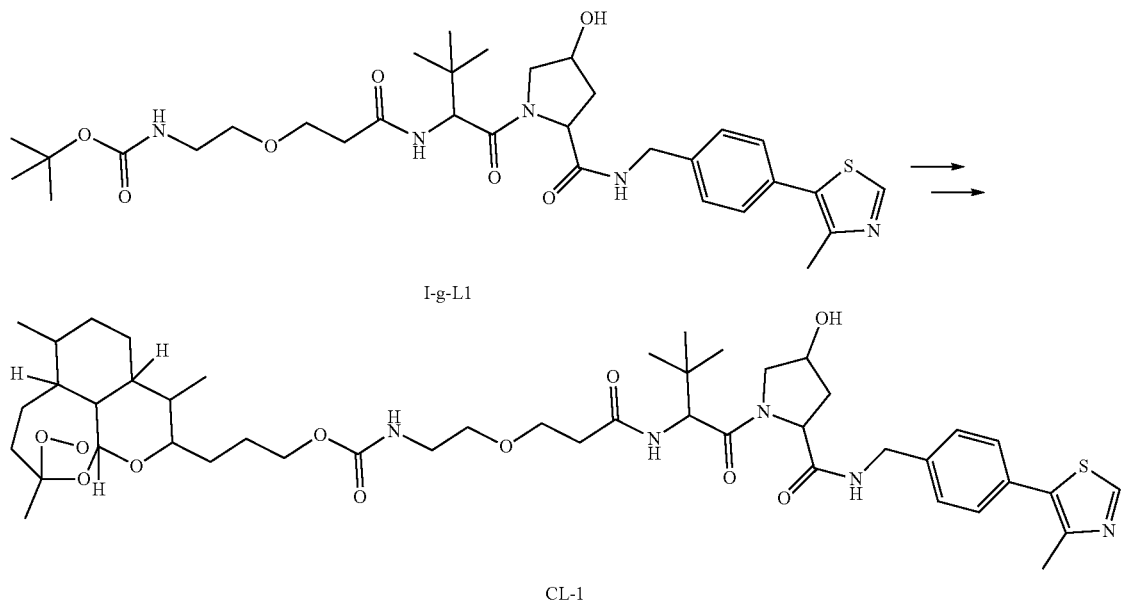

I-g-L1

CL-1

The compound I-g-L1 (The L part of I-g is L1, 30 mg, 0.046 mmol, 1 eq.) was dissolved in the mixed solvent of dichloromethane and trifluoroacetic acid (the proportion of trifluoroacetic acid was 20%). The mixture was stirred for 2 hour to remove the Boc group of I-e. The solvents were then removed under vacuum. The desired residue was dissolved in dichloromethane (5 mL), followed by addition of I-b-3 (I-b (n=3), 23 mg, 0.046 mmol, 1 eq.). Finally, N,N-diisopropylethylamine was added to the above mixture to make the pH>9. The mixture was stirred at room temperature for 2 hours. After the reaction completed, the reaction mixture was washed with saturated ammonium chloride aqueous solution (20 mL×2) and brine (20 mL). The combined organic phase was dried over sodium sulphate and filtered. The filtrate was concentrated under vacuum. The desired residue was purified with prepared HPLC to give the product CL-1 as white solid (32 mg, 81.6%). HRESI-MS m/z: 898.4650 [M+H]$^+$ (calcd 898.4631 for C46H68N5O11S).

Example 2: The preparation of compound CL-2. The chemical structure of CL-2 is shown as follows.

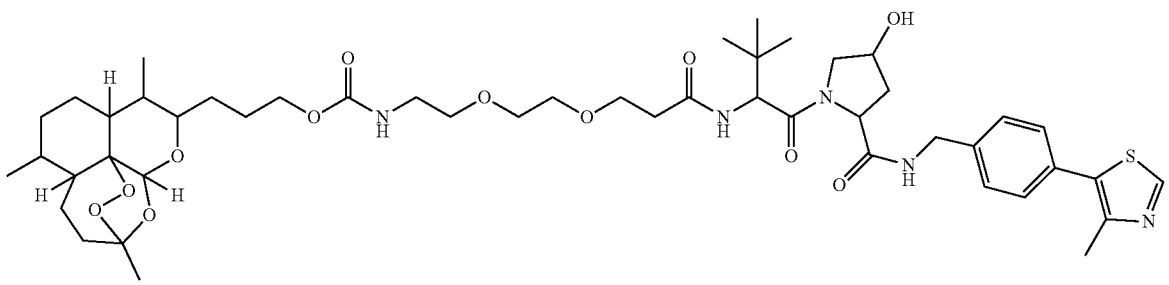 [SMILES: Cc1ncsc1-c1ccc(CNC(=O)C2CC(O)CN2C(=O)C(NC(=O)CCOCCOCCNC(=O)OCCCC2OC3OC4(C)CCC5C(C)CCC(C2C)C35OO4)C(C)(C)C)cc1]

By using I-g-L2 (The L part of I-g is L2) instead of I-g-L1 and following the procedure of CL-1 preparation there is obtained CL-2. HRESI-MS m/z: 942.4867 [M+H]$^+$ (calcd 942.4893 for C48H72N5O12S).

Example 3: The preparation of compound CL-3. The chemical structure of CL-3 is shown as follows.

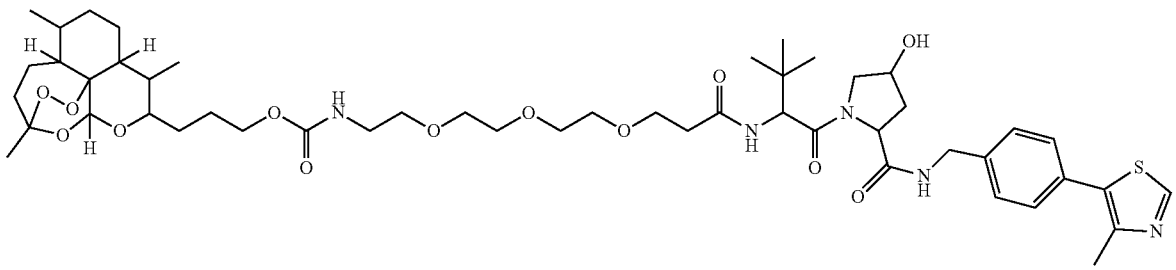 [SMILES: Cc1ncsc1-c1ccc(CNC(=O)C2CC(O)CN2C(=O)C(NC(=O)CCOCCOCCOCCNC(=O)OCCCC2OC3OC4(C)CCC5C(C)CCC(C2C)C35OO4)C(C)(C)C)cc1]

By using I-g-L3 (The L part of I-g is L3) instead of I-g-L1 and following procedure of CL-1 preparation there is obtained CL-3. HRESI-MS m/z: 986.5146 [M+H]$^+$ (calcd 986.5155 for C50H76N5O13S).

Example 4: The preparation of compound CL-4. The chemical structure of CL-4 is shown as follows.

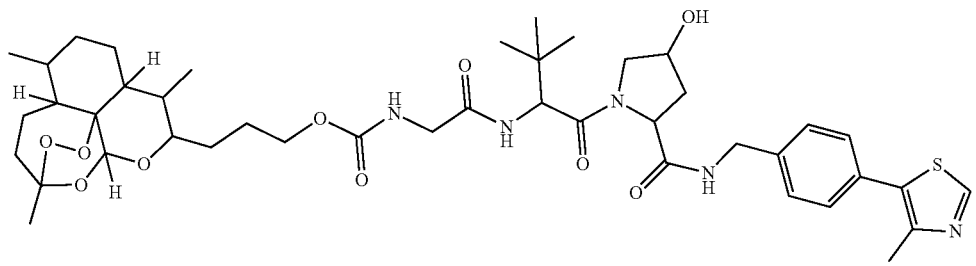 [SMILES: Cc1ncsc1-c1ccc(CNC(=O)C2CC(O)CN2C(=O)C(NC(=O)CNC(=O)OCCCC2OC3OC4(C)CCC5C(C)CCC(C2C)C35OO4)C(C)(C)C)cc1]

By using I-g-L4 (The L part of I-g is L4) instead of I-g-L1 and following the procedure of CL-1 preparation there is obtained CL-4. HRESI-MS m/z: 840.4188 [M+H]$^+$ (calcd 840.4212 for C43H62N5O10S).

Example 5: The preparation of compound CL-5. The chemical structure of CL-5 is shown as follows.

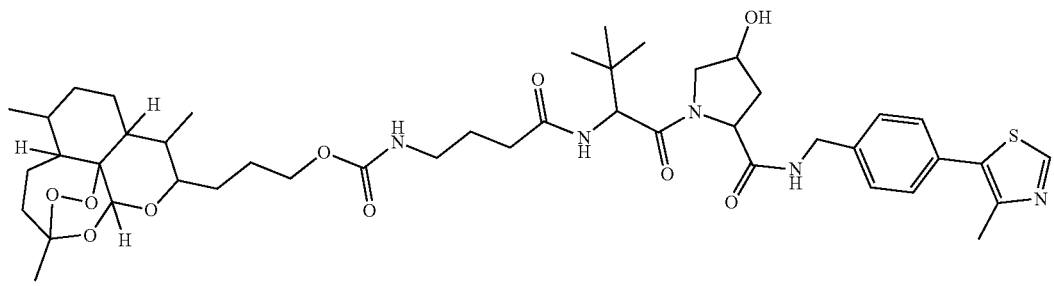 [SMILES: Cc1ncsc1-c1ccc(CNC(=O)C2CC(O)CN2C(=O)C(NC(=O)CCCNC(=O)OCCCC2OC3OC4(C)CCC5C(C)CCC(C2C)C35OO4)C(C)(C)C)cc1]

By using I-g-L6 (The L part of I-g is L6) instead of I-g-L1 and following the procedure of CL-1 preparation there is obtained CL-5. HRESI-MS m/z: 868.4507 [M+H]$^+$ (calcd 868.4525 for C45H66N5O10S).

Example 6: The preparation of compound CL-6. The chemical structure of CL-6 is shown as follows.

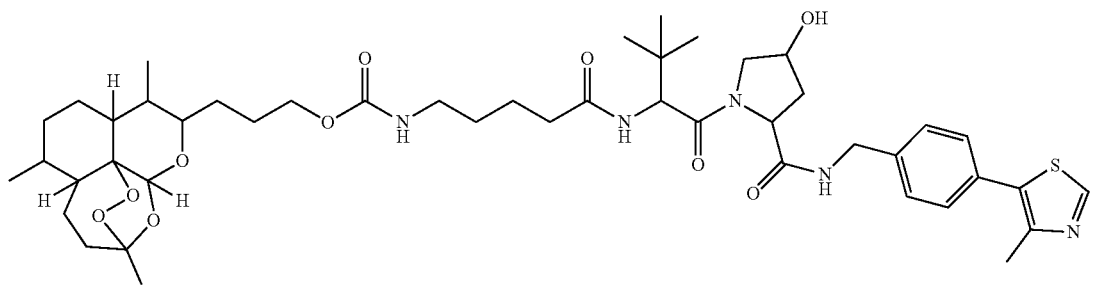 [SMILES: Cc1ncsc1-c1ccc(CNC(=O)C2CC(O)CN2C(=O)C(NC(=O)CCCCNC(=O)OCCCC2OC3OC4(C)CCC5C(C)CCC(C2C)C35OO4)C(C)(C)C)cc1]

By using I-g-L7 (The L part of I-g is L7) instead of I-g-L1 and following the procedure of CL-1 preparation there is obtained CL-6. HRESI-MS m/z: 882.4680 [M+H]$^+$ (calcd 882.4687 for C46H68N5O10S).

Example 7: The preparation of compound CL-7. The chemical structure of CL-7 is shown as follows.

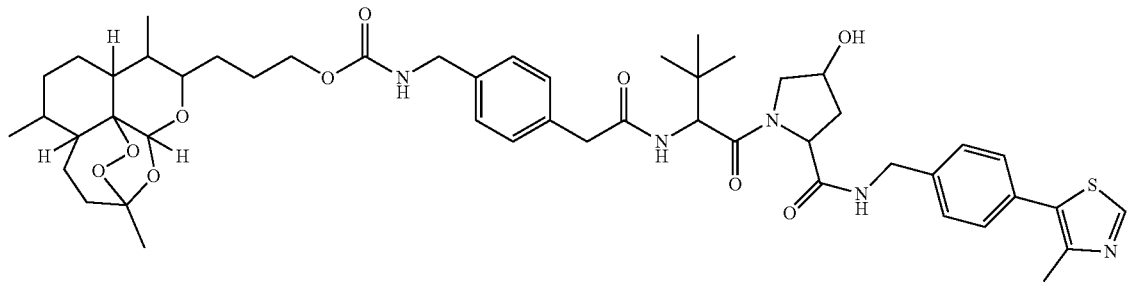 [SMILES: Cc1ncsc1-c1ccc(CNC(=O)C2CC(O)CN2C(=O)C(NC(=O)Cc2ccc(CNC(=O)OCCCC3OC4OC5(C)CCC6C(C)CCC(C3C)C46OO5)cc2)C(C)(C)C)cc1]

By using I-g-L8 (The L part of I-g is L8) instead of I-g-L1 and following the procedure of CL-1 preparation there is obtained CL-7. HRESI-MS m/z: 930.4639 [M+H]$^+$ (calcd 930.4681 for C50H68N5O10S).

Example 8: The preparation of compound CL-8. The chemical structure of CL-8 is shown as follows.

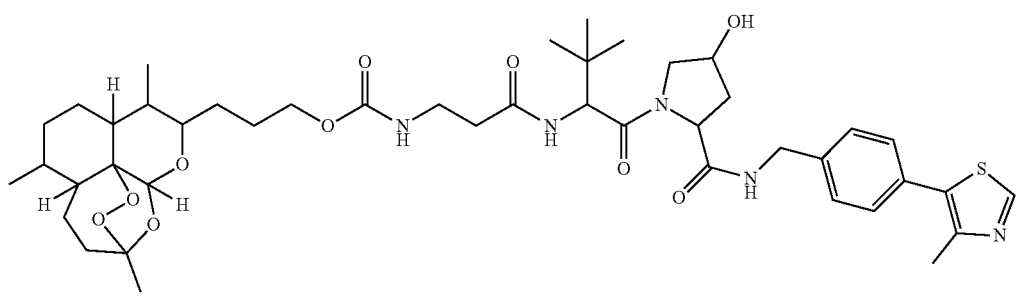 [SMILES: Cc1ncsc1-c1ccc(CNC(=O)C2CC(O)CN2C(=O)C(NC(=O)CCNC(=O)OCCCC2OC3OC4(C)CCC5C(C)CCC(C2C)C35OO4)C(C)(C)C)cc1]

By using I-g-L5 (The L part of I-g is L5) instead of I-g-L1 and following the procedure of CL-1 preparation there is obtained CL-8. HRESI-MS m/z: 854.4366 [M+H]$^+$ (calcd 854.4368 for C44H64N5O10S).

Example 9: The preparation of compound CL-9. The chemical structure of CL-9 is shown as follows.

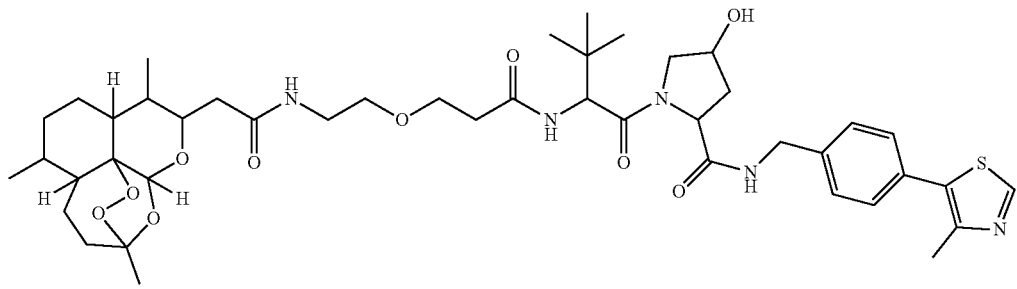 [SMILES: Cc1ncsc1-c1ccc(CNC(=O)C2CC(O)CN2C(=O)C(NC(=O)CCOCCNC(=O)CC2OC3OC4(C)CCC5C(C)CCC(C2C)C35OO4)C(C)(C)C)cc1]

The synthetic scheme of CL-9 is shown as follows.

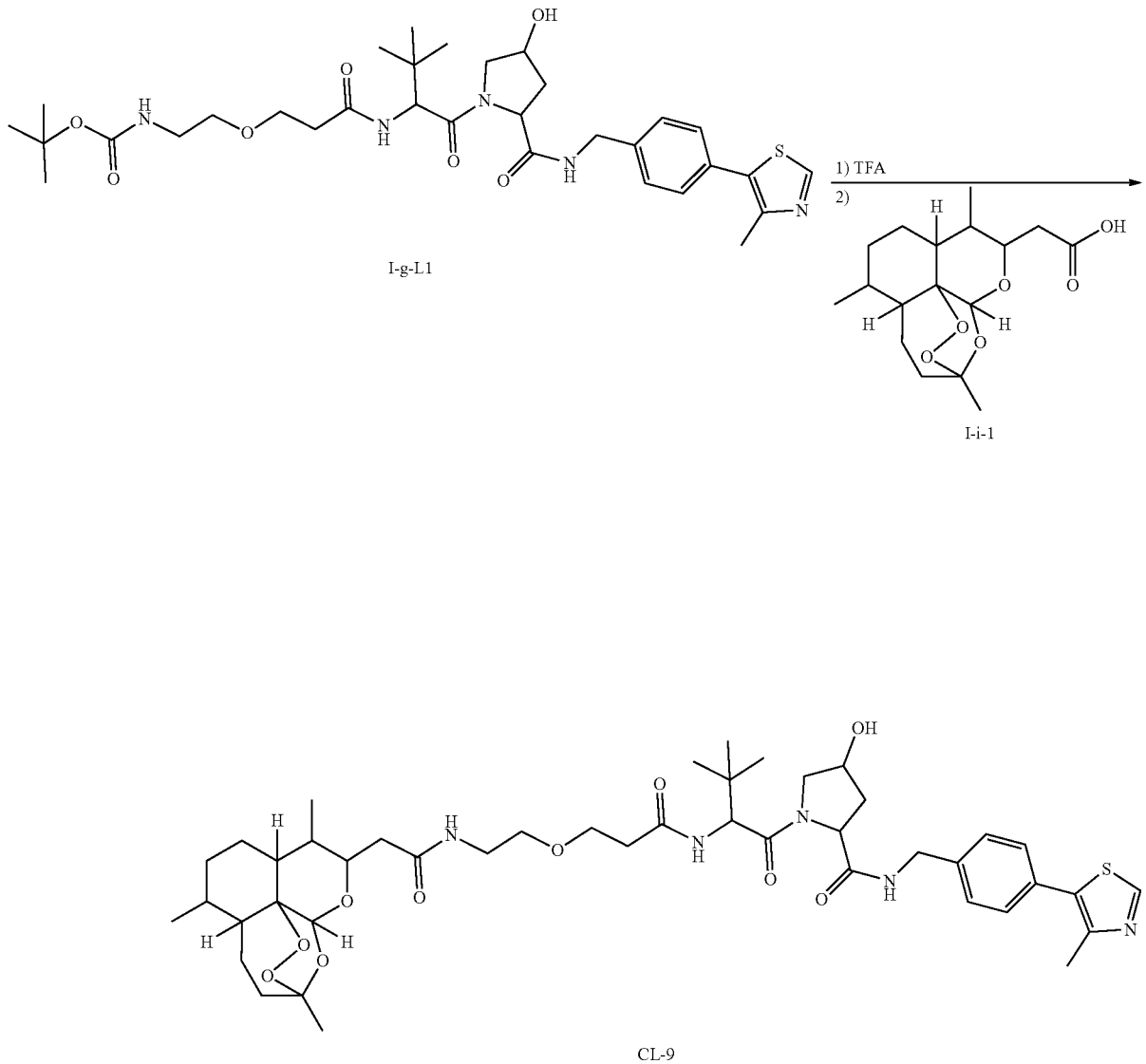

The compound I-g-L1 (The L part of I-g is L1, 48 mg, 0.0743 mmol) was dissolved in the mixed solvent of dichloromethane and trifluoroacetic acid (3 mL, the proportion of trifluoroacetic acid was 30%). The mixture was stirred for 0.5 hour to remove the Boc group of I-e. The solvents were then removed under vacuum. The desired residue was dissolved in DMSO, followed by addition of N,N-diisopropylethylamine to the above mixture to make the solution become neutral or slightly basic. In another round-bottom flask was added I-i-1 (24.3 mg, 0.0743 mmol), EDCI (28.5 mg, 0.1486 mmol) and DMSO. Then above mentioned DMSO solution containing free amino group was added to the flask. N,N-diisopropylethylamine was finally added to the above mixture to make the pH>9. The mixture was stirred at room temperature overnight. Then the reaction was quenched by addition of saturated ammonium chloride aqueous solution, followed by extraction with dichloromethane. The combined organic phase was washed with brine, dried over sodium sulphate, and filtered. The filtrate was concentrated under vacuum and the desired residue was purified with prepared HPLC to give the product CL-9 as white solid (7.98 mg, 12.58%). HRESI-MS m/z: 854.4340 [M+H]$^+$ (calcd 854.4368 for C44H64N5O11S).

Example 10: The preparation of compound CL-10. The chemical structure of CL-10 is shown as follows.

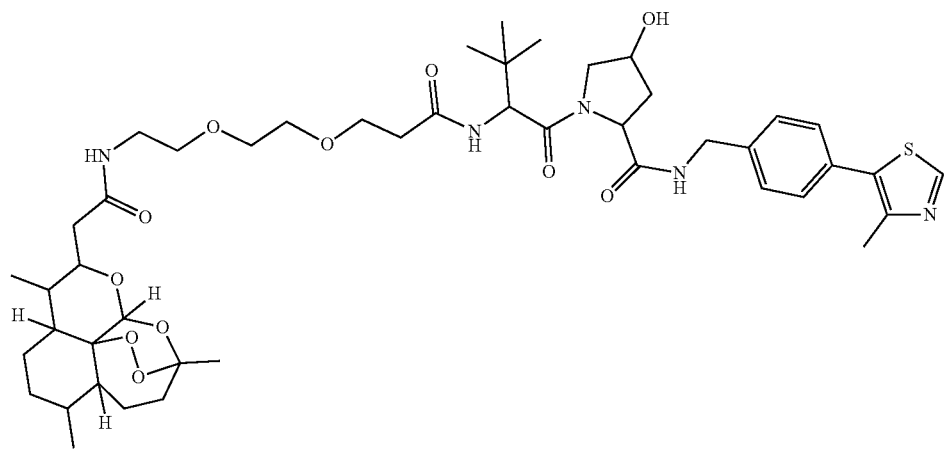 [SMILES: Cc1ncsc1-c1ccc(CNC(=O)C2CC(O)CN2C(=O)C(NC(=O)CCOCCOCCNC(=O)CC2OC3OC4(C)CCC5C(C)CCC(C2C)C35OO4)C(C)(C)C)cc1]

By using I-g-L2 (The L part of I-g is L2) instead of I-g-L1 and following the procedure of CL-9 preparation them is obtained CL-10. HRESI-MS m/z: 898.4656 [M+H]+ (calcd 898.4631 for C46H68N5O11S).

Example 11: The preparation of compound CL-11. The chemical structure of CL-11 is shown as follows.

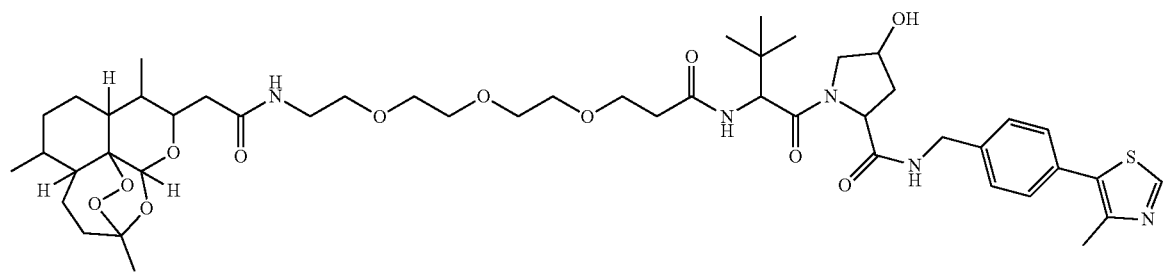 [SMILES: Cc1ncsc1-c1ccc(CNC(=O)C2CC(O)CN2C(=O)C(NC(=O)CCOCCOCCOCCNC(=O)CC2OC3OC4(C)CCC5C(C)CCC(C2C)C35OO4)C(C)(C)C)cc1]

By using I-g-L3 (The L part of I-g is L3) instead of I-g-L1 and following the procedure of CL-9 preparation there is obtained CL-11. HRESI-MS m/z: 942.4852 [M+H]+ (calcd 942.4893 for C48H72N5O12S).

Example 12: The preparation of compound CL-12. The chemical structure of CL-12 is shown as follows.

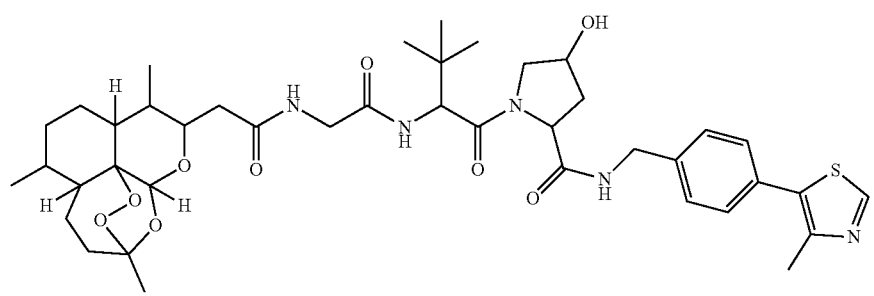 [SMILES: Cc1ncsc1-c1ccc(CNC(=O)C2CC(O)CN2C(=O)C(NC(=O)CNC(=O)CC2OC3OC4(C)CCC5C(C)CCC(C2C)C35OO4)C(C)(C)C)cc1]

By using I-g-L4 (The L part of I-g is L4) instead of I-g-L1 and following the procedure of CL-9 preparation there is obtained CL-12. HRESI-MS m/z: 796.3928 [M+H]+ (calcd 796.3950 for C41H58N5O9S).

Example 13: The preparation of compound CL-13. The chemical structure of CL-13 is shown as follows.

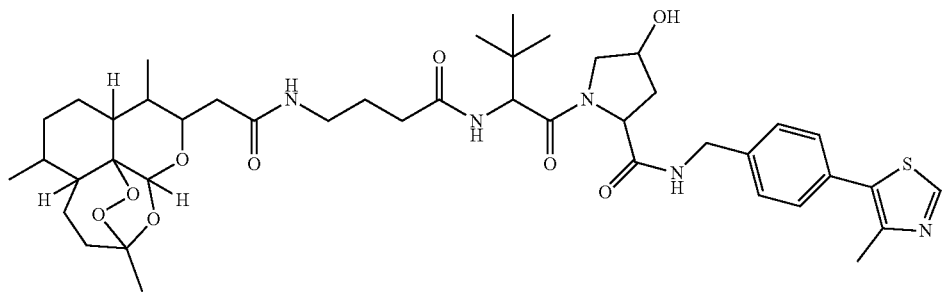 [SMILES: Cc1ncsc1-c1ccc(CNC(=O)C2CC(O)CN2C(=O)C(NC(=O)CCCNC(=O)CC2OC3OC4(C)CCC5C(C)CCC(C2C)C35OO4)C(C)(C)C)cc1]

By using I-g-L6 (The L part of I-g is L6) instead of I-g-L1 and following the procedure of CL-9 preparation there is obtained CL-13. HRESI-MS m/z: 824.4242 [M+H]+ (calcd 824.4263 for C43H62N5O9S).

Example 14: The preparation of compound CL-14. The chemical structure of CL-14 is shown as follows.

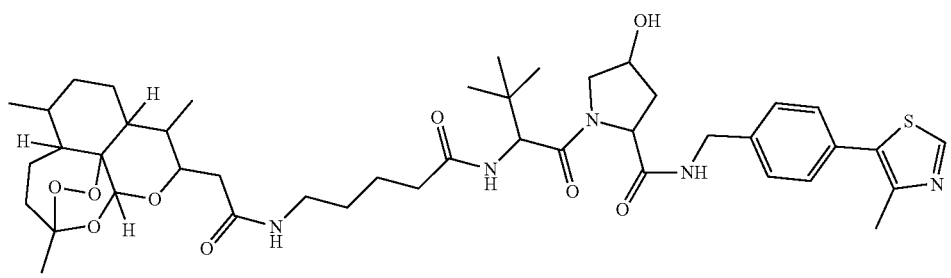 [SMILES: Cc1ncsc1-c1ccc(CNC(=O)C2CC(O)CN2C(=O)C(NC(=O)CCCCNC(=O)CC2OC3OC4(C)CCC5C(C)CCC(C2C)C35OO4)C(C)(C)C)cc1]

By using I-g-L7 (The L part of I-g is L7) instead of I-g-L1 and following the procedure of CL-9 preparation there is obtained CL-14. HRESI-MS m/z: 838.4400 [M+H]+ (calcd 838.4419 for C44H64N5O9S).

Example 15: The preparation of compound CL-15. The chemical structure of CL-15 is shown as follows.

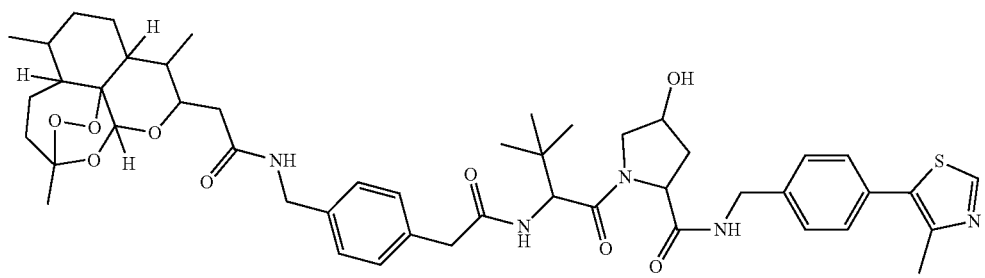 [SMILES: Cc1ncsc1-c1ccc(CNC(=O)C2CC(O)CN2C(=O)C(NC(=O)Cc2ccc(CNC(=O)CC3OC4OC5(C)CCC6C(C)CCC(C3C)C46OO5)cc2)C(C)(C)C)cc1]

By using I-g-L8 (The L part of I-g is L8) instead of I-g-L1 and following the procedure of CL-9 preparation there is obtained CL-15. HRESI-MS m/z: 886.4406 [M+H]+ (calcd 886.4419 for C48H64N5O9S).

Example 16: The preparation of compound CL-16. The chemical structure of CL-16 is shown as follows.

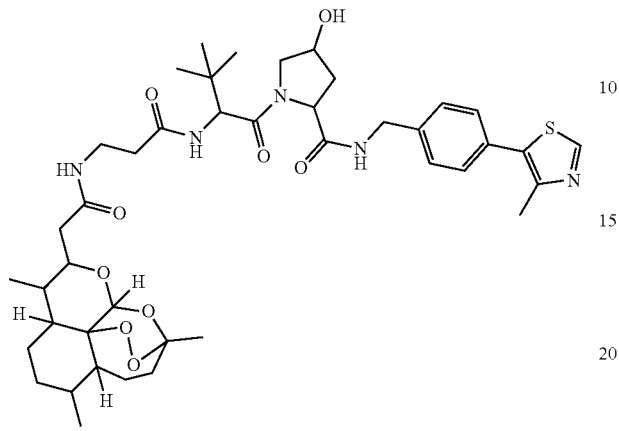

By using I-g-L5 (The L part of I-g is L5) instead of I-g-L1 and following the procedure of CL-9 preparation there is obtained CL-16. HRESI-MS m/z: 810.4080 [M+H]+ (calcd 810.4106 for C42H60N5O9S).

Example 17: The preparation of compound CL-17. The chemical structure of CL-17 is shown as follows.

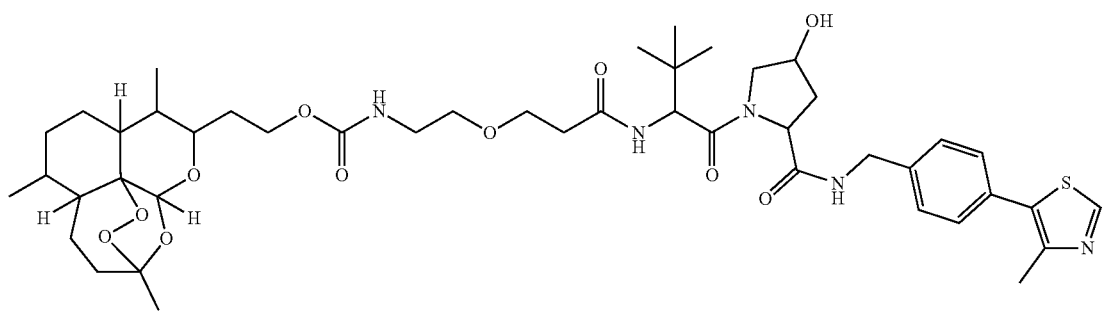 [SMILES: Cc1ncsc1-c1ccc(CNC(=O)C2CC(O)CN2C(=O)C(NC(=O)CCOCCNC(=O)OCCC2OC3OC4(C)CCC5C(C)CCC(C2C)C35OO4)C(C)(C)C)cc1]

By using I-a-2 (The n of I-a is 2) instead of I-a-3 and following the procedure of CL-1 preparation them is obtained CL-17. $^1$H NMR (400 MHz, DMSO-d6) δ 8.99 (s, 1H), 8.57 (t, J=6.0 Hz, 1H), 7.94 (d, J=9.2 Hz, 1H), 7.37-7.43 (m, 4H), 7.02 (t, J=5.6 Hz, 1H), 5.32 (s, 1H), 4.56 (d, J=9.6 Hz, 1H), 4.40-4.46 (m, 2H), 4.34 (m, 1H), 4.18-4.23 (dd, J=5.6 Hz, J$_2$=16 Hz, 1H), 4.02-4.08 (m, 2H), 3.89-3.96 (m, 1H), 3.54-3.69 (m, 4H), 3.33-3.39 (m, 2H), 3.12 (q, J=6.0 Hz, 2H), 2.44 (s, 3H), 2.31-2.38 (m, 2H), 2.09-2.16 (m, 1H), 1.79-2.13 (m, 6H), 1.46-1.69 (m, 4H), 1.23-1.41 (m, 6H), 1.11-1.16 (m, 1H), 0.93 (s, 9H), 0.89 (d, J=6.4 Hz, 3H), 0.79 (d, J=7.6 Hz, 3H); HRESI-MS m/z: 884.4458 [M+H]+ (calcd 884.4474 for C42H60N5O9S).

Example 18: The preparation of compound CL-18. The chemical structure of CL-18 is shown as follows.

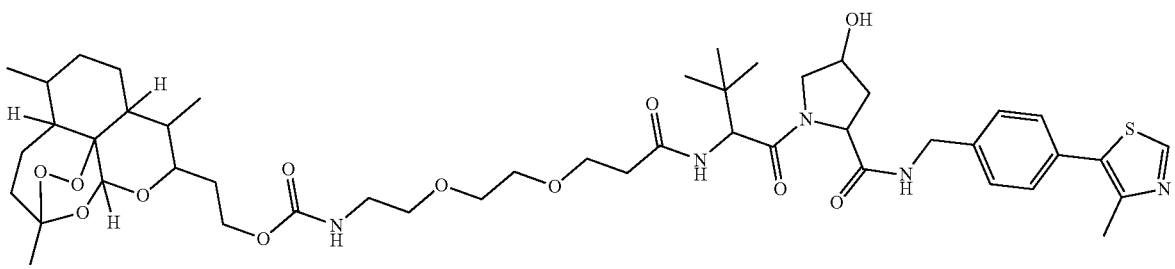 [SMILES: Cc1ncsc1-c1ccc(CNC(=O)C2CC(O)CN2C(=O)C(NC(=O)CCOCCOCCNC(=O)OCCC2OC3OC4(C)CCC5C(C)CCC(C2C)C35OO4)C(C)(C)C)cc1]

By using I-g-L2 (The L part of I-g is L2) instead of I-g-L1 and following the procedure of CL-17 preparation them is obtained CL-18. ¹H NMR (400 MHz, DMSO-d$_6$) δ 8.99 (s, 1H), 8.57 (t, J=6.0 Hz, 1H), 7.93 (d, J=9.2 Hz, 1H), 7.37-7.43 (m, 4H), 7.07 (t, J=5.6 Hz, 1H), 5.32 (s, 1H), 4.56 (m, 1H), 4.40-4.44 (m, 2H), 4.34 (m, 1H), 4.19-4.23 (m, 2H), 4.05 (m, 2H), 3.90-3.96 (m, 1H), 3.55-3.69 (m, 7H, mixed with water peak), 3.44-3.47 (m, 4H), 3.36-3.39 (t, J=6.0 Hz, 2H), 3.11 (m, 2H), 2.66-2.67 (m, 1H), 2.44 (s, 3H), 2.31-2.38 (m, 2H), 1.79-2.17 (m, 8H), 1.47-1.70 (m, 5H), 1.25-1.39 (m, 7H), 1.09-1.16 (m, 2H), 0.93 (s, 9H), 0.89 (d, J=6.4 Hz, 3H), 0.79 (d, J=7.6 Hz, 3H); HRESI-MS m/z: 928.4713 [M+H]$^+$ (calcd 928.4736 for C47H70N5O12S).

Example 19: The preparation of compound CL-19. The chemical structure of CL-19 is shown as follows.

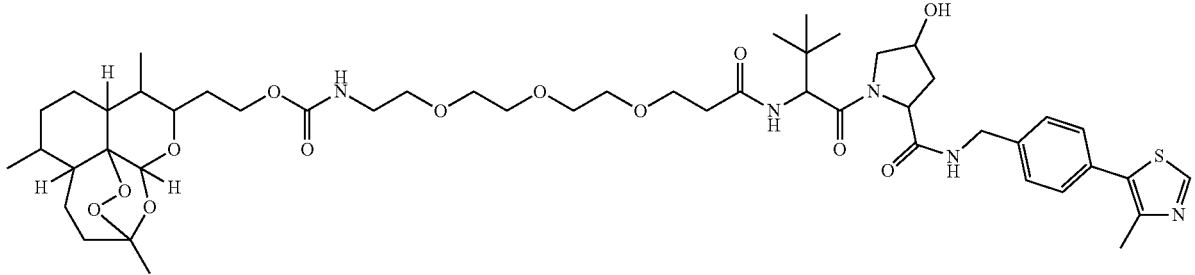 [SMILES: Cc1ncsc1-c1ccc(CNC(=O)C2CC(O)CN2C(=O)C(NC(=O)CCOCCOCCOCCNC(=O)OCCC2OC3OC4(C)CCC5C(C)CCC(C2C)C35OO4)C(C)(C)C)cc1]

By using I-g-L3 (The L part of I-g is L3) instead of I-g-L1 and following the procedure of CL-17 preparation there is obtained CL-19. HRESI-MS m/z: 972.4986 [M+H]$^+$ (calcd 972.4998 for C49H74N5O13S).

Example 20: The preparation of compound CL-20. The chemical structure of CL-20 is shown as follows.

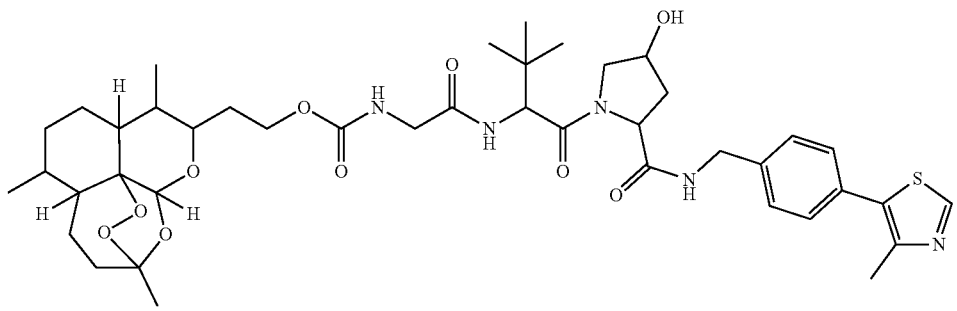 [SMILES: Cc1ncsc1-c1ccc(CNC(=O)C2CC(O)CN2C(=O)C(NC(=O)CNC(=O)OCCC2OC3OC4(C)CCC5C(C)CCC(C2C)C35OO4)C(C)(C)C)cc1]

By using I-g-L4 (The L part of I-g is L4) instead of I-g-L1 and following the procedure of CL-17 preparation there is obtained CL-20. ¹H NMR (400 MHz, DMSO-d6) δ 8.98 (s, 1H), 8.59 (t, J=6.0 Hz, 1H), 7.75 (d, J=9.6 Hz, 1H), 7.37-7.43 (m, 4H), 7.30 (t, J=5.6 Hz, 1H), 5.33 (s, 1H), 4.54 (m, 1H), 4.39-4.45 (m, 2H), 4.34 (m, 1H), 4.19-4.24 (dd, J$_1$=5.2 Hz, J$_2$=16 Hz, 1H), 4.07 (m, 2H), 3.59-3.96 (m, 38H, blended water peak), 2.44 (s, 3H), 1.78-2.17 (m, 7H), 1.45-1.69 (m, 5H), 1.25-1.36 (m, 6H), 1.09-1.16 (m, 2H), 0.92 (s, 9H), 0.89 (d, J=6.0 Hz, 3H), 0.79 (d, J=7.6 Hz, 3H); HRESI-MS m/z: 826.4021 [M+H]$^+$ (calcd 826.4055 for C42H60N5O10S).

Example 21: The preparation of compound CL-21. The chemical structure of CL-21 is shown as follows.

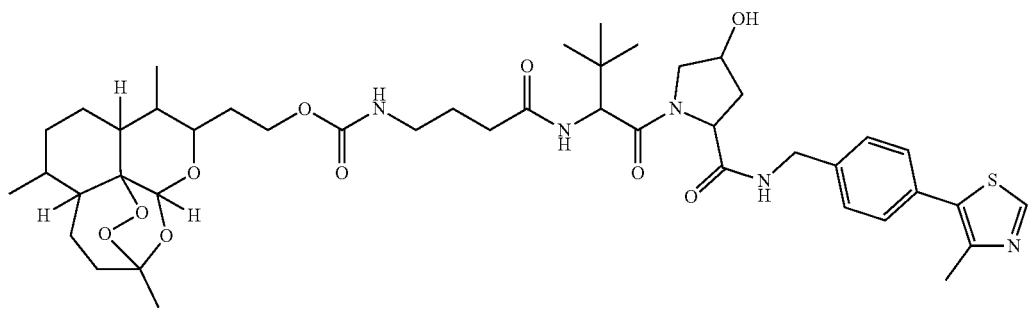 [SMILES: Cc1ncsc1-c1ccc(CNC(=O)C2CC(O)CN2C(=O)C(NC(=O)CCCNC(=O)OCCC2OC3OC4(C)CCC5C(C)CCC(C2C)C35OO4)C(C)(C)C)cc1]

By using I-g-L6 (The L part of I-g is L6) instead of I-g-L1 and following the procedure of CL-17 preparation there is obtained CL-21. $^1$H NMR (400 MHz, DMSO-d6) δ 8.99 (s, 1H), 8.57 (t, J=6.0 Hz, 1H), 7.90 (d, J=9.2 Hz, 1H), 7.37-7.43 (m, 4H), 7.30 (t, J=6.0 Hz, 1H), 5.33 (s, 1H), 4.54 (m, 1H), 4.40-4.46 (m, 2H), 4.34 (m, 1H), 4.01-4.09 (m, 1H), 3.95 (m, 1H), 3.61-3.69 (m, 2H), 2.90-2.98 (m, 3H), 2.67 (m, 1H), 2.44 (s, 3H), 2.33 (m, 1H), 2.21-2.28 (m, 1H), 1.79-2.17 (m, 8H), 1.47-1.70 (m, 7H), 1.25-1.39 (m, 6H), 1.09-1.16 (m, 2H), 0.93 (s, 9H), 0.89 (d, J=6.4 Hz, 3H), 0.79 (d, J=7.2 Hz, 3H); HRESI-MS m/z: 854.4340 [M+H]$^+$ (calcd 854.4368 for C44H64N5O10S).

Example 22: The preparation of compound CL-22. The chemical structure of CL-22 is shown as follows.

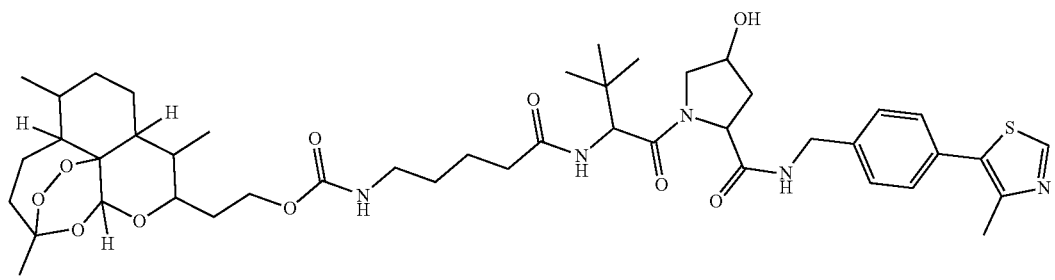 [SMILES: Cc1ncsc1-c1ccc(CNC(=O)C2CC(O)CN2C(=O)C(NC(=O)CCCCNC(=O)OCCC2OC3OC4(C)CCC5C(C)CCC(C2C)C35OO4)C(C)(C)C)cc1]

By using I-g-L7 (The L part of I-g is L7) instead of I-g-L1 and following the procedure of CL-17 preparation there is obtained CL-22. $^1$H NMR (400 MHz, DMSO-d6) δ 8.99 (s, 1H), 8.57 (t, J=6.0 Hz, 1H), 7.85 (d, J=9.2 Hz, 1H), 7.37-7.43 (m, 4H), 7.06 (t, J=6.0 Hz, 1H), 5.32 (s, 1H), 4.54 (m, 1H), 4.40-4.47 (m, 2H), 4.36 (m, 1H), 4.18-4.23 (m, 1H), 4.01-4.09 (m, 2H), 3.89-3.96 (m, 1H), 3.61-3.68 (m, 2H), 2.95 (m, 2H), 2.44 (s, 3H), 2.33 (m, 1H), 2.24 (m, 1H), 1.79-2.17 (m, 9H), 1.25-1.70 (m, 16H), 1.09-1.16 (m, 2H), 0.93 (s, 9H), 0.89 (d, J=6.0 Hz, 3H), 0.79 (d, J=7.6 Hz, 3H); HRESI-MS m/z: 868.4482 [M+H]$^+$ (calcd 868.4525 for C45H66N5O10S).

Example 23: The preparation of compound CL-23. The chemical structure of CL-23 is shown as follows.

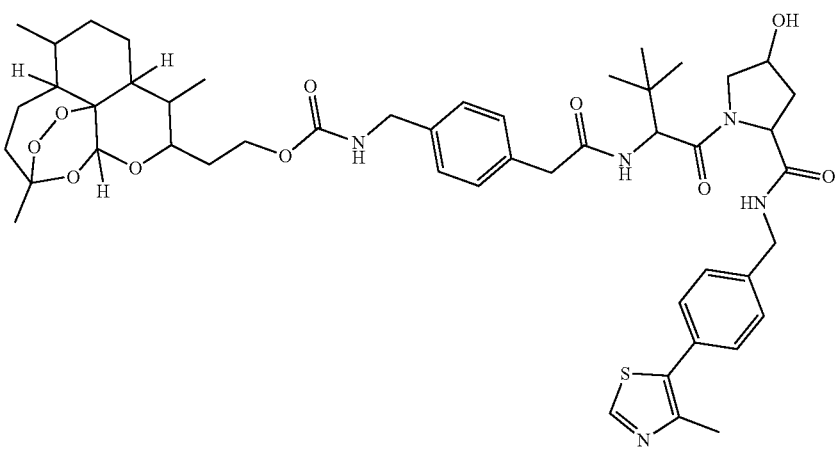 [SMILES: Cc1ncsc1-c1ccc(CNC(=O)C2CC(O)CN2C(=O)C(NC(=O)Cc2ccc(CNC(=O)OCCC3OC4OC5(C)CCC6C(C)CCC(C3C)C46OO5)cc2)C(C)(C)C)cc1]

By using I-g-L8 (The L part of I-g is L8) instead of I-g-L1 and following the procedure of CL-17 preparation there is obtained CL-23. $^1$H NMR (400 MHz, DMSO-d$_6$) δ 8.99 (s, 1H), 8.59 (t, J=6.0 Hz, 1H), 8.10 (d, J=9.2 Hz, 1H), 7.61 (t, J=6.0 Hz, 1H), 7.37-7.43 (m, 4H), 7.21 (d, J=8.0 Hz, 2H), 7.15 (d, J=8.0 Hz, 2H), 5.33 (s, 1H), 4.52 (m, 1H), 4.40-4.46 (m, 2H), 4.34 (m, 1H), 4.19-4.24 (dd, J$_1$=5.2 Hz, J$_2$=8.0 Hz, 1H), 4.05-4.13 (m, 2H), 3.60-3.67 (m, 2H), 3.42 (d, J=13.6 Hz, 1H), 2.44 (s, 3H), 2.10-2.17 (m, 1H), 1.95-2.05 (m, 2H), 1.79-1.92 (m, 3H), 1.47-1.69 (m, 4H), 1.25-1.39 (m, 6H), 1.09-1.17 (m, 1H), 0.91 (s, 9H), 0.89 (d, J=6.8 Hz, 3H), 0.79 (d, J=7.2 Hz, 3H); HRESI-MS m/z: 916.4500 [M+H]$^+$ (calcd 916.4525 for C49H66N5O10S).

Example 24: The preparation of compound CL-24. The chemical structure of CL-24 is shown as follows.

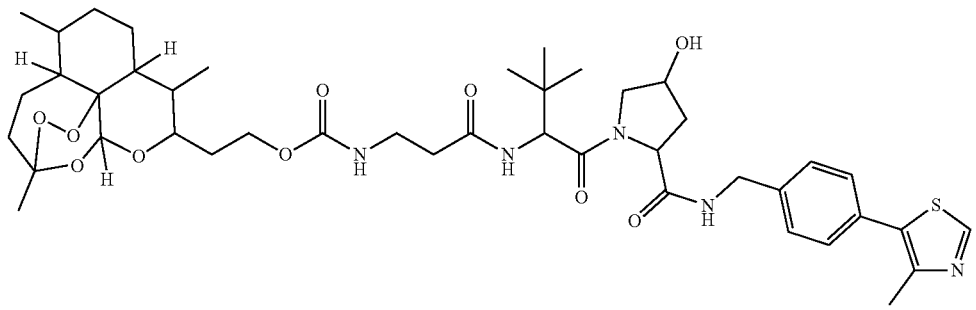 [SMILES: Cc1ncsc1-c1ccc(CNC(=O)C2CC(O)CN2C(=O)C(NC(=O)CCNC(=O)OCCC2OC3OC4(C)CCC5C(C)CCC(C2C)C35OO4)C(C)(C)C)cc1]

By using I-g-L5 (The L part of I-g is L5) instead of I-g-L1 and following the procedure of CL-17 preparation there is obtained CL-24. $^1$H NMR (400 MHz, DMSO-d$_6$) δ 8.99 (s, 1H), 8.58 (t, J=6.0 Hz, 1H), 7.96 (d, J=9.2 Hz, 1H), 7.37-7.44 (m, 4H), 6.98 (t, J=5.6 Hz, 1H), 4.54 (m, 1H), 4.40-4.45 (m, 2H), 4.34 (m, 1H), 4.22 (m, 1H), 4.05 (m, 2H), 3.96 (m, 1H), 3.61-3.69 (m, 2H), 3.17 (m, 2H), 2.44 (s, 3H), 2.30-2.34 (m, 1H), 2.09-2.16 (m, 1H), 1.79-2.07 (m, 5H), 1.46-1.70 (m, 4H), 1.23-1.39 (m, 6H), 1.09-1.16 (m, 2H), 0.93 (s, 9H), 0.89 (d, J=6.4 Hz, 3H), 0.79 (d, J=7.6 Hz, 3H); HRESI-MS m/z: 840.4193 [M+H]$^+$ (calcd 840.4212 for C43H62N5O10S).

Example 25: The preparation of compound CL-25. The chemical structure of CL-25 is shown as follows.

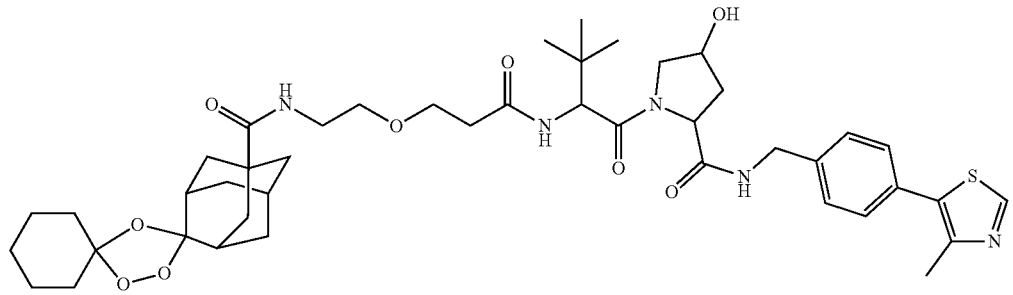 [SMILES: Cc1ncsc1-c1ccc(CNC(=O)C2CC(O)CN2C(=O)C(NC(=O)CCOCCNC(=O)C23CC4CC(C2)C2(OOC5(CCCCC5)O2)C(C4)C3)C(C)(C)C)cc1]

The synthetic scheme of CL-25 is shown as follows.

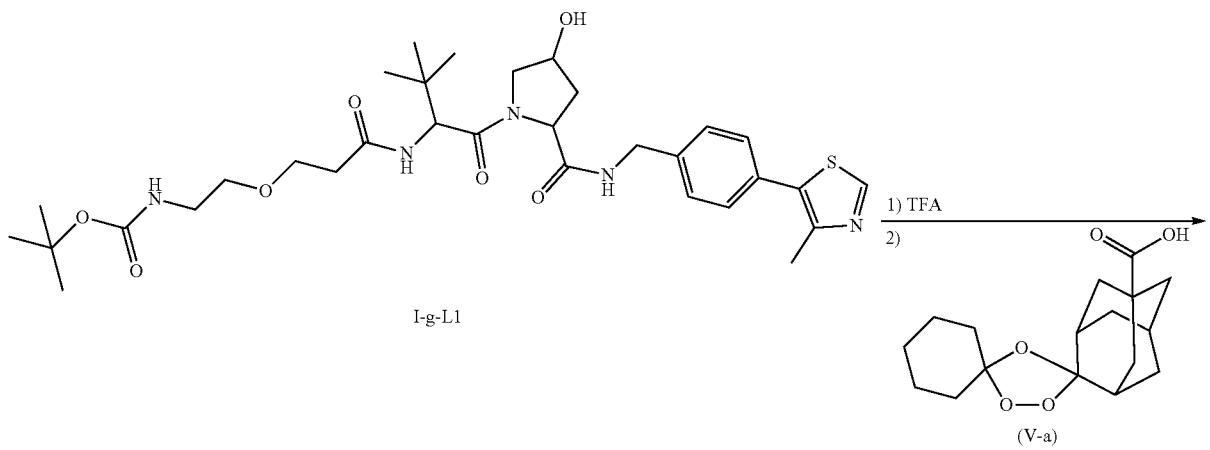

I-g-L1

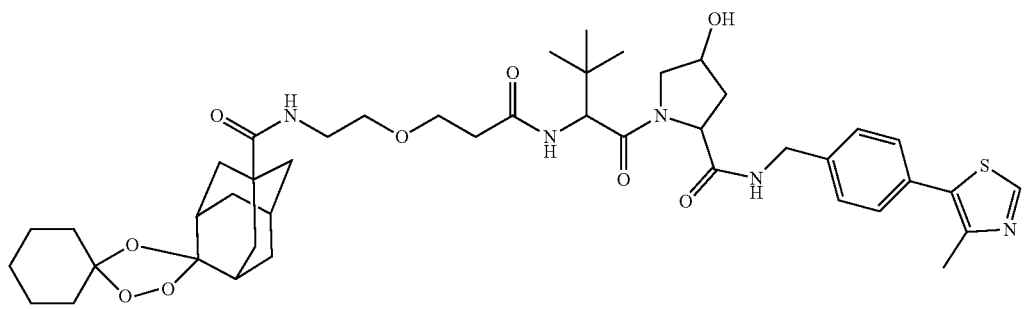

40

The compound I-g-L1 (The L part of I-g is L1, 32 mg, 0.049 mmol, 1 eq) was dissolved in the mixed solvent of dichloromethane and trifluoroacetic acid (the proportion of trifluoroacetic acid was 20%). The mixture was stirred for 0.5 hour to remove the Boc group of I-g-L1. The solvents were then removed under vacuum. The desired residue was dissolved in dichloromethane (5 mL), followed by addition of N,N-diisopropylethylamine to the above mixture to make the solution become neutral. To the mixture was then added V-a (15 mg, 0.049 mmol, 1 eq.), EDCI (14 mg, 0.073 mmol, 1.5 eq.) and DMAP (9 mg, 0.073 mmol, 1.5 eq.). The mixture was stirred at room temperature for 4 hours. Then the reaction mixture was washed with saturated ammonium chloride aqueous solution (20 mL×2) and brine (20 mL). The combined organic phase was dried over sodium sulphate, and filtered. The filtrate was concentrated under vacuum and the desired residue was purified with prepared HPLC to give the product CL-25 as white solid (29 mg, 70.0%). HRESI-MS m/z: 836.4239 [M+H]$^+$ (calcd 836.4263 for C44H62N5O9S).

Example 26: The preparation of compound CL-26. The chemical structure of CL-26 is shown as follows.

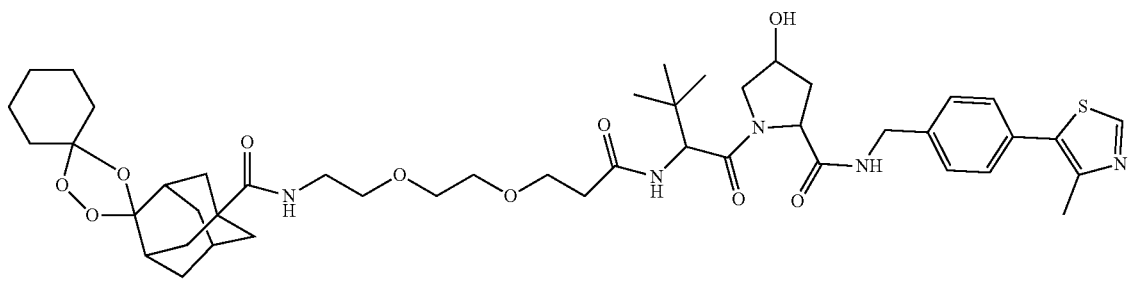 [SMILES: Cc1ncsc1-c1ccc(CNC(=O)C2CC(O)CN2C(=O)C(NC(=O)CCOCCOCCNC(=O)C23CC4CC(C2)C2(OOC5(CCCCC5)O2)C(C4)C3)C(C)(C)C)cc1]

By using I-g-L2 (The L part of I-g is L2) instead of I-g-L1 and following the procedure of CL-25 preparation there is obtained CL-26. HRESI-MS m/z: 880.4515 [M+H]+ (calcd 880.4525 for C46H66N5O10S).

Example 27: The preparation of compound CL-27. The chemical structure of CL-27 is shown as follows.

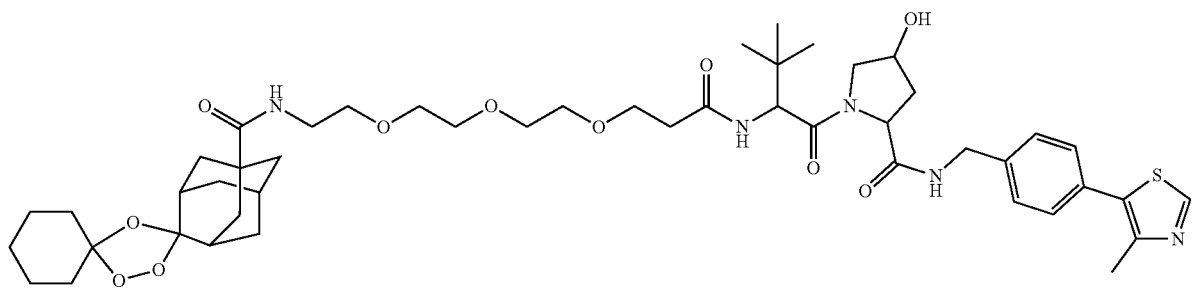 [SMILES: Cc1ncsc1-c1ccc(CNC(=O)C2CC(O)CN2C(=O)C(NC(=O)CCOCCOCCOCCNC(=O)C23CC4CC(C2)C2(OOC5(CCCCC5)O2)C(C4)C3)C(C)(C)C)cc1]

By using I-g-L3 (The L part of I-g is L3) instead of I-g-L1 and following the procedure of CL-25 preparation there is obtained CL-27. HRESI-MS m/z: 924.4787 [M+H]+ (calcd 924.4777 for C48H70N5O11S).

Example 28: The preparation of compound CL-28. The chemical structure of CL-28 is shown as follows.

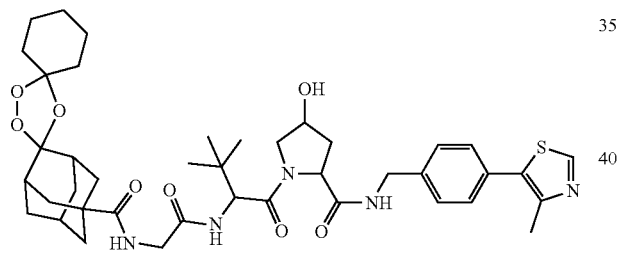

By using I-g-L4 (The L part of I-g is L4) instead of I-g-L1 and following the procedure of CL-25 preparation there is obtained CL-28. HRESI-MS m/z: 778.3817 [M+H]+ (calcd 778.3844 for C41H56N5O8S).

Example 29: The preparation of compound CL-29. The chemical structure of CL-29 is shown as follows.

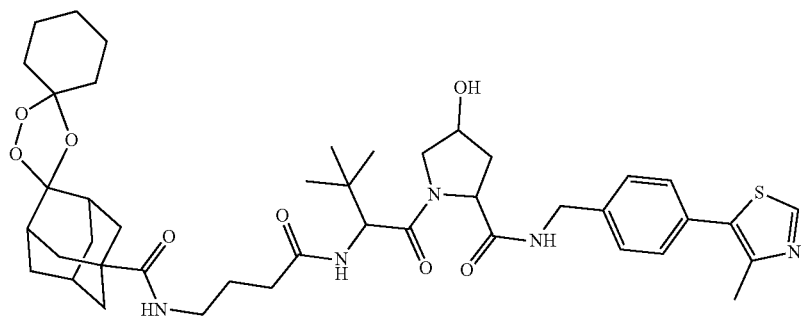 [SMILES: Cc1ncsc1-c1ccc(CNC(=O)C2CC(O)CN2C(=O)C(NC(=O)CCCNC(=O)C23CC4CC(C2)C2(OOC5(CCCCC5)O2)C(C4)C3)C(C)(C)C)cc1]

By using I-g-L6 (The L part of I-g is L6) instead of I-g-L1 and following the procedure of CL-25 preparation there is obtained CL-29. HRESI-MS m/z: 806.4160 [M+H]$^+$ (calcd 816.4163 for C43H60N5O8S).

Example 30: The preparation of compound CL-30. The chemical structure of CL-30 is shown as follows.

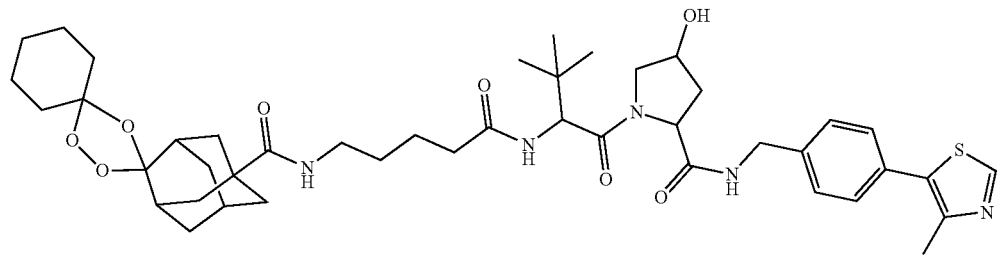 [SMILES: Cc1ncsc1-c1ccc(CNC(=O)C2CC(O)CN2C(=O)C(NC(=O)CCCCNC(=O)C23CC4CC(C2)C2(OOC5(CCCCC5)O2)C(C4)C3)C(C)(C)C)cc1]

By using I-g-L7 (The L part of I-g is L7) instead of I-g-L1 and following the procedure of CL-25 preparation there is obtained CL-30. HRESI-MS m/z: 820.4295 [M+H]$^+$ (calcd 820.4314 for C44H62N5O8S).

Example 31: The preparation of compound CL-31. The chemical structure of CL-31 is shown as follows.

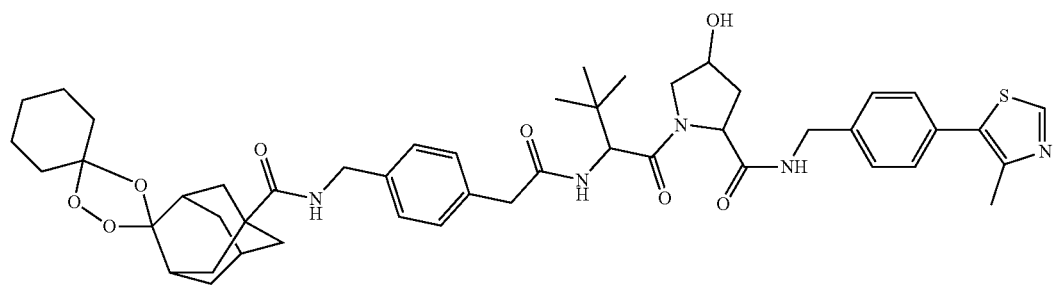 [SMILES: Cc1ncsc1-c1ccc(CNC(=O)C2CC(O)CN2C(=O)C(NC(=O)Cc2ccc(CNC(=O)C34CC5CC(C3)C3(OOC6(CCCCC6)O3)C(C5)C4)cc2)C(C)(C)C)cc1]

By using I-g-L8 (The L part of I-g is L8) instead of I-g-L1 and following the procedure of CL-25 preparation there is obtained CL-31. HRESI-MS m/z: 868.4293 [M+H]$^+$ (calcd 868.4314 for C48H62N5O8S).

Example 32: The preparation of compound CL-32. The chemical structure of CL-32 is shown as follows.

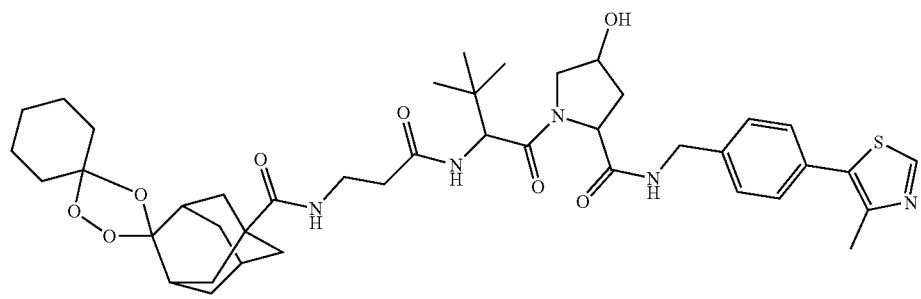 [SMILES: Cc1ncsc1-c1ccc(CNC(=O)C2CC(O)CN2C(=O)C(NC(=O)CCNC(=O)C23CC4CC(C2)C2(OOC5(CCCCC5)O2)C(C4)C3)C(C)(C)C)cc1]

By using I-g-L5 (The L part of I-g is L5) instead of I-g-L1 and following the procedure of CL-25 preparation there is obtained CL-32. HRESI-MS m/z: 792.3968 [M+H]$^+$ (calcd 792.4001 for C42H58N5O8S).
Example 33: The preparation of compound CL-40. The chemical structure of CL-40 is shown as follows.
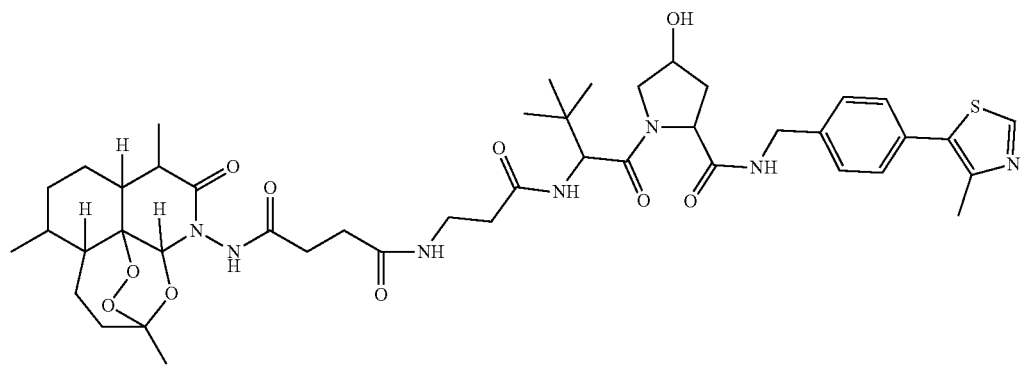
The synthetic scheme of CL-40 is shown as follows.
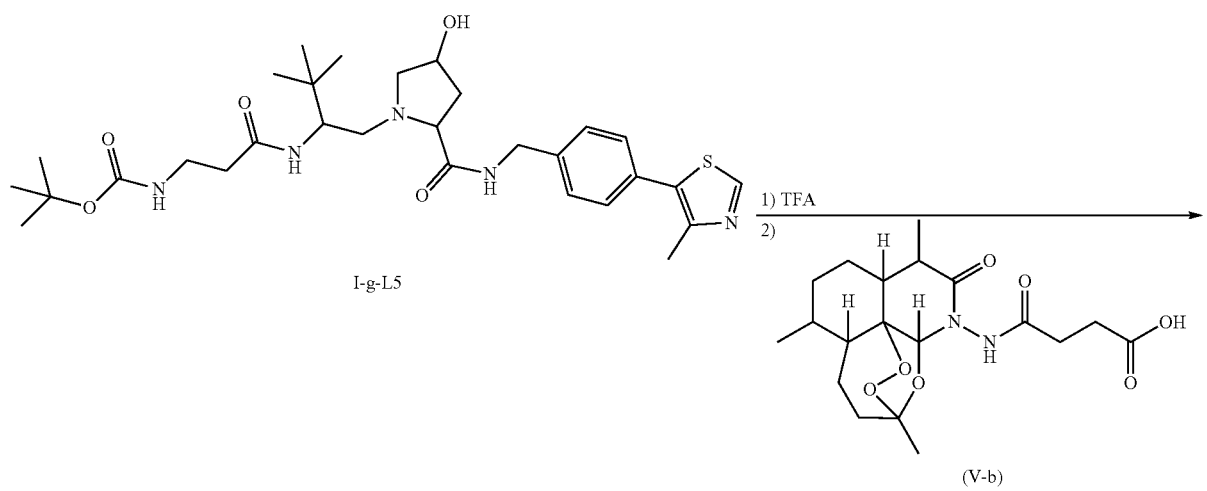
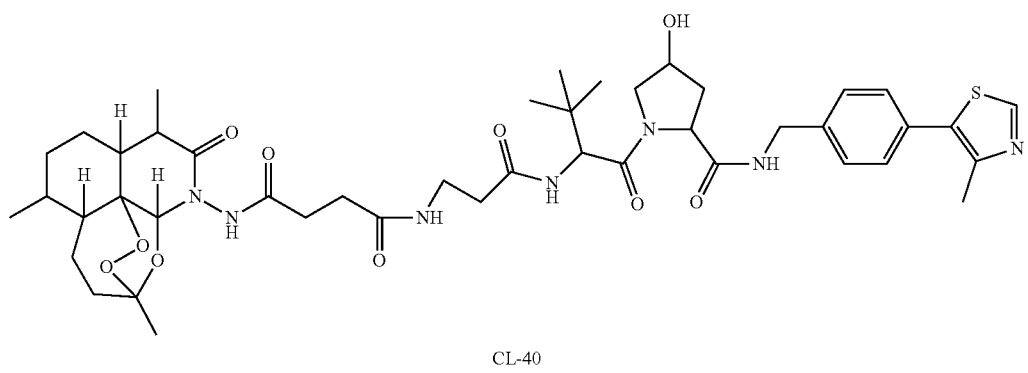
CL-40

By using I-g-L5 (The L part of I-g is L5) and V-b instead of I-g-L1 V-a and following the procedure of CL-25 preparation them is obtained CL-40. HRESI-MS m/z: 880.4284 [M+H]$^+$ (calcd 880.4278 for C44H62N7O10S).

Biological Experiment Example 1 In Vitro Activity Evaluation

MTT Assay:

The synthesized exemplary compounds were prepared into solutions of different concentrations of 20 mm, 10 mm, 5 mm, 2.5 mm, 1.25 mm, 0.625 mm, 0.3125 mm, 0.15625 mm, 0.078 mm and 0 mm with DMSO. Then the above concentrated solutions were diluted by 1000 times with culture medium (i.e. add 1 µL concentrated solution to 999 µL culture medium). The diluted compound solution was added into 96-well plates respectively. Each solution was added to 3 different wells, and 50 µL for each well. After MV4-11 cells were counted, the cell suspension was diluted to 100000/mL, and 50 µl diluted cell suspension was added to each well containing the compound. Then 200 µL PBS solution to each well of the outer ring of 96-well plate. The treated cells were cultured for 48 h. Then 100 µL CellTiter-Glo Luminescent detection reagent was added into each well, followed by incubation in the incubator for 10 min and detection with microplate reader. The cell survival rate and the half inhibitory concentration (IC$_{50}$) of the compound on the growth of tumor cells were calculated. See Table 1 for specific results.

TABLE 1

MTT result of exemplary compounds

| Compound Number | IC$_{50}$ (µM) |
| --- | --- |
| CL-1 | 0.51 |
| CL-2 | 0.59 |
| CL-3 | 0.52 |
| CL-4 | 0.91 |
| CL-5 | 0.55 |
| CL-6 | 5.30 |
| CL-7 | 0.46 |
| CL-8 | 0.24 |
| CL-9 | 4.67 |
| CL-10 | 44.46 |
| CL-11 | 29.59 |
| CL-12 | 1.10 |

TABLE 1-continued

MTT result of exemplary compounds

| Compound Number | IC$_{50}$ (µM) |
| --- | --- |
| CL-13 | 3.10 |
| CL-15 | 0.52 |
| CL-17 | 0.30 |
| CL-18 | 2.66 |
| CL-19 | 0.50 |
| CL-20 | 0.87 |
| CL-21 | 0.84 |
| CL-22 | 0.20 |
| CL-23 | 6.20 |
| CL-24 | 0.50 |
| CL-25 | 5.50 |
| CL-26 | 8.10 |
| CL-27 | 11.95 |
| CL-28 | 9.72 |
| CL-29 | 3.50 |
| CL-30 | 8.31 |
| CL-31 | 3.04 |
| CL-32 | 3.38 |
| CL-40 | 6.08 |

Biological Experiment Example 2 In Vivo Activity Evaluation

Experiment Method:

One hundred µL resuspended U937 leukemia cells (2×10$^6$) were transplanted into NSG mice by caudal vein injection. Every 3 days after transplantation, 50-100 µL peripheral blood was taken from the fundus venous plexus and placed in the EP tube containing heparin sodium. Five hundred µL of red blood cell lysis buffer was immediately added to destroy the red blood cells. The proportion of human-cd45 positive cells was detected by flow cytometry. When the average implantation rate was 0.4%, the model was considered successful, and the mice were randomly divided into groups. The exemplary compound was administered once a day and continuously for 5 days a week (ig, the solvent was corn oil). The drug administration was lasted for 2 weeks. After administration, i.e. on the 15th day, the peripheral blood, spleen and bone marrow of mice were taken to facilitate the detection.

Experiment Result:

As shown in Table 2, FIG. 1, FIG. 2, FIG. 3 and FIG. 4, the exemplary compound CL-8 demonstrated strong inhibition towards the growth of U937 leukemia cells in vivo.

TABLE 2

The anti-leukemia activity of compound CL-8 in vivo

| Group | dosage | Animal number | The proportion of human leukemia cells in spleen of mice | The proportion of human leukemia cells in bone marrow of mice | The proportion of human leukemia cells in peripheral blood of mice |
| --- | --- | --- | --- | --- | --- |
| Solvent control | — | 3 | 34.74 ± 7.35 | 84.20 ± 1.41 | 21.03 ± 4.43 |
| artesunate | 200 mg/kg | 3 | 49.77 ± 9.28 | 91.28 ± 2.20 | 21.92 ± 2.58 |
| CL-8 | 100 mg/kg | 3 | 11.39 ± 21.3 | 0.38 ± 0.08 | 0.96 ± 0.16 |

Although the invention has been described by specific embodiments, modifications and equivalent changes am obvious to those skilled in the field of the invention, and they am all within the scope of the invention.

What is claimed is:

1. A compound of formula (M)

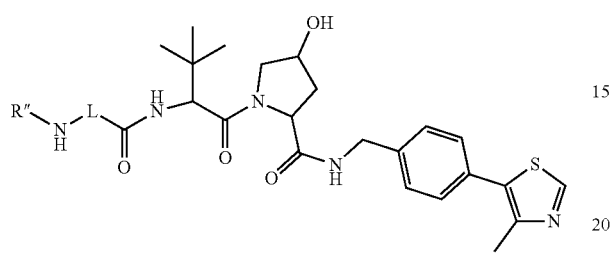

Wherein:

R" is

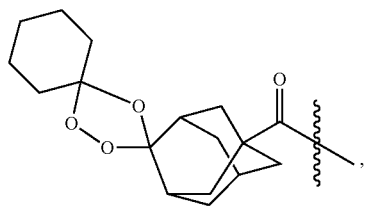

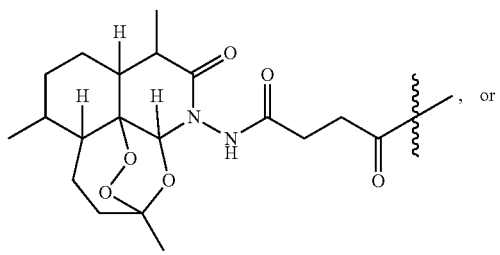

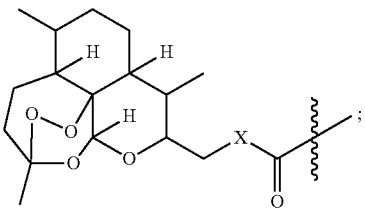

L is —C$_1$-C$_8$ alkylene, oxygen-containing alkylene, or

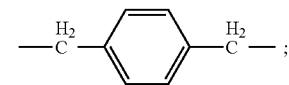

the number of oxygen atoms in said oxygen-containing alkylene is 1, 2, 3, 4 or 5, said oxygen is connected with C$_2$ alkylene;

when R" is R3, n is independently selected from 0, 1, 2, 3, 4 or 5; X is oxygen or —CH$_2$—, or a pharmaceutical acceptable salt or stereoisomer thereof.

2. The compound according to claim 1 of formula I

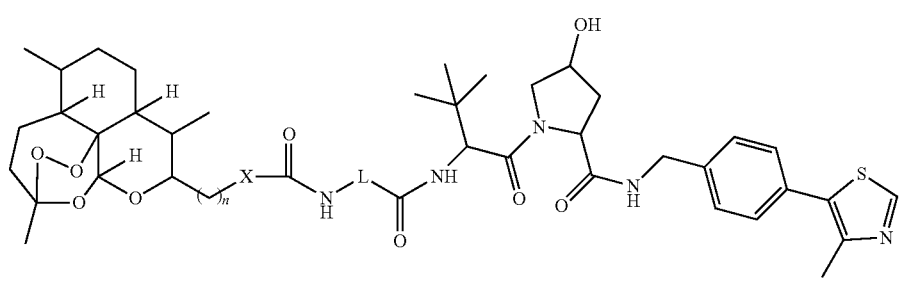

wherein:

n is independently selected from 0, 1, 2, 3, 4 or 5;

X is oxygen or —CH$_2$—;

L is selected from —C$_1$-C$_8$alkylene, oxygen-containing alkylene,

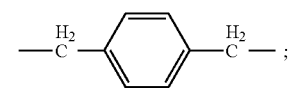

the number of oxygen atoms in said oxygen-containing alkylene is 1, 2, 3, 4, or 5, said oxygen is connected with C₂ alkylene, or a pharmaceutical acceptable salt or stereoisomer thereof.

3. The compound according to claim 2 of formula I-1

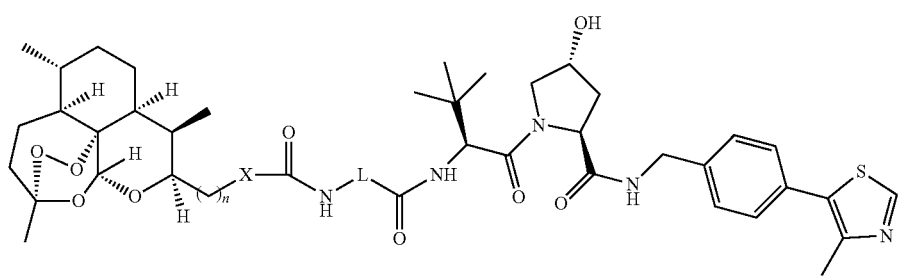

I-1 wherein:
n is independently selected from 0, 1, 2, 3, 4 or 5;
X is oxygen or —CH₂—;
L is selected from —C₁-C₈ alkylene, oxygen-containing alkylene,

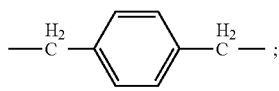

the number of oxygen atoms in said oxygen-containing alkyl is 1, 2, 3, 4, or 5, said oxygen is connected with C₂ alkylene, or a pharmaceutical acceptable salt or stereoisomer thereof.

4. The compound of claim 2, wherein L is selected from the following structures:

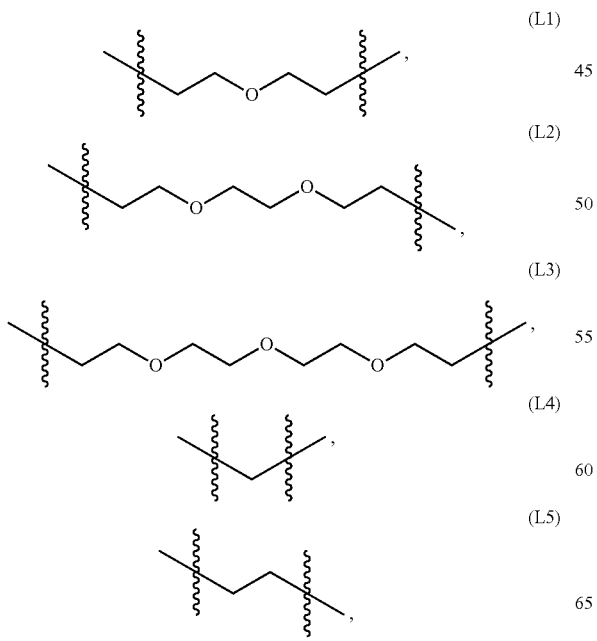

(L1)

(L2)

(L3)

(L4)

(L5)

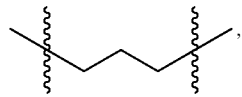

(L6)

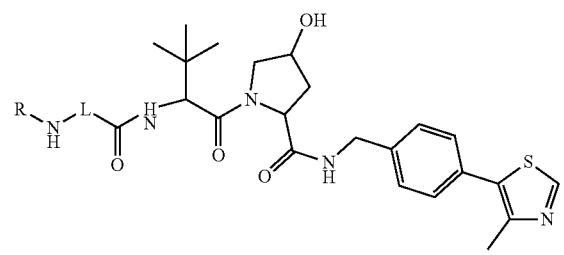

(L7)

(L8)

5. The compound according to claim 1 of formula II

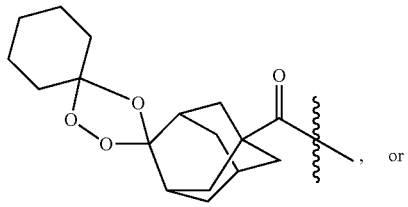

II

Wherein:
R is (R1)

, or (R2)

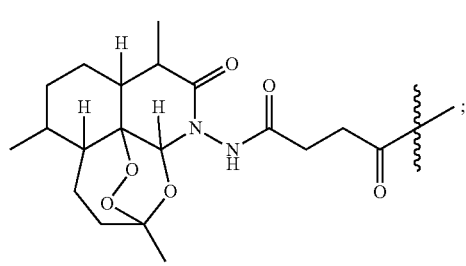

L is selected from —C$_1$-C$_8$ alkylene, oxygen-containing alkylene,

—CH$_2$—C$_6$H$_4$—CH$_2$—;

the number of oxygen atoms in said oxygen-containing alkylene is 1, 2, 3, 4, or 5, said oxygen is connected with C$_2$ alkylene,
or a pharmaceutical acceptable salt or stereoisomer thereof.

6. The compound of claim 5, wherein L is selected from the following structures:

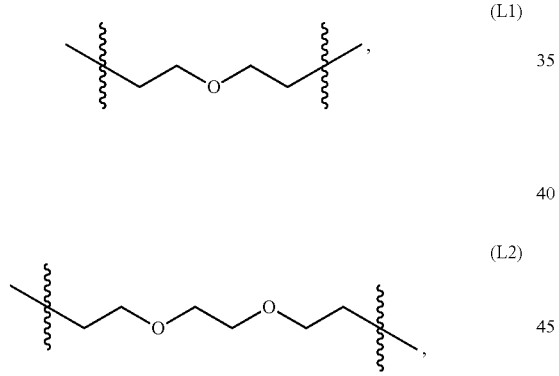

(L1), (L2)

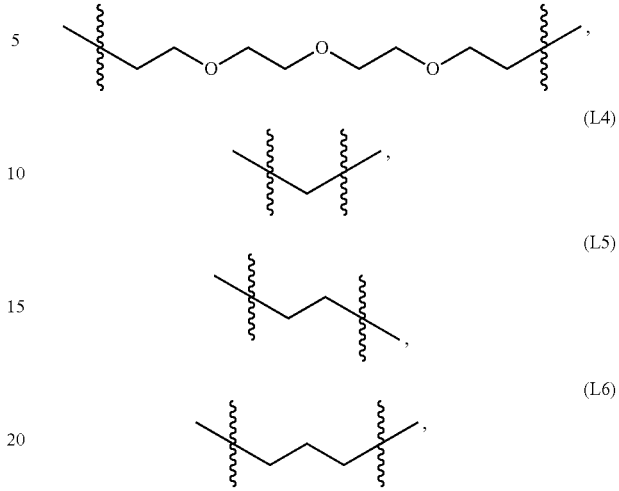

(L3), (L4), (L5), (L6), (L7), (L8)

7. The compound of claim 1, which is selected from the following structures:

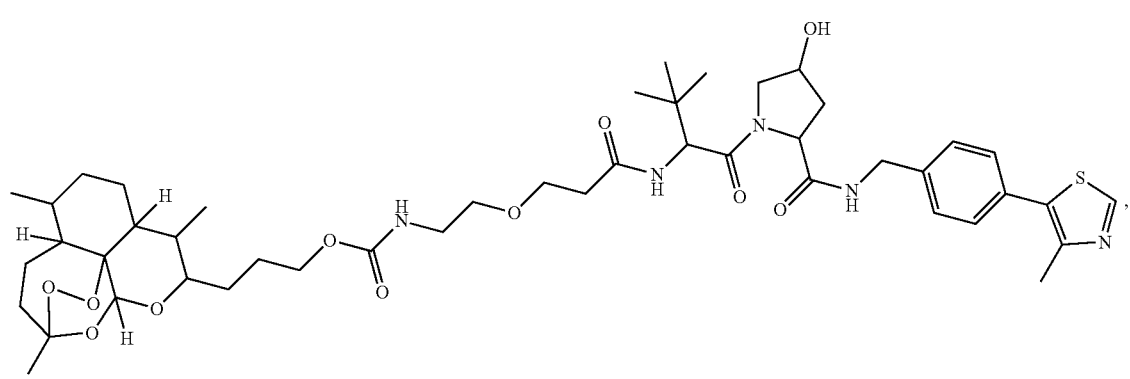

CL-1

CL-2
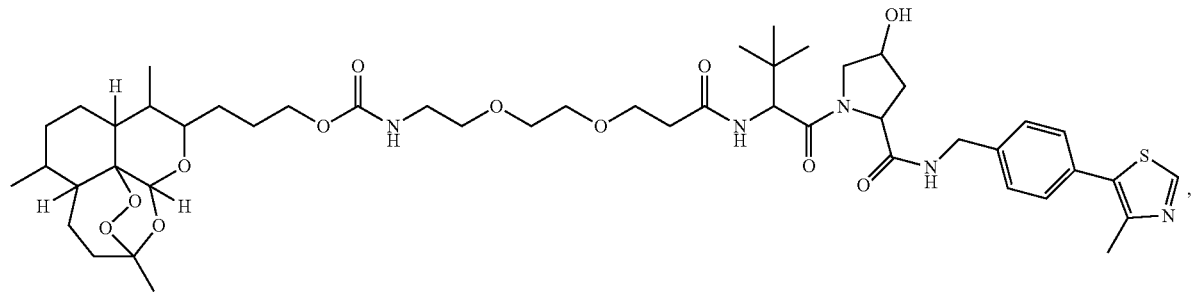
CL-3
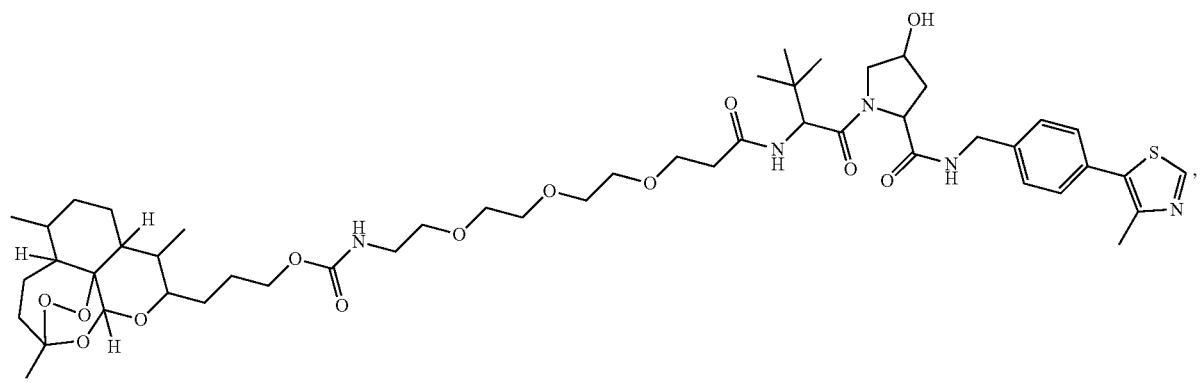
CL-4
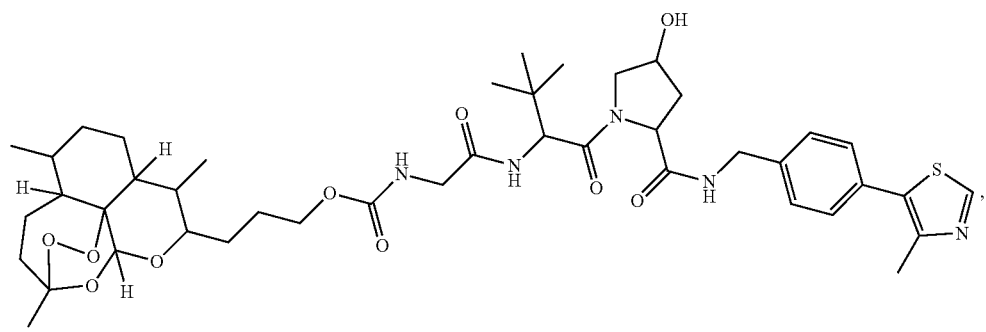
CL-5
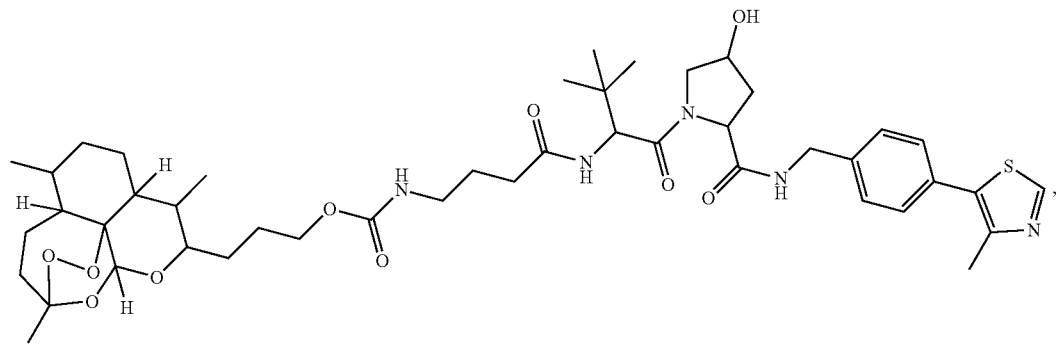

-continued
CL-6
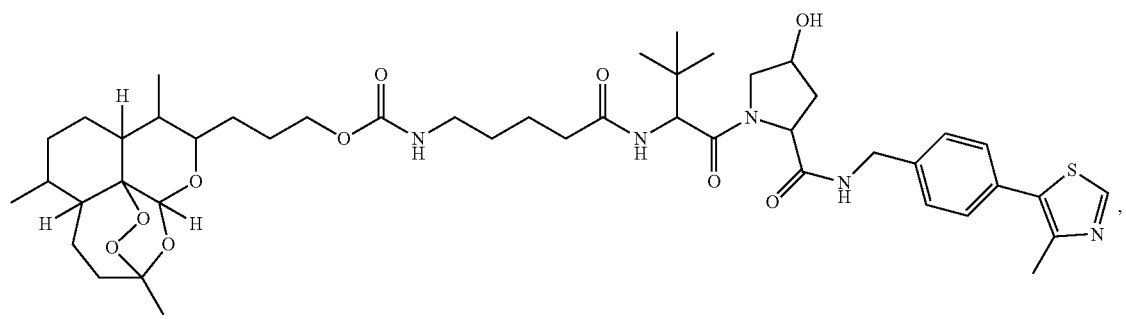
CL-7
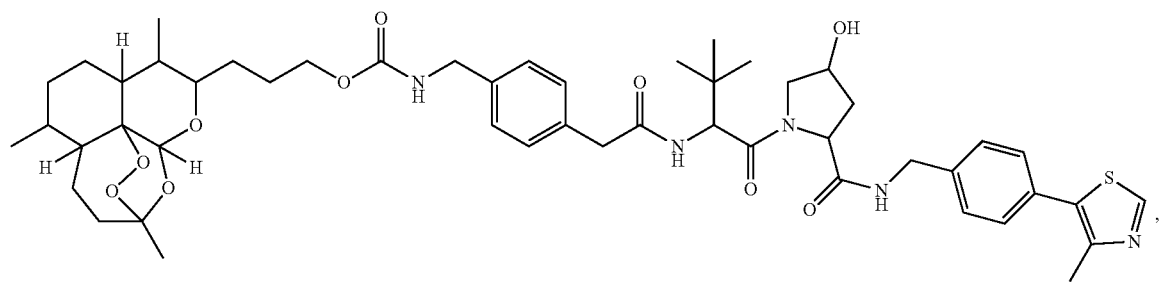
CL-8
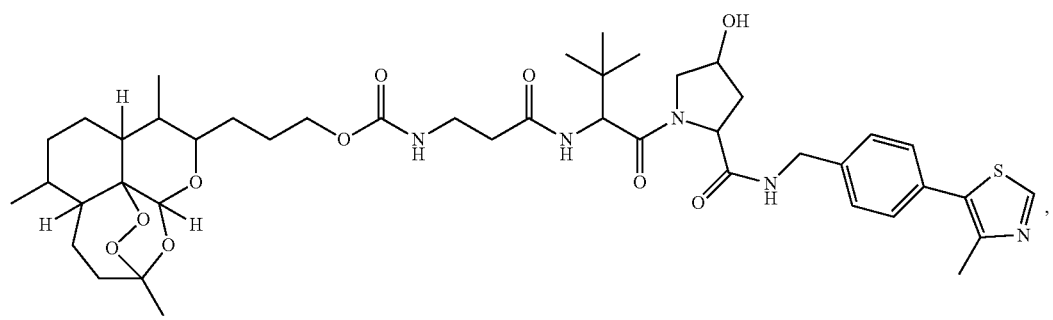
CL-9
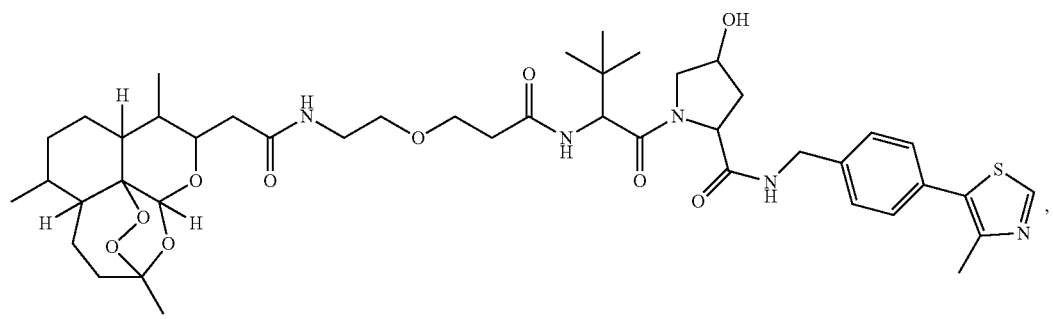
CL-10
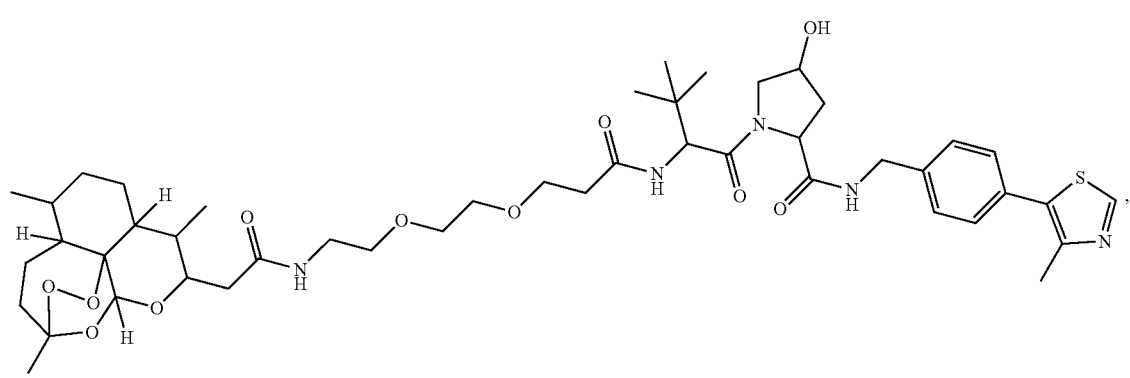

C-11
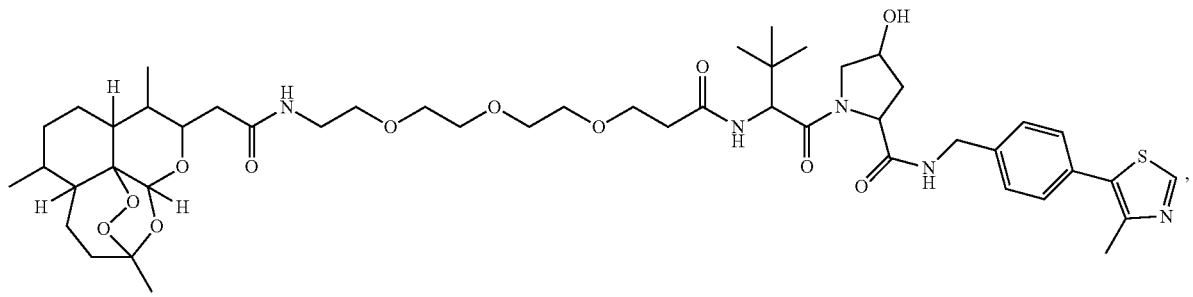
CL-12
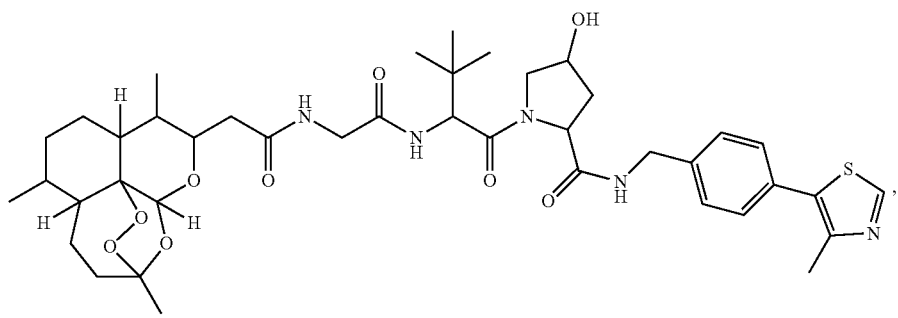
CL-13
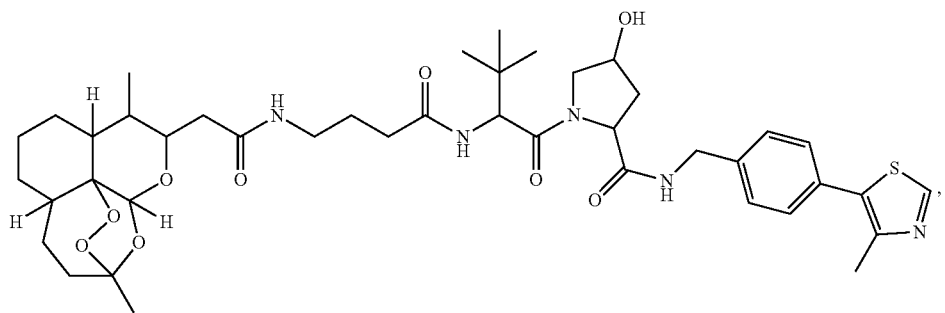
CL-14
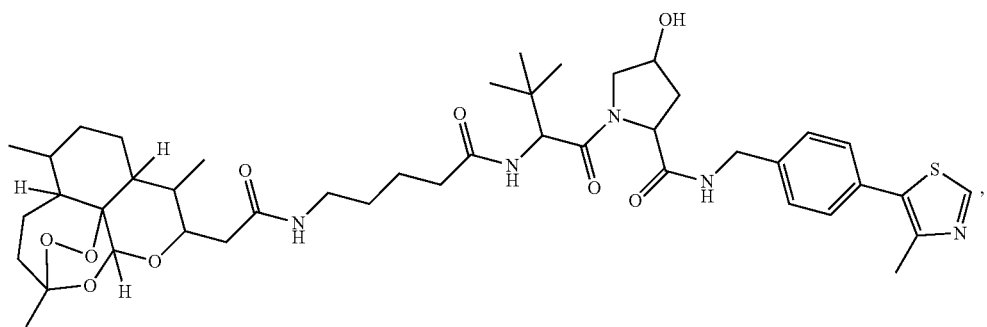
CL-15
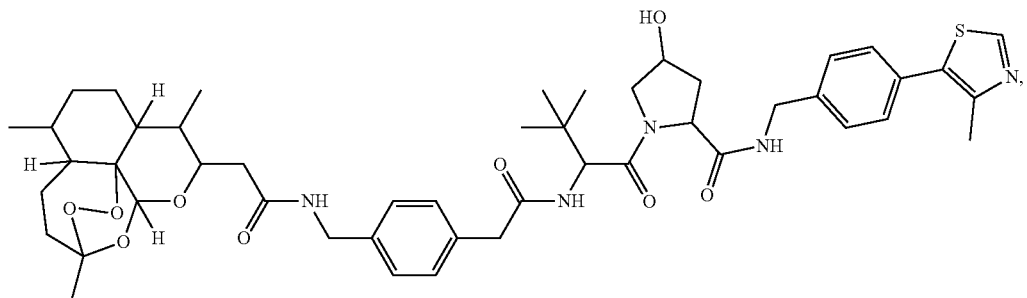

CL-16
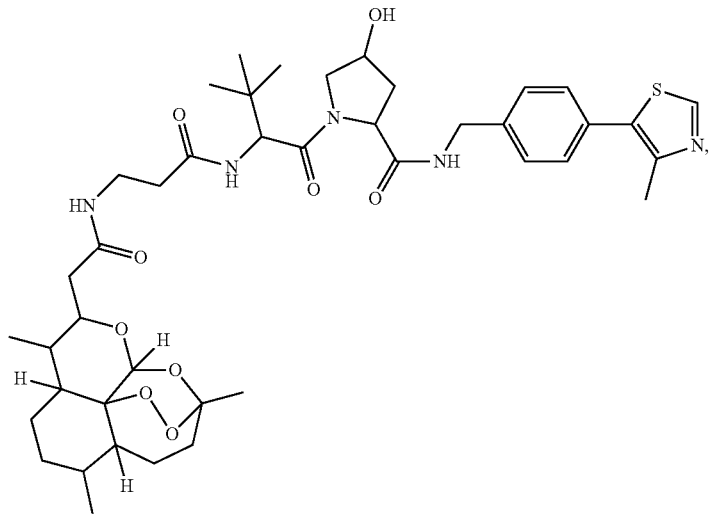
CL-17
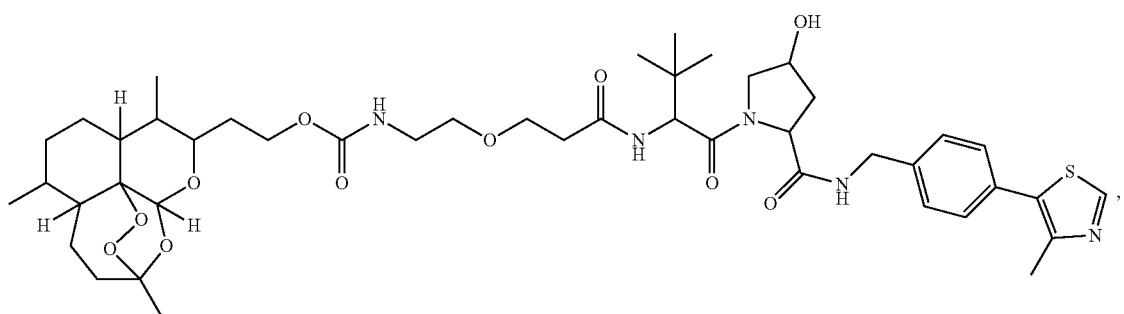
CL-18
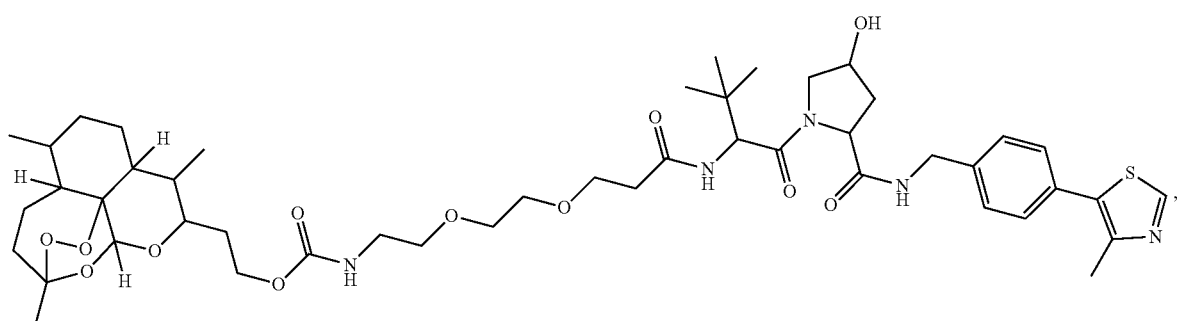
CL-19
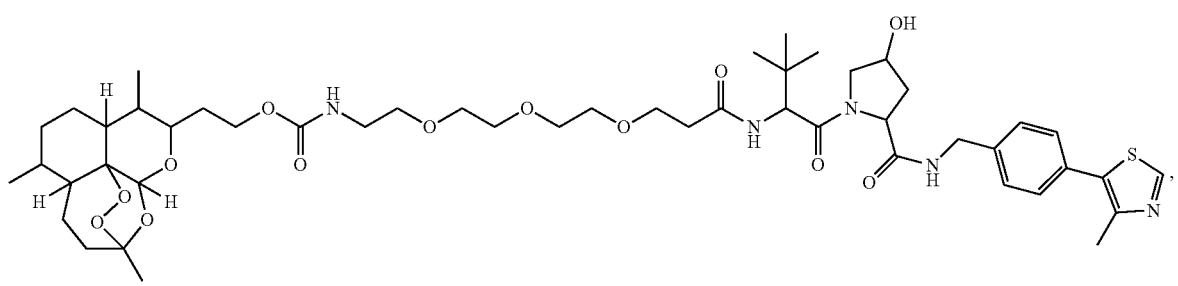

-continued
CL-20
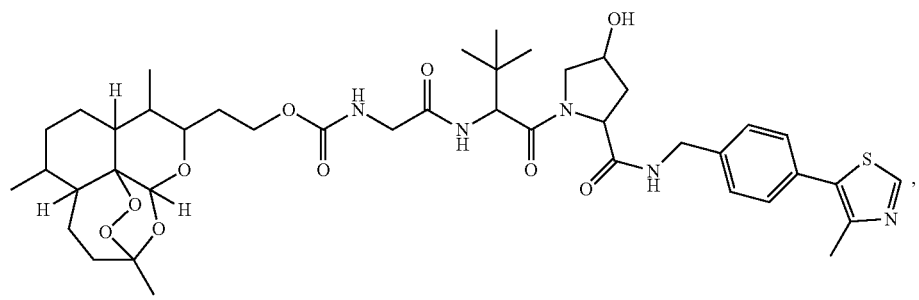
CL-21
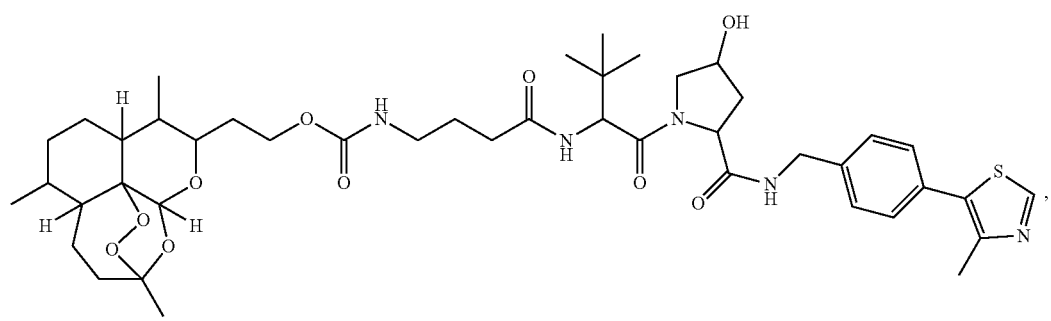
CL-22
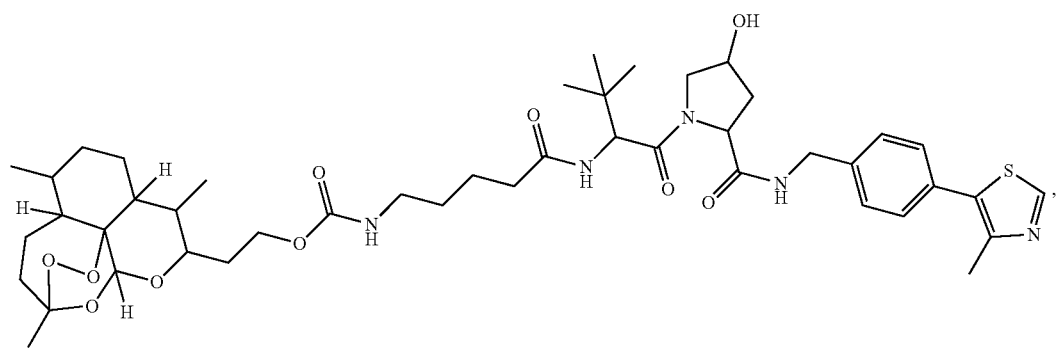
CL-23
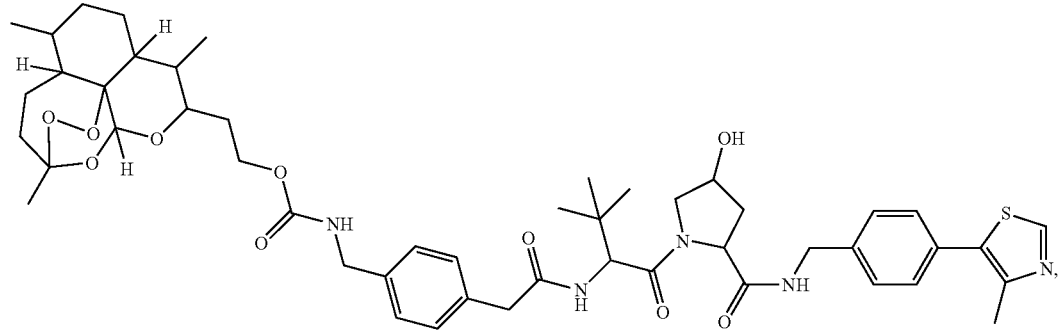
CL-24
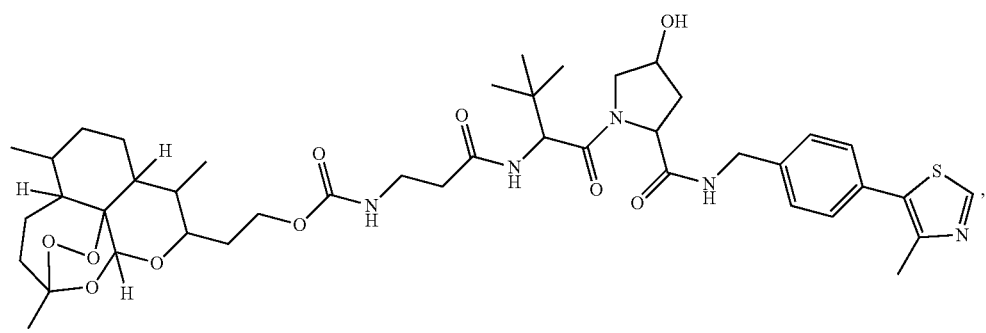

CL-25
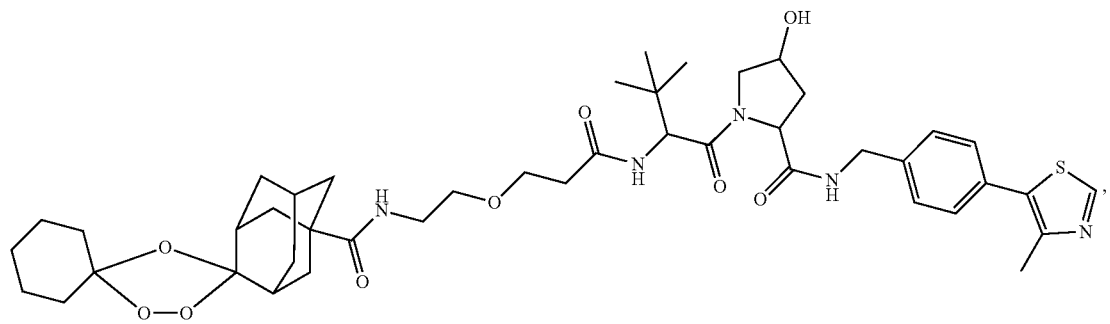
CL-26
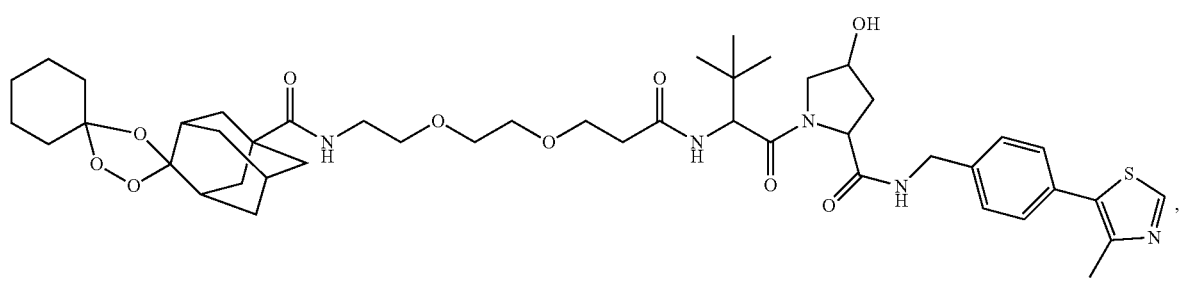
CL-27
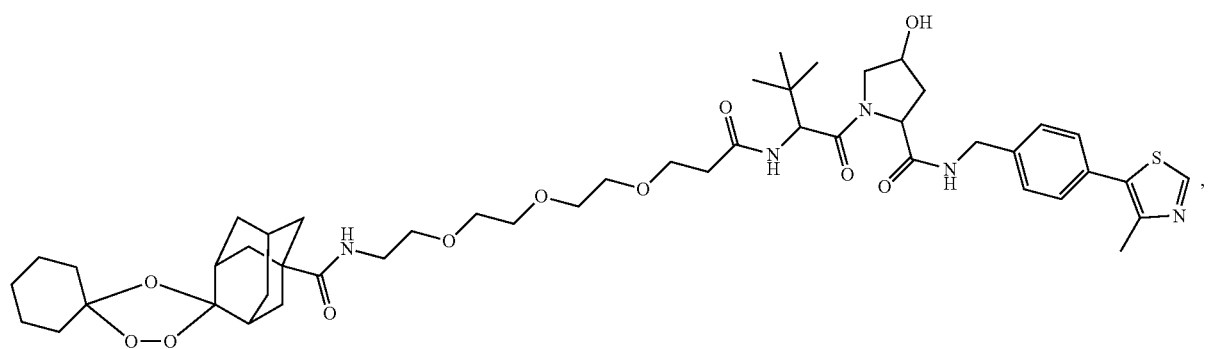
CL-28
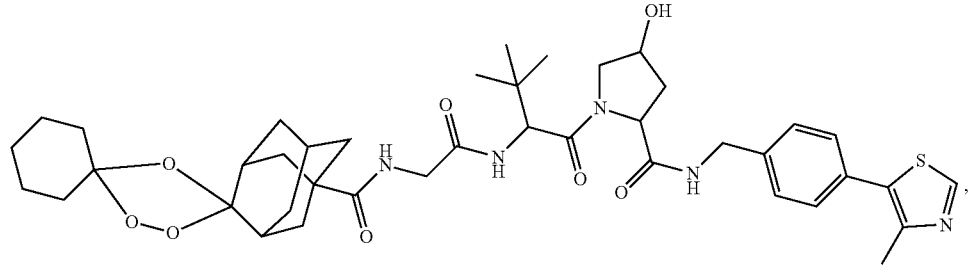
CL-29
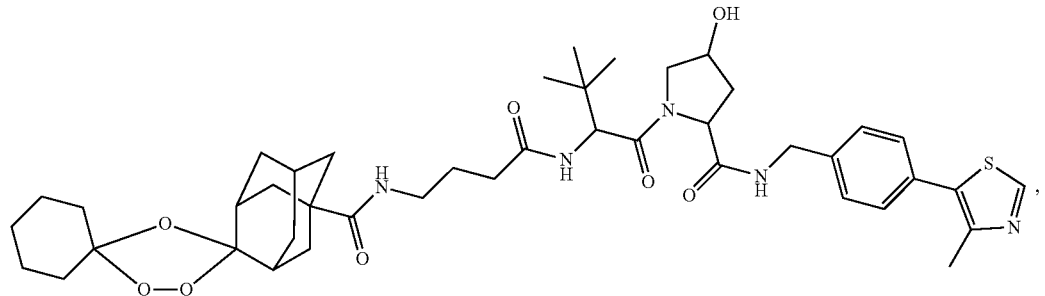

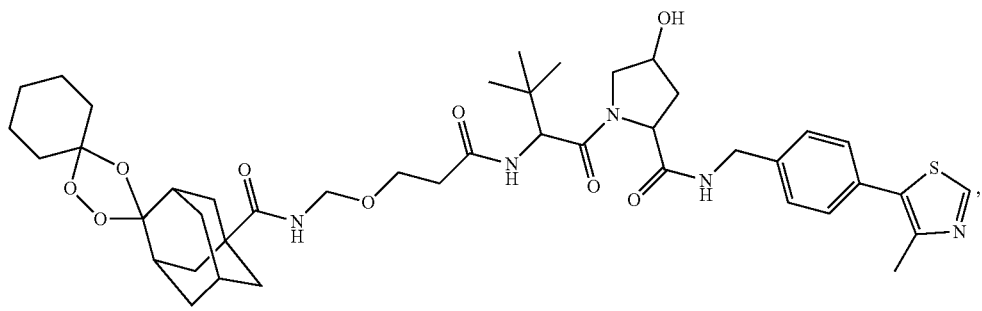
CL-30
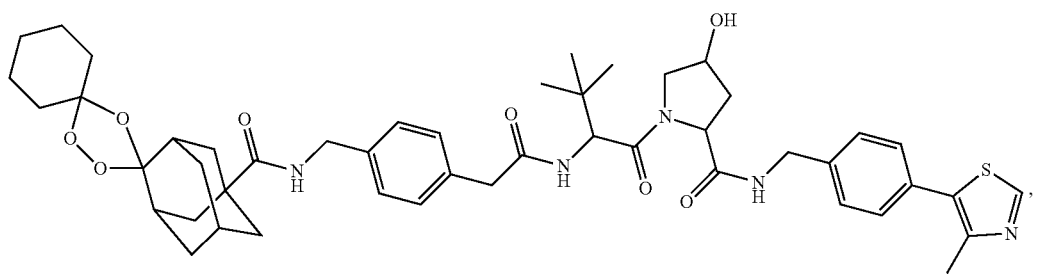
CL-31
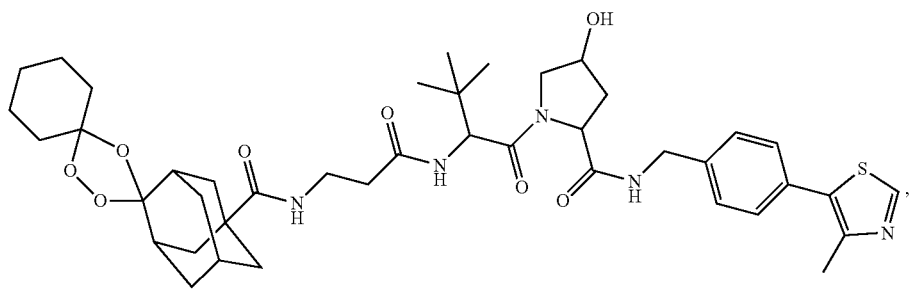
CL-32
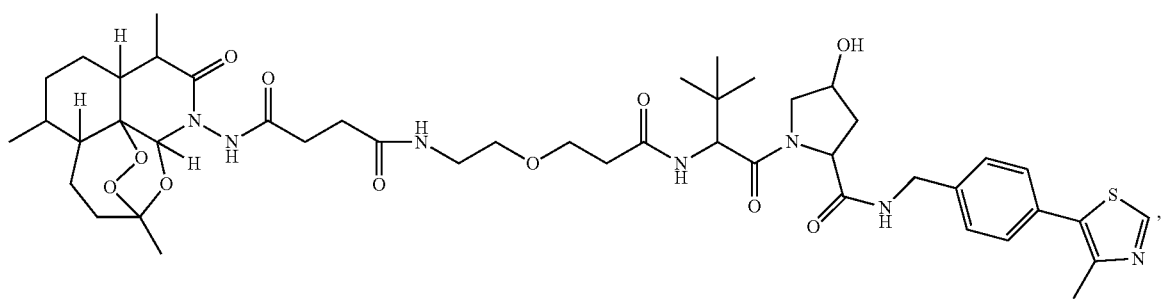
CL-33
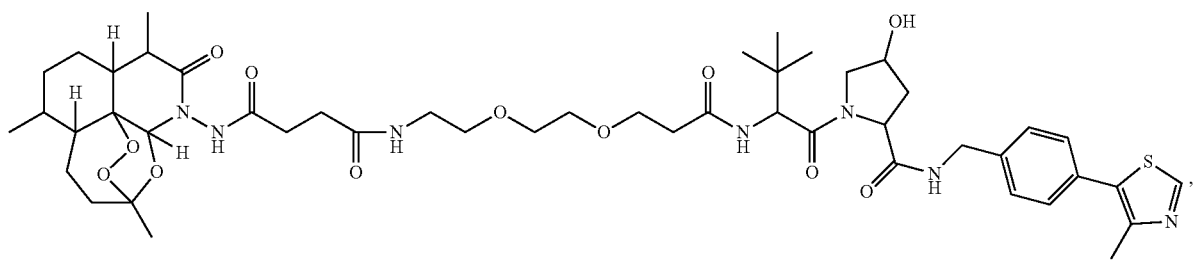
CL-34

CL-35
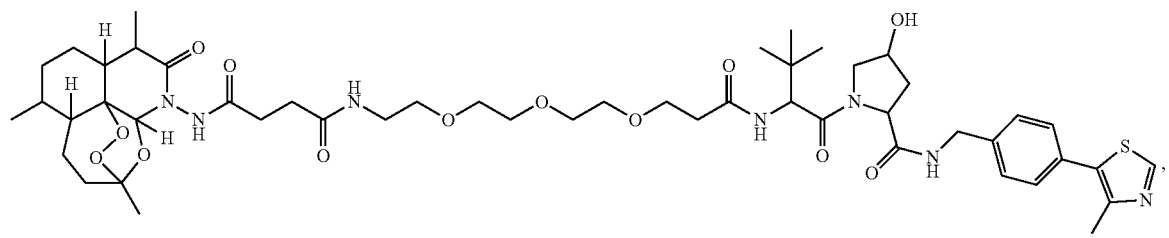
CL-36
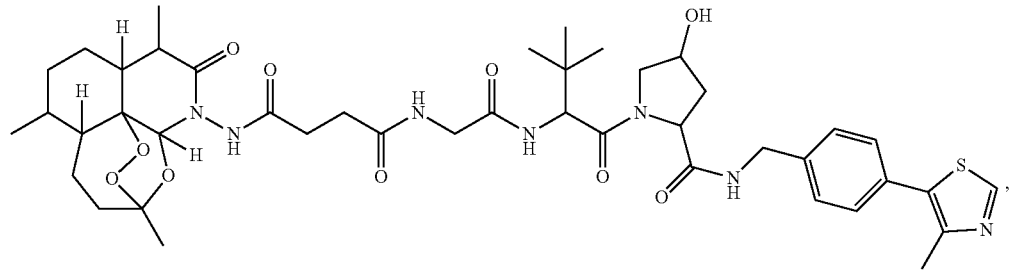
CL-37
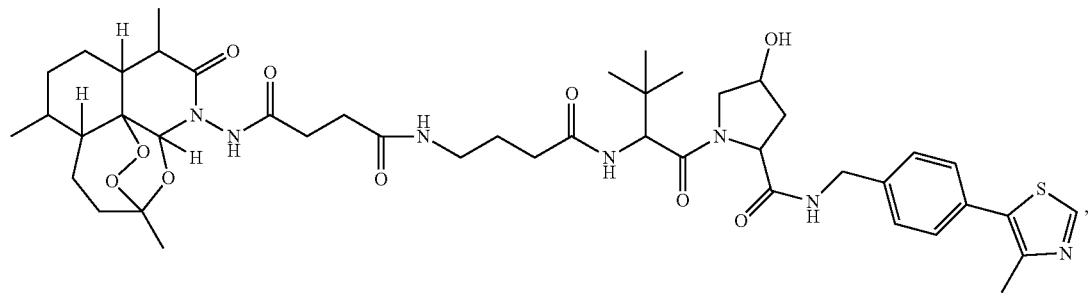
CL-38
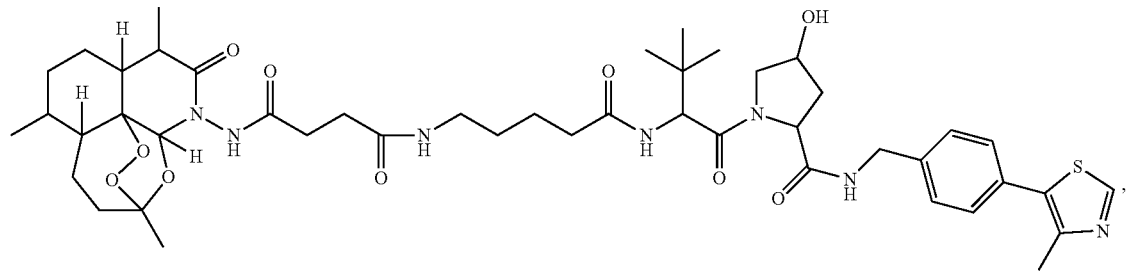
CL-39
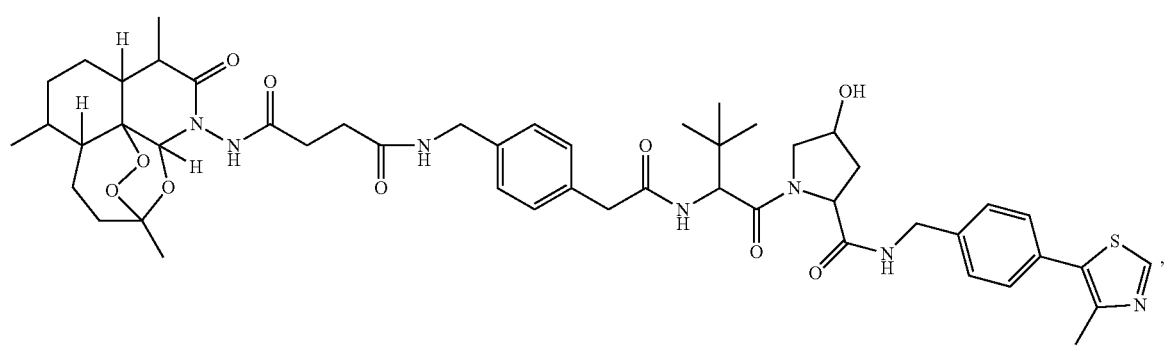

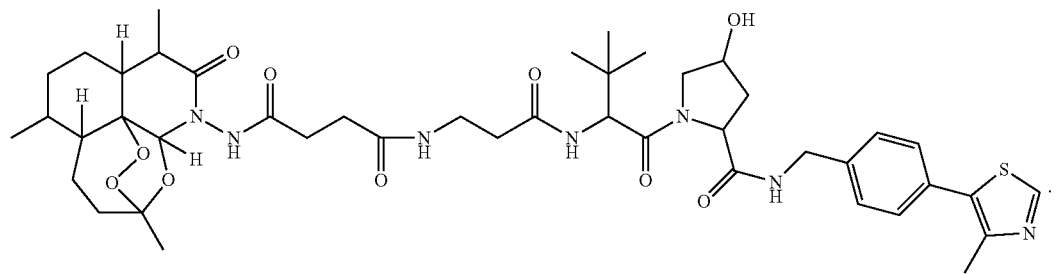
CL-40
8. The compound of claim 1, which is selected from the following structures:
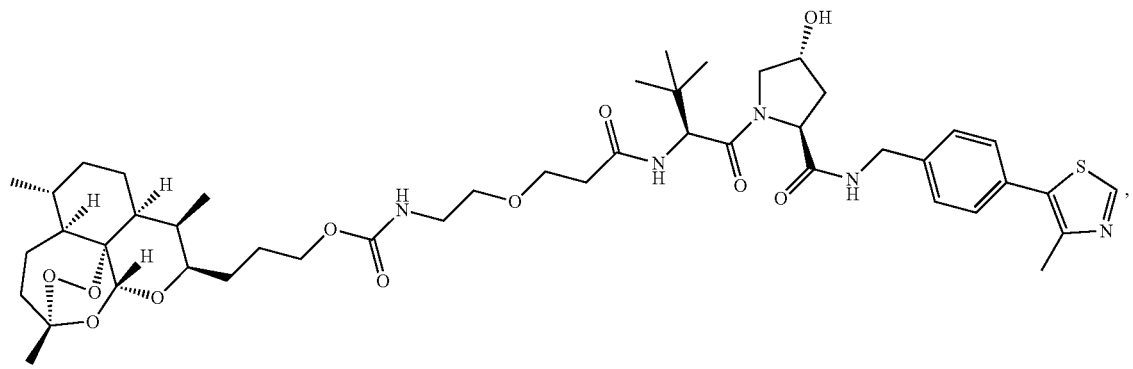
CL-1-T
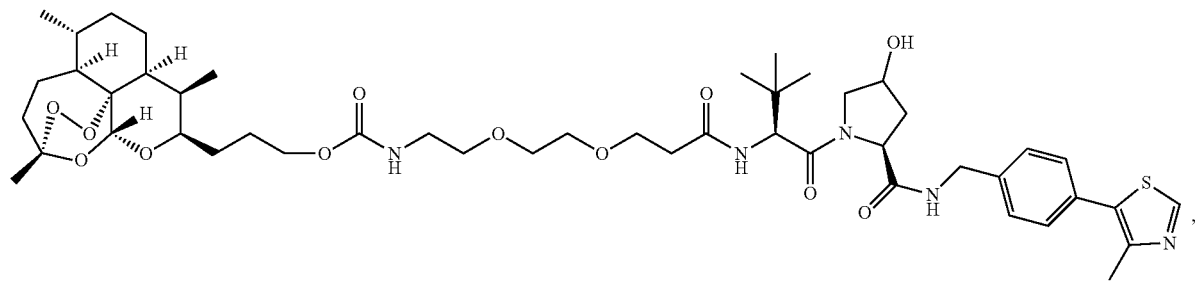
CL-2-T
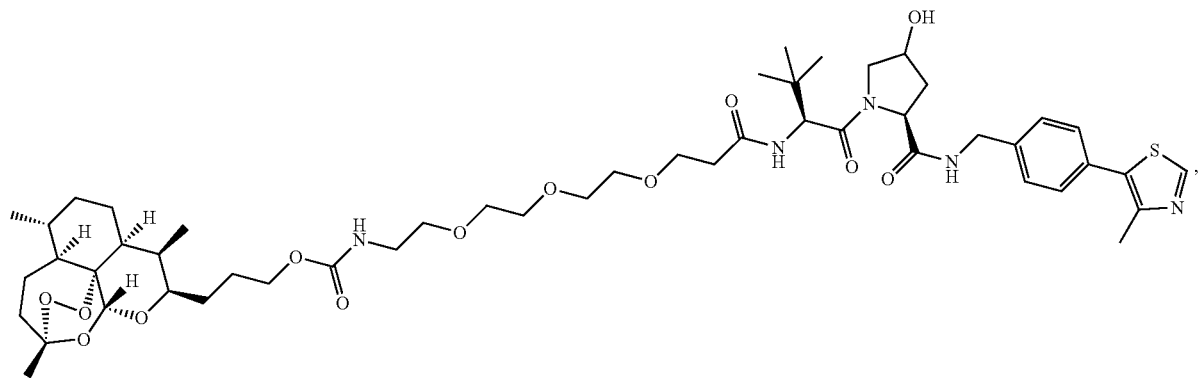
CL-3-T CL-4-T
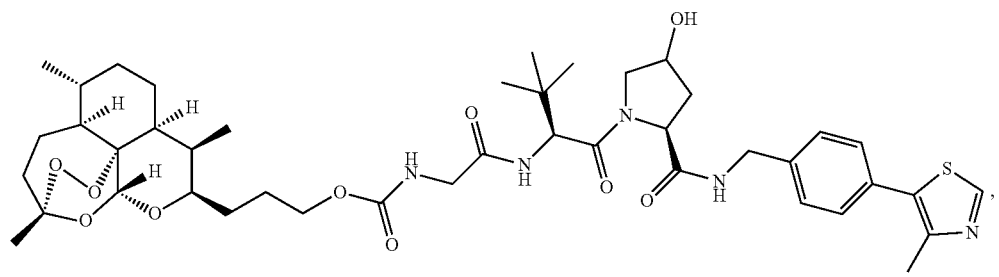
CL-5-T
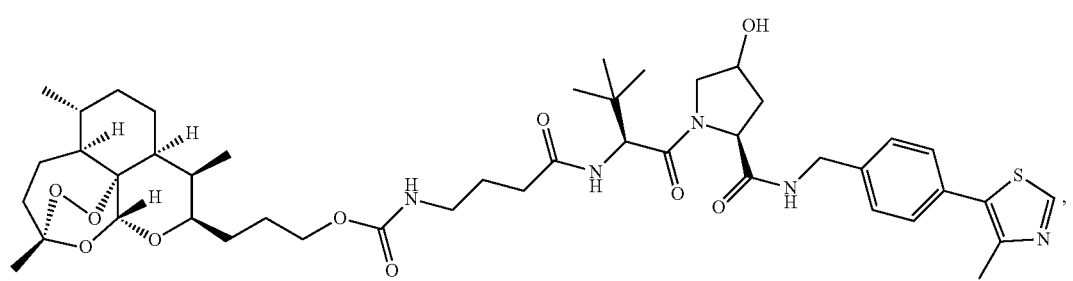
CL-6-T
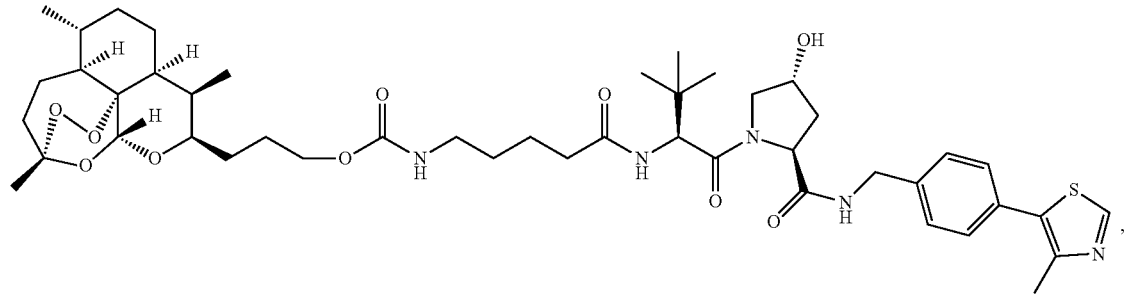
CL-7-T
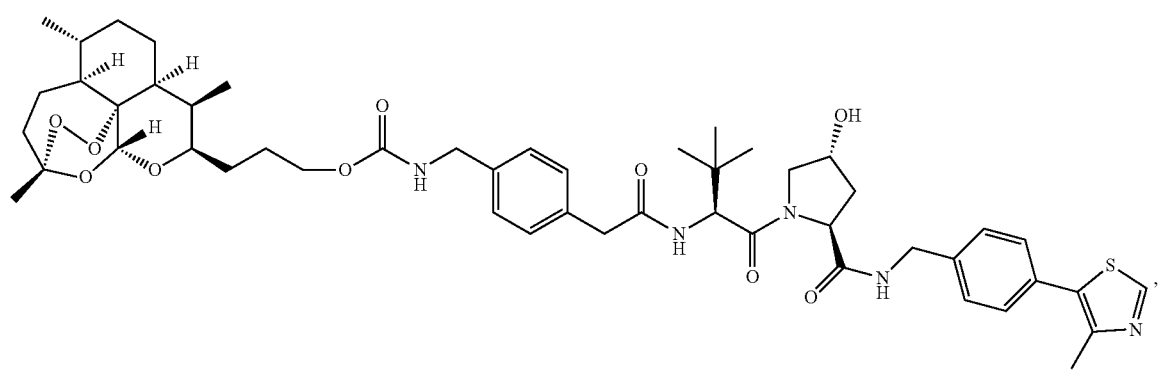
CL-8-T
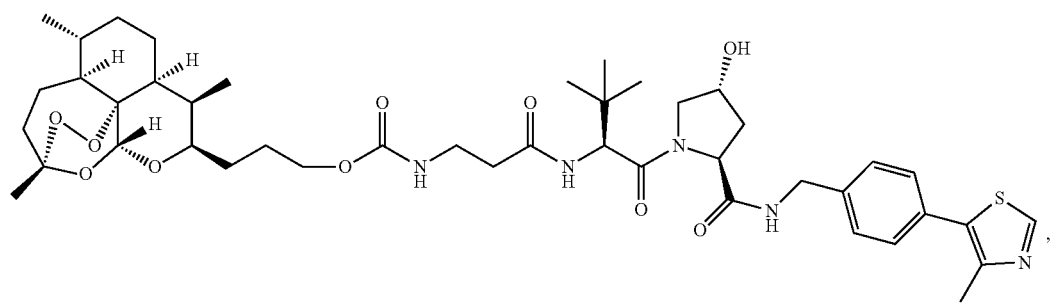

-continued
CL-9-T
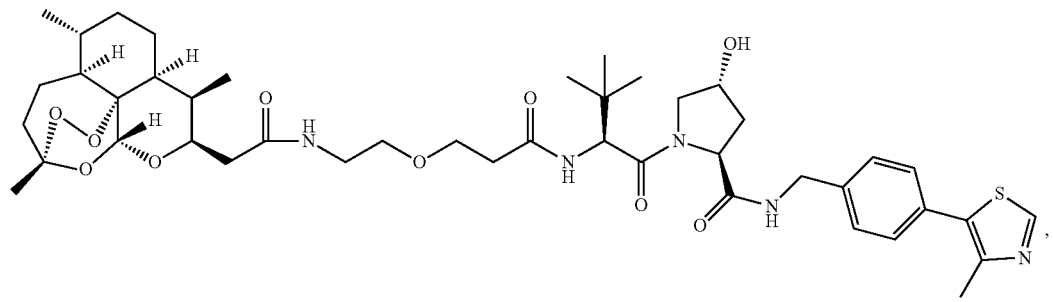
CL-10-T
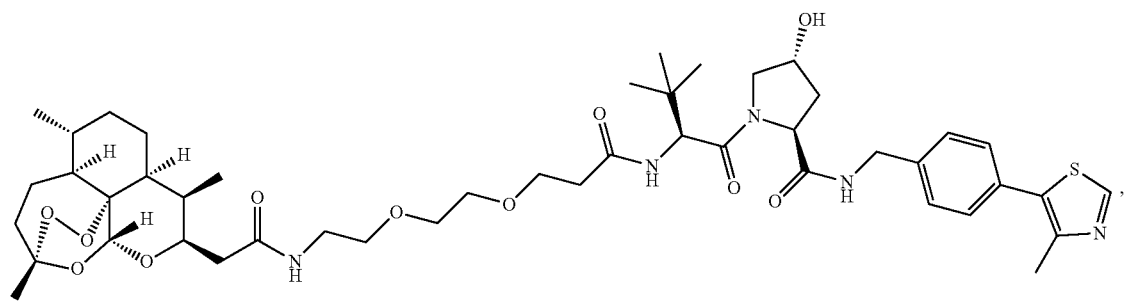
C-11-T
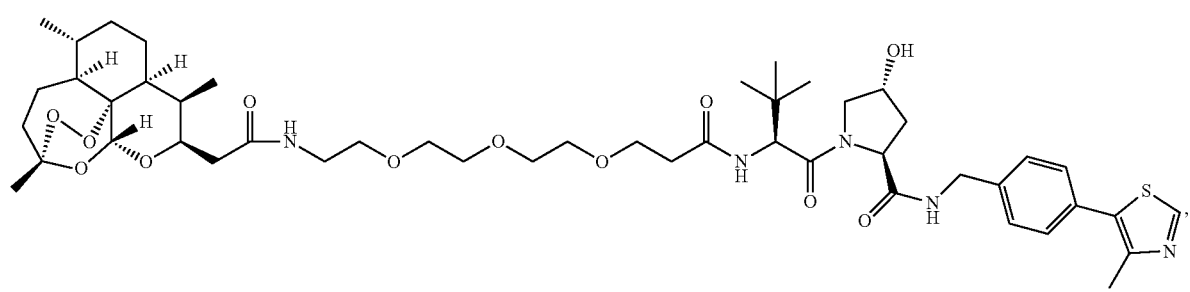
CL-12-T
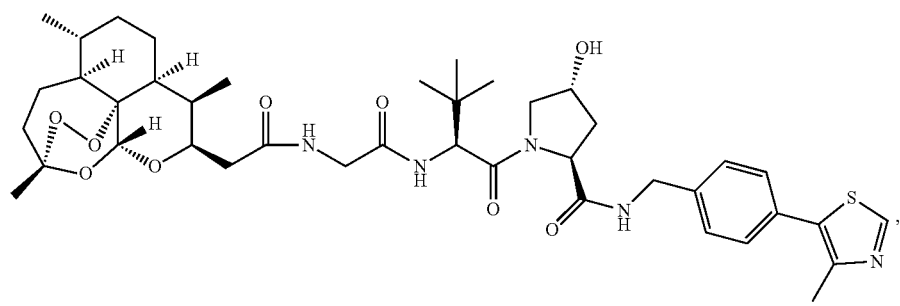
CL-13-T
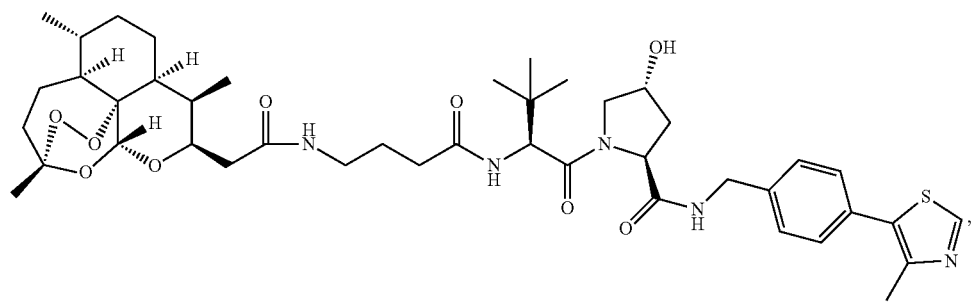

-continued
CL-14-T
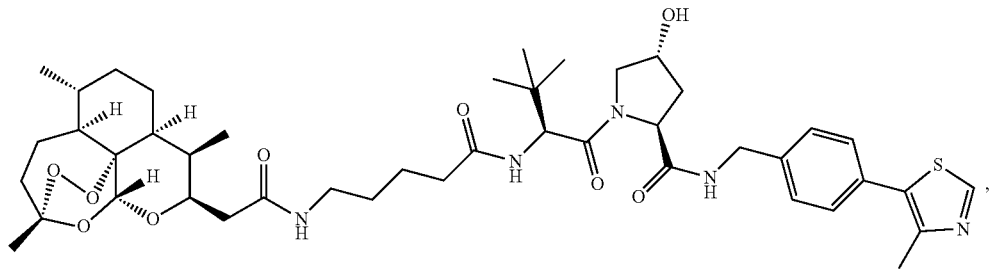
CL-15-T
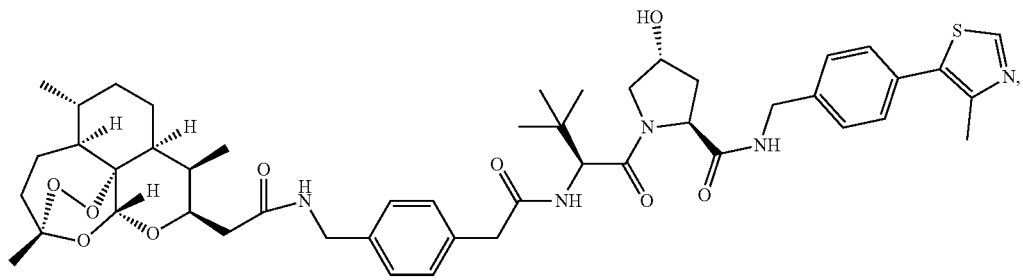
CL-16-T
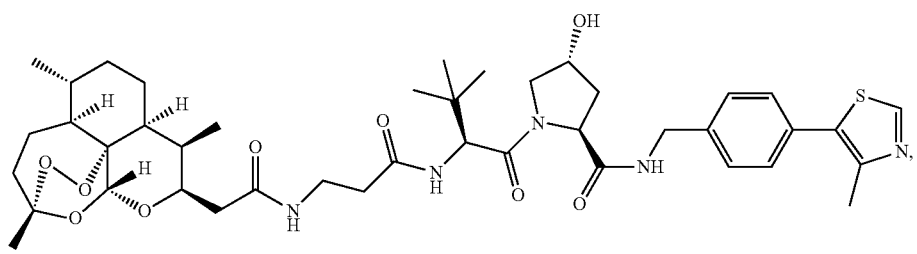
CL-17-T
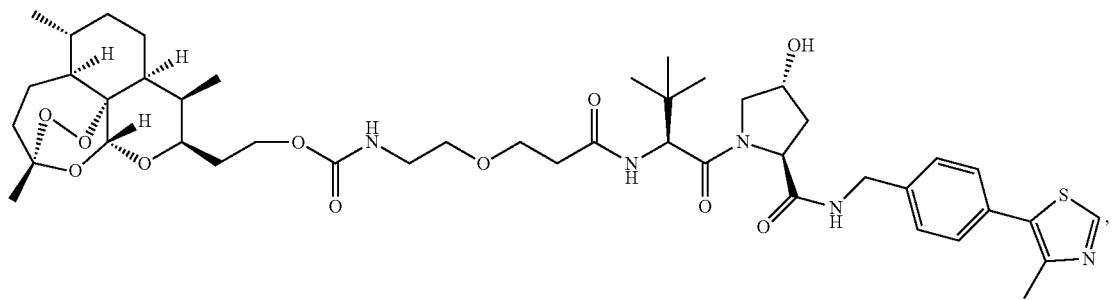
CL-18-T
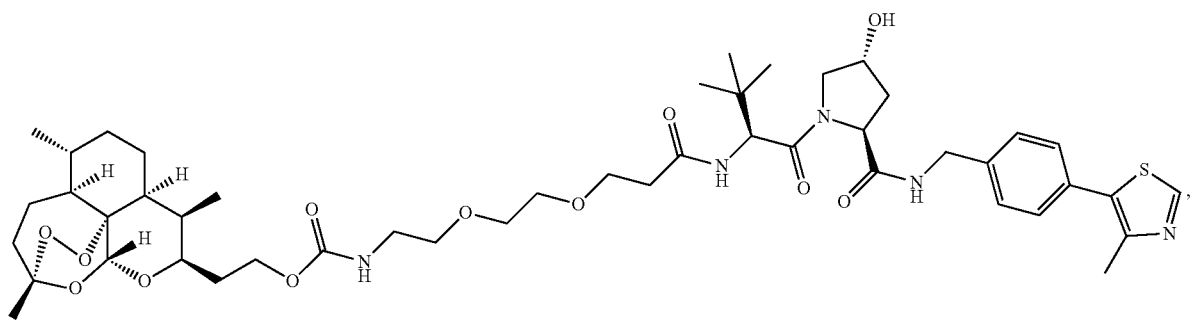

-continued
CL-19-T
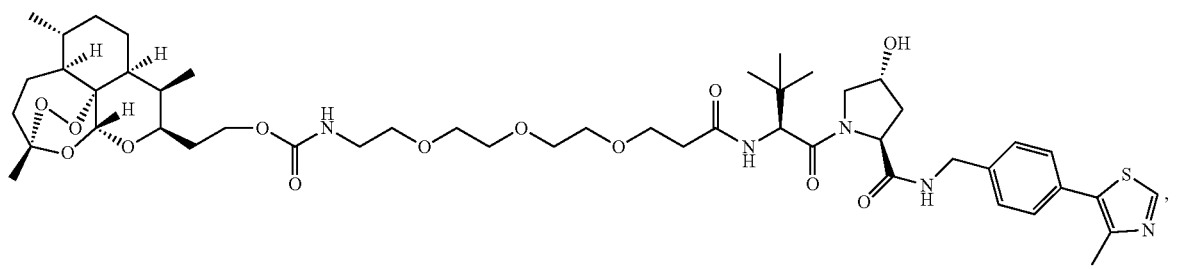
CL-20-T
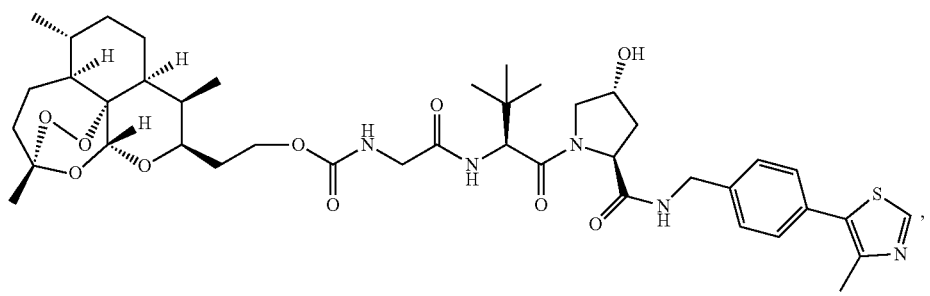
CL-21-T
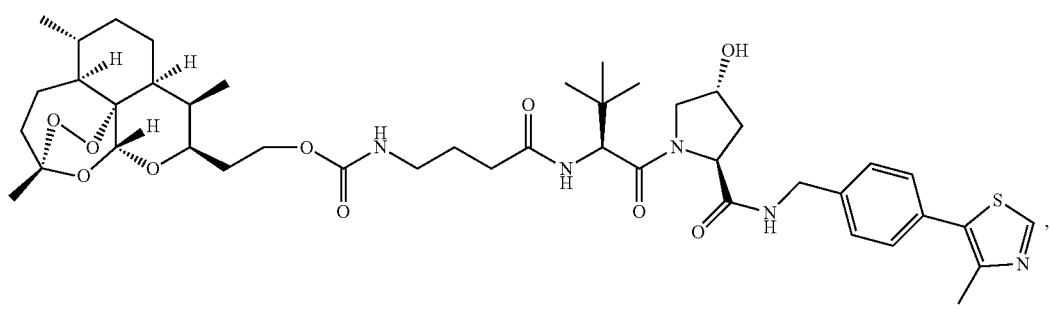
CL-22-T
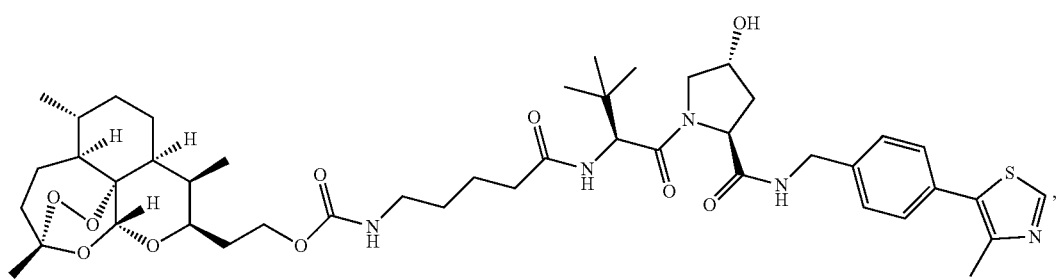
CL-23-T
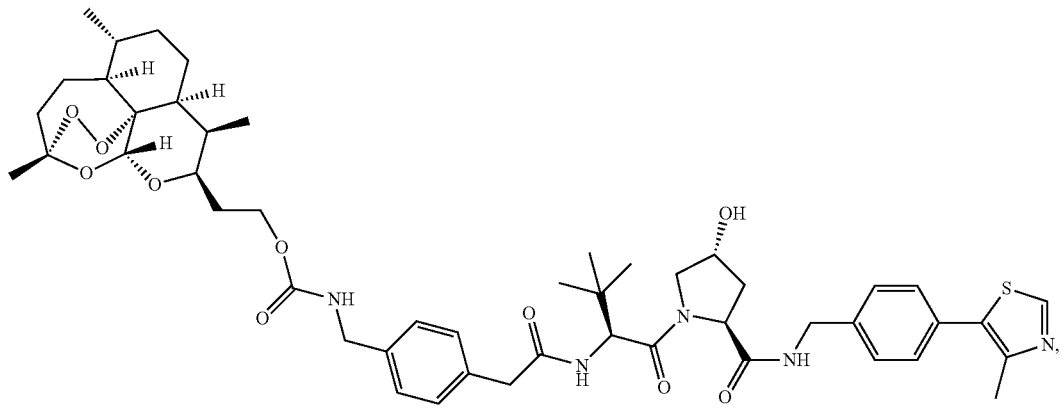

CL-24-T

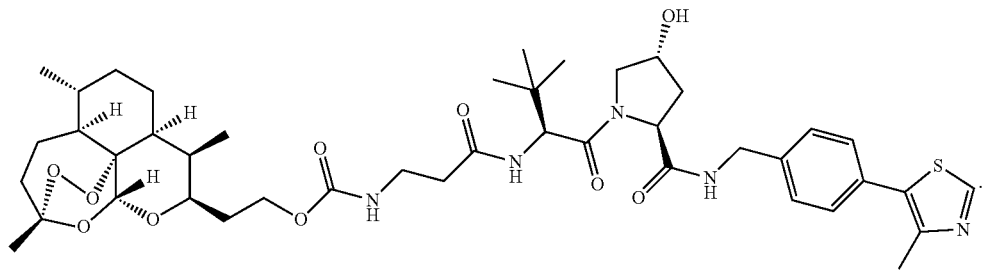

9. A pharmaceutical composition comprising a compound of claim 1 or a pharmaceutically acceptable salt, or a pharmaceutically acceptable carrier, excipient, diluent, adjuvant, vehicle or their combination.

10. A method for preventing and/or treating tumors, comprising the step of administrating to a subject in need thereof a compound of claim 1 or a pharmaceutically acceptable salt or a composition of claim 9.

11. The method of claim 10, wherein the tumors include leukemia and lymphoma.

* * * * *